United States Patent
Caldwell et al.

(10) Patent No.: US 10,414,775 B2
(45) Date of Patent: Sep. 17, 2019

(54) COMPOUNDS USEFUL FOR ALTERING THE LEVELS OF BILE ACIDS FOR THE TREATMENT OF DIABETES AND CARDIOMETABOLIC DISEASE

(71) Applicant: Merck Sharp & Dohme Corp., Rahway, NJ (US)

(72) Inventors: John P. Caldwell, Ringwood, NJ (US); Mary Ann Caplen, Sayreville, NJ (US); Jared N. Cumming, Garwood, NJ (US); Kevin D. Dykstra, West Milford, NJ (US); Alan Hruza, Hackettstown, NJ (US); Claire Lankin, High Bridge, NJ (US); Derun Li, Scotch Plains, NJ (US); Hong Liu, Hillsborough, NJ (US); Amy McCracken, Berkeley Heights, NJ (US); Brian McKittrick, New Vernon, NJ (US); Ashwin Rao, Morganville, NJ (US); Jayaram Tagat, Westfield, NJ (US); Haiqun Tang, Belle Mead, NJ (US); Brandon M. Taoka, Hoboken, NJ (US); Andreas Verras, New York, NY (US); Shawn P. Walsh, Bridgewater, NJ (US); Wen-Lian Wu, Green Brook, NJ (US); Tianyuan Zhang, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/324,604

(22) PCT Filed: Aug. 10, 2017

(86) PCT No.: PCT/US2017/046183
§ 371 (c)(1),
(2) Date: Feb. 11, 2019

(87) PCT Pub. No.: WO2018/034917
PCT Pub. Date: Feb. 22, 2018

(65) Prior Publication Data
US 2019/0218224 A1    Jul. 18, 2019

Related U.S. Application Data

(60) Provisional application No. 62/374,976, filed on Aug. 15, 2016.

(51) Int. Cl.
*C07D 519/00* (2006.01)
*C07D 487/04* (2006.01)
*C07D 498/04* (2006.01)

(52) U.S. Cl.
CPC ......... *C07D 487/04* (2013.01); *C07D 498/04* (2013.01); *C07D 519/00* (2013.01)

(58) Field of Classification Search
CPC .................................................. C07D 519/00
See application file for complete search history.

(56) References Cited

U.S. PATENT DOCUMENTS

| 7,173,036 | B2 | 2/2007 | Sircar et al. | |
|---|---|---|---|---|
| 7,220,856 | B2 * | 5/2007 | Dunning | C07D 215/46 540/484 |
| 2007/0004763 | A1 | 1/2007 | Baindur et al. | |
| 2007/0259880 | A1 | 11/2007 | Sakashita et al. | |
| 2009/0306048 | A1 * | 12/2009 | Kilburn | C07D 211/62 514/216 |
| 2012/0157436 | A1 | 6/2012 | Dean et al. | |
| 2013/0012485 | A1 | 1/2013 | Baschlin et al. | |
| 2013/0296237 | A1 | 11/2013 | Kastan et al. | |

FOREIGN PATENT DOCUMENTS

| WO | WO-2006053024 A2 * | 5/2006 | .......... C07D 221/20 |
|---|---|---|---|
| WO | WO2009001128 A1 | 12/2008 | |
| WO | WO2012009649 A1 | 1/2012 | |
| WO | WO2018034917 A1 | 2/2018 | |
| WO | WO2018034918 A1 | 2/2018 | |

OTHER PUBLICATIONS

Hawkins, Jia Li et al., Cholic Acid Mediates Negative Feedback Regulation of Bile Acid Snthesis in Mice, The Journal of Clinical Investigation, 2002, No. 8, pp. 1191-1200, 110.
Kaur, Achint et al., Loss of Cyp8b1 Improves Glucose Homeostasis by Increasing GLP-1, Diabetes Journal, 2014, 1168-1179, 64.
Murphy, Charlotte et al., Cholic Acid as Key Regulator of Cholesterol Synthesis, Intestinal Absorption and Hepatic Storage in Mice, Biochimica et Biophysica Acta, 2005, 167-175, 1735.
Slatis, Katharina et al., Abolished Synthesis of Cholic Acid Reduces Atherosclerotic Development in Apolipoprotein E Knockout Mice, Journal of Lipid Research, 2010, 3289-3298, 51.
Staels, Bart et al., Bile Acids and Metabolic Regulation: Mechanisms and Clinical Responses to Bile Acid Sequestration, Diabetes Care, 2009, Supplement 2, S237-S245, 32.
Wang, Jin et al., Critical Role of Cholic Acid for Development of Hypercholesterolemia and Gallstones in Diabetic Mice, Biochemical and Biophysical Research Communications, 2006, 1382-1388, 342.

* cited by examiner

*Primary Examiner* — Alexander R Pagano
(74) *Attorney, Agent, or Firm* — Janet E. Fair; Catherine D. Fitch

(57) ABSTRACT

Described herein are compounds of Formula I or a pharmaceutically acceptable salt thereof. The compounds of Formula I act as Cyp8b1 inhibitors and can be useful in preventing, treating or acting as a remedial agent for diabetes and cardiovascular disease.

18 Claims, No Drawings

COMPOUNDS USEFUL FOR ALTERING THE LEVELS OF BILE ACIDS FOR THE TREATMENT OF DIABETES AND CARDIOMETABOLIC DISEASE

CROSS-REFERENCE TO RELATED APPLICATIONS

This application is a U.S. National Phase application under 35 U.S.C. § 371 of PCT Application No. PCT/US2017/046183, filed Aug. 10, 2017, which published as WO2018/034917 A1 on Feb. 22, 2018, and claims priority under 35 U.S.C. § 365(b) from U.S. provisional patent application No. 62/374,976, filed Aug. 15, 2016.

TECHNICAL FIELD

The present invention is directed to compounds useful for altering the levels of bile acids for the treatment of diabetes and cardiometabolic disease. Specifically, the compounds inhibit cytochrome P450, family 8, subfamily B, polypeptide 1 (hereinafter also referred to as "Cyp8b1"), and can be useful in preventing, treating or acting as a remedial agent for diabetes mellitus and cardiometabolic disease.

BACKGROUND

Bile acids are amphiphilic molecules synthesized from cholesterol in the liver. They are physiological detergents that maintain cholesterol homeostasis (Staels B, Fonseca V. A., *Bile acids and metabolic regulation: mechanisms and clinical responses to bile acid sequestration*, Diabetes Care. 2009 November; 32 Suppl 2:S237-45.). Bile acid synthesis is a multi-step process consisting of two distinct pathways, the classical and the alternate. The classical pathway accounts for the majority of bile acids produced. Hydrophobic cholic acid (CA) is the major resulting bile acid and cytochrome P450, family 8, subfamily B, polypeptide 1 (Cyp8b1) plays a critical role in its production. Inhibition of Cyp8b1 reduces the amount of cholic acid in the overall bile acid pool which causes an increase in the amount of alternative bile acids to make up for the deficiency. In humans, the other major bile acid is chenodeoxycholic acid (CDCA) and the amount of CDCA is increased upon inhibition of Cyp8b1. This has been demonstrated in a mouse model.

Mice with targeted disruption of Cyp8b1 (Cyp8b1-/-) fail to produce CA. (Li-Hawkins J, Gafvels M, Olin M, Lund E G, Andersson U, Schuster G, et al, *Cholic acid mediates negative feedback regulation of bile acid synthesis in mice*. J. Clin. Invest. 377 20020 ct.; 110(8): 1191-200). The fraction of the bile acid pool that would have been occupied by CA is predominantly replaced by hydrophilic bile acid species, α- and β-muricholates, in Cyp8b1-/- mice (since CDCA is converted into muricholic acid (MCA) in rodent livers, the main bile acids found in rodents are CA/MCA instead of CA/CDCA in humans). The resulting increase in hydrophilic bile acid species leads to a reduction in both intestinal absorption and hepatic accumulation of cholesterol (Murphy C, Parini P, Wang J, Björkhem I, Eggertsen G, Gifvels M, *Cholic acid as key regulator of cholesterol synthesis, intestinal absorption and hepatic storage in mice*, Biochim. Biophys. Acta. 2005 Aug. 15; 1735(3): 167-75). Cyp8b1-/-×ApoE-/- mice show reduced atherosclerotic plaques, owing to decreased levels of apolipoprotein B (ApoB)-containing lipoproteins in the plasma, reduced hepatic cholesteryl esters and enhanced bile acid synthesis (Slatis K, Gafvels M, Kannisto K, Ovchinnikova O, Pauls-son-Berne G, Parini P, et al., *Abolished synthesis of cholic acid reduces atherosclerotic development in apolipoprotein E knockout mice*, J. Lipid Res. 2010 November; 51(11): 3289-98). Furthermore, cholesterol fed Alloxan induced type 1 diabetic Cyp8b1-/- mice are protected against hypercholesterolemia and gall stones (Wang J, Gafvels M, Rudling M, Murphy C, Bjorkhem I, Einarsson C, et al., *Critical role of cholic acid for development of hypercholesterolemia and gallstones in diabetic mice*, Biochem. Biophys. Res. Commun. 2006 Apr. 21; 342(4):1382-8). These findings suggest that the absence of Cyp8b1 may be beneficial in cases of metabolic syndrome.

Also, it has been found that absence of Cyp8b1 results in improved glucose tolerance, insulin sensitivity and 3-cell function, mediated by absence of CA in Cyp8b1-/- mice (Achint Kaurl, Jay V. Patankar, Willeke de Haanl, Piers Ruddlel, Nadeeja Wijesekaral, Albert K. Groen, C. Bruce Verchere, Roshni R. Singaraja and Michael R. Hayden, *Loss of Cyp8b1 improves glucose homeostasis by increasing GLP-1*, Diabetes, Published online before print Oct. 22, 2014, doi: 10.2337/db14-0716). The absence of biliary CA results in reduced intestinal fat absorption and leads to increased free fatty acids reaching the ileal L-cells. Increased free fatty acids reaching the ileal L-cells, causes the ileal L-cells to increase secretion of the incretin hormone glucagon like peptide-1 (GLP-1). GLP-1 in turn increases the biosynthesis and secretion of insulin from β-cells, leading to the improved glucose tolerance observed in the Cyp8b1-/- mice.

Thus, inhibition of Cyp8b1 causes a decrease in cholic acid (CA) levels and an increase in chenodeoxycholic acid (CDCA) levels. Altering the CA/CDCA ratio plays an important role in cholesterol absorption and homeostasis. As such, there is a need for Cyp8b1 inhibitors that are useful in treating cardiometabolic diseases associated with elevated LDL, such as atherosclerosis, fatty liver and nonalcoholic steatohepatitis (NASH). Also, there is a need for Cyp8b1 inhibitors that are useful for treating noninsulin-dependent diabetes (NIDDM), hyperglycemia, and other symptoms associated with NIDDM.

SUMMARY

A compound of Formula I:

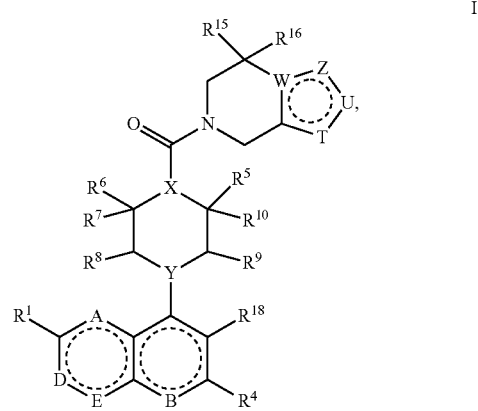

wherein A, B, D, E, T, U, W, X, Y, Z, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are described below.

The compounds described herein are Cyp8b1 inhibitors, which can be useful in the prevention, treatment or amelioration of cardiometabolic diseases associated with elevated LDL, such as atherosclerosis, fatty liver and nonalcoholic steatohepatitis (NASH), and noninsulin-dependent diabetes (NIDDM), hyperglycemia, and other symptoms associated with NIDDM.

DETAILED DESCRIPTION

Compounds

Described herein are compounds of Formula I:

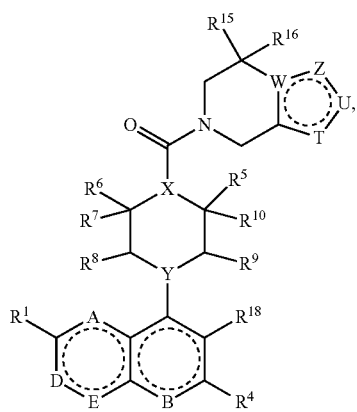

I or a pharmaceutically acceptable salt thereof, wherein:
A is N or $CR^7$;
B is N or NO;
D is N, $NR^2$ or $CR^2$;
E is N or $CR^3$;
T is N or $CR^{12}$, wherein T is not $CR^{12}$ when W is C and Z is $CR^{14}$ and U is $CR^{13}$;
U is N, O or $CR^{13}$, wherein U is not $CR^{13}$ when W is C and T is $CR^{12}$ and Z is $CR^{14}$;
Z is N, S, O or $CR^{14}$, wherein Z is not $CR^{14}$ when W is C and T is $CR^{12}$ and U is $CR^{13}$;
W is N or C, wherein W is not C when T is $CR^{12}$ and U is $CR^{13}$ and Z is $CR^{14}$;
X is N or $CR^{11}$;
Y is N or CH;
$R^1$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, COOC$_1$-$C_6$alkyl, COOC$_1$-$C_6$alkyl$C_3$-$C_6$cycloalkyl and oxazole;
$R^2$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_1$-$C_6$alkoxy$C_3$-$C_6$cycloalkyl, $C_1$-$C_6$alkyl, halo$C_1$-$C_6$alkyl, $C_3$-$C_6$cycloalkyl, $C_2$-$C_6$alkenyl, $C_1$-$C_6$alkyl$C_3$-$C_6$cycloalkyl, —OC$_1$-$C_6$alkyl$C_3$-$C_6$cycloalkyl, COOC$_1$-$C_6$alkyl, COC$_1$-$C_6$alkyl, COC$_3$-$C_6$cycloalkyl, COOC$_1$-$C_6$alkyl$C_3$-$C_6$cycloalkyl, CONH($C_1$-$C_6$alkyl), CONH($C_1$-$C_6$alkyl $C_3$-$C_6$cycloalkyl), CONH($C_3$-$C_6$cycloalkyl), SO$_2$($C_1$-$C_6$alkyl), pyridine, $C_1$-$C_6$alkoxypyridine, triazole, and oxazole, wherein the oxazole may be substituted with one or more $C_1$-$C_6$alkyl substituents;

$R^3$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, COOC$_1$-$C_6$alkyl, COOC$_1$-$C_6$alkyl$C_3$-$C_6$cycloalkyl and oxazole;

$R^4$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, COOC$_1$-$C_6$alkyl, COOC$_1$-$C_6$alkyl$C_3$-$C_6$cycloalkyl and oxazole;

$R^5$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^{10}$ forms a $C_3$-$C_6$cycloalkyl;

$R^6$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^7$ forms a $C_3$-$C_6$cycloalkyl, or when taken with $R^{11}$ forms a $C_3$-$C_6$cycloalkyl;

$R^7$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^6$ forms a $C_3$-$C_6$cycloalkyl;

$R^8$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl;

$R^9$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl;

$R^{10}$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^5$ forms a $C_3$-$C_6$cycloalkyl;

$R^{11}$ is selected from the group consisting of hydrogen, halogen, OH, $C_1$-$C_6$alkyl, and halo$C_1$-$C_6$alkyl or when taken with $R^6$ forms a $C_3$-$C_6$cycloalkyl;

$R^{12}$ is selected from the group consisting of hydrogen, halogen, OH, $C_1$-$C_6$alkyl, $C_3$-$C_6$cycloalkyl and halo$C_1$-$C_6$alkyl;

$R^{13}$ is selected from the group consisting of hydrogen, halogen, OH, $C_1$-$C_6$alkyl, $C_3$-$C_6$cycloalkyl and halo$C_1$-$C_6$alkyl;

$R^{14}$ is selected from the group consisting of hydrogen, halogen, OH, $C_1$-$C_6$alkyl, $C_3$-$C_6$cycloalkyl and halo$C_1$-$C_6$alkyl;

$R^{15}$ is selected from the group consisting of hydrogen, halogen, OH, $C_1$-$C_6$alkyl, and halo$C_1$-$C_6$alkyl;

$R^{16}$ is selected from the group consisting of hydrogen, halogen, OH, $C_1$-$C_6$alkyl, and halo$C_1$-$C_6$alkyl;

$R^{17}$ is selected from the group consisting of hydrogen, halogen, $C_1$-$C_6$alkyl, $C_1$-$C_6$alkoxy, and halo$C_1$-$C_6$alkyl; and $R^{18}$ is selected from the group consisting of hydrogen, halogen, $C_1$-$C_6$alkyl, $C_3$-$C_6$cycloalkyl, $C_1$-$C_6$alkoxy, NO$^2$, CONH$_2$, halo$C_1$-$C_6$alkyl and COOC$_1$-$C_6$alkyl.

In certain embodiments, described herein are compounds of Formula I:
Formula I:

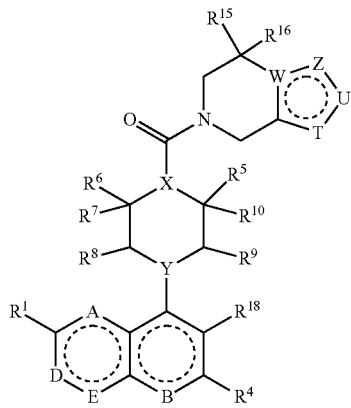

or a pharmaceutically acceptable salt thereof, wherein:
A is N or $CR^{17}$;
B is N or NO;
D is N, $NR^2$ or $CR^2$;
E is N or $CR^3$;
T is N or $CR^{12}$, wherein T is not $CR^{12}$ when W is C and Z is $CR^{14}$ and U is $CR^{13}$;
U is N, O or $CR^{13}$, wherein U is not $CR^{13}$ when W is C and T is $CR^{12}$ and Z is $CR^{14}$;
Z is N, S, O or $CR^{14}$, wherein Z is not $CR^{14}$ when W is C and T is $CR^{12}$ and U is $CR^{13}$;
W is N or C, wherein W is not C when T is $CR^{12}$ and U is $CR^{13}$ and Z is $CR^{14}$;
X is N or $CR^{11}$;
Y is N or CH;
$R^1$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, COOC$_1$-$C_6$alkyl, COOC$_1$-$C_6$alkyl$C_3$-$C_6$cycloalkyl and oxazole;
$R^2$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_1$-$C_6$alkoxy$C_3$-$C_6$cycloalkyl, $C_1$-$C_6$alkyl, halo$C_1$-$C_6$alkyl, $C_3$-$C_6$cycloalkyl, $C_2$-$C_6$alkenyl, $C_1$-$C_6$alkyl$C_3$-$C_6$cycloalkyl, COOC$_1$-$C_6$alkyl, COC$_1$-$C_6$alkyl, COC$_3$-$C_6$cycloalkyl, COOC$_1$-$C_6$alkyl$C_3$-$C_6$cycloalkyl, CONH($C_1$-$C_6$alkyl), CONH($C_1$-$C_6$alkyl$C_3$-$C_6$cycloalkyl), CONH($C_3$-$C_6$cycloalkyl), SO$_2$($C_1$-$C_6$alkyl), pyridine, $C_1$-$C_6$alkoxypyridine, triazole, and oxazole, wherein the oxazole may be substituted with one or more $C_1$-$C_6$alkyl substituents;
$R^3$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, COOC$_1$-$C_6$alkyl, COOC$_1$-$C_6$alkyl$C_3$-$C_6$cycloalkyl and oxazole;
$R^4$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, COOC$_1$-$C_6$alkyl, COOC$_1$-$C_6$alkyl$C_3$-$C_6$cycloalkyl and oxazole;
$R^5$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^{10}$ forms a $C_3$-$C_6$cycloalkyl;
$R^6$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^7$ forms a $C_3$-$C_6$cycloalkyl, or when taken with $R^{11}$ forms a $C_3$-$C_6$cycloalkyl;
$R^7$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^6$ forms a $C_3$-$C_6$cycloalkyl;
$R^8$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl;
$R^9$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl;
$R^{10}$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^5$ forms a $C_3$-$C_6$cycloalkyl;
$R^{11}$ is selected from the group consisting of hydrogen, halogen, OH, $C_1$-$C_6$alkyl, and halo$C_1$-$C_6$alkyl or when taken with $R^6$ forms a $C_3$-$C_6$cycloalkyl;
$R^{12}$ is selected from the group consisting of hydrogen, halogen, OH, $C_1$-$C_6$alkyl, $C_3$-$C_6$cycloalkyl and halo$C_1$-$C_6$alkyl;
$R^{13}$ is selected from the group consisting of hydrogen, halogen, OH, $C_1$-$C_6$alkyl, $C_3$-$C_6$cycloalkyl and halo$C_1$-$C_6$alkyl;
$R^{14}$ is selected from the group consisting of hydrogen, halogen, OH, $C_1$-$C_6$alkyl, $C_3$-$C_6$cycloalkyl and halo$C_1$-$C_6$alkyl;
$R^{15}$ is selected from the group consisting of hydrogen, halogen, OH, $C_1$-$C_6$alkyl, and halo$C_1$-$C_6$alkyl;
$R^{16}$ is selected from the group consisting of hydrogen, halogen, OH, $C_1$-$C_6$alkyl, and halo$C_1$-$C_6$alkyl;
$R^{17}$ is selected from the group consisting of hydrogen, halogen, $C_1$-$C_6$alkyl, $C_1$-$C_6$alkoxy, and halo$C_1$-$C_6$alkyl; and
$R^{18}$ is selected from the group consisting of hydrogen, halogen, $C_1$-$C_6$alkyl, $C_3$-$C_6$cycloalkyl, $C_1$-$C_6$alkoxy, $NO^2$, $CONH_2$, halo$C_1$-$C_6$alkyl and COOC$_1$-$C_6$alkyl.

With regard to the compounds described herein, A is N or $CR^{17}$. In certain embodiments, A is N. In other embodiments, A is $CR^{17}$.

With regard to the compounds described herein, B is N or NO. In certain embodiments, B is N. In other embodiments, B is NO.

With regard to the compounds described herein, D is N, $NR^2$ or $CR^2$. In certain embodiments, D is N. In other embodiments, D is $CR^2$. In other embodiments, D is $NR^2$.

With regard to the compounds described herein, E is N or $CR^3$. In certain embodiments, E is N. In other embodiments, E is $CR^3$.

With regard to the compounds described herein, T is N or $CR^{12}$. In certain embodiments, T is N. In other embodiments, T is $CR^{12}$. In certain embodiments, T is not $CR^{12}$ when W is C and Z is $CR^{14}$ and U is $CR^{13}$.

With regard to the compounds described herein, U is N, O or $CR^{13}$. In certain embodiments, U is N. In certain embodiments, U is O. In other embodiments, U is $CR^{13}$. In certain embodiments, U is not $CR^{13}$ when W is C and T is $CR^{12}$ and Z is $CR^{14}$.

With regard to the compounds described herein, Z is N, S, O or $CR^{14}$. In certain embodiments, Z is N. In other embodiments, Z is S. In yet other embodiments, Z is O. In still other embodiments, Z is $CR^{14}$. In certain embodiments, Z is not $CR^{14}$ when W is C and T is $CR^{12}$ and U is $CR^{13}$.

With regard to the compounds described herein, W is N or C. In certain embodiments, W is N. In other embodiments, W is C. In certain embodiments, W is not C when T is $CR^{12}$ and U is $CR^{13}$ and Z is $CR^{14}$.

With regard to the compounds described herein, X is N or $CR^{11}$. In certain embodiments, X is N. In other embodiments, X is $CR^{11}$.

With regard to the compounds described herein, Y is N or CH. In certain embodiments, Y is N. In other embodiments, Y is CH.

With regard to the compounds described herein, $R^1$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, COO$C_1$-$C_6$alkyl, COO$C_1$-$C_6$alkyl$C_3$-$C_6$cycloalkyl and oxazole.

In certain embodiments, $R^1$ is hydrogen. In certain embodiments, $R^1$ is halogen. Suitable halogens include, but are not limited to, fluorine, chlorine, bromine and iodine. In certain embodiments, $R^1$ is CN. In certain embodiments, $R^1$ is OH. In certain embodiments, $R^1$ is $C_1$-$C_6$alkylOH. Suitable $C_1$-$C_6$alkylOHs include, but are not limited to, methanol, propanol, ethanol and butanol.

In certain embodiments, $R^1$ is $C_1$-$C_6$alkoxy. Suitable $C_1$-$C_6$alkoxys include but are not limited to, methoxy and ethoxy. In certain embodiments, $R^1$ is halo$C_1$-$C_6$alkoxy. Suitable halo$C_1$-$C_6$alkoxys include, but are not limited to, trifluoromethoxy. In certain embodiments, $R^1$ is $C_1$-$C_6$alkyl$C_1$-$C_6$alkoxy. Suitable $C_1$-$C_6$alkyl$C_1$-$C_6$alkoxys include, but are not limited to, methylpropoxy. In certain embodiments, $R^1$ is $C_3$-$C_6$cycloalkyl$C_1$-$C_6$alkoxy. Suitable $C_3$-$C_6$cycloalkyl$C_1$-$C_6$alkoxys include, but are not limited to, cyclopropylmethoxy. In certain embodiments, $R^1$ is $C_1$-$C_6$alkyl. Suitable $C_1$-$C_6$alkyls include but are not limited to, methyl, ethyl and isopropyl. In certain embodiments, $R^1$ is halo$C_1$-$C_6$alkyl. Suitable halo$C_1$-$C_6$alkyls include, but are not limited to, trifluoromethyl and difluoroethyl. In certain embodiments, $R^1$ is $C_3$-$C_6$cycloalkyl. Suitable $C_3$-$C_6$cycloalkyls include, but are not limited to, cyclopropyl, cyclobutyl, cyclopentyl and cyclohexyl. In certain embodiments, $R^1$ is $C_2$-$C_6$alkenyl. Suitable $C_2$-$C_6$alkenyls include but are not limited to, vinyl.

In certain embodiments, $R^1$ is COO$C_1$-$C_6$alkyl. Suitable COO$C_1$-$C_6$alkyls include, but are not limited to, methoxycarbonyl, ethoxycarbonyl, propoxycarbonyl and butoxycarbonyl. In certain embodiments, $R^1$ is COO$C_1$-$C_6$alkyl$C_3$-$C_6$cycloalkyl.

In certain embodiments, $R^1$ is phenyl. In certain embodiments, $R^1$ is oxazole.

With regard to the compounds described herein, $R^2$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_1$-$C_6$alkoxy$C_3$-$C_6$cycloalkyl, $C_1$-$C_6$alkyl, halo$C_1$-$C_6$alkyl, $C_3$-$C_6$cycloalkyl, $C_2$-$C_6$alkenyl, $C_1$-$C_6$alkyl$C_3$-$C_6$cycloalkyl, —O$C_1$-$C_6$alkyl$C_3$-$C_6$cycloalkyl, COO$C_1$-$C_6$alkyl, CO$C_1$-$C_6$alkyl, CO$C_3$-$C_6$cycloalkyl, COO$C_1$-$C_6$alkyl$C_3$-$C_6$cycloalkyl, CONH($C_1$-$C_6$alkyl), CONH($C_1$-$C_6$alkyl $C_3$-$C_6$cycloalkyl), CONH($C_3$-$C_6$cycloalkyl), $SO_2$($C_1$-$C_6$alkyl), pyridine, $C_1$-$C_6$alkoxypyridine, triazole, and oxazole, wherein the oxazole may be substituted with one or more $C_1$-$C_6$alkyl substituents.

With regard to the compounds described herein, $R^2$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_1$-$C_6$alkoxy$C_3$-$C_6$cycloalkyl, $C_1$-$C_6$alkyl, halo$C_1$-$C_6$alkyl, $C_3$-$C_6$cycloalkyl, $C_2$-$C_6$alkenyl, $C_1$-$C_6$alkyl$C_3$-$C_6$cycloalkyl, COO$C_1$-$C_6$alkyl, CO$C_1$-$C_6$alkyl, CO$C_3$-$C_6$cycloalkyl, COO$C_1$-$C_6$alkyl$C_3$-$C_6$cycloalkyl, CONH($C_1$-$C_6$alkyl), CONH($C_1$-$C_6$alkyl $C_3$-$C_6$cycloalkyl), CONH($C_3$-$C_6$cycloalkyl), $SO_2$($C_1$-$C_6$alkyl), pyridine, $C_1$-$C_6$alkoxypyridine, triazole, and oxazole, wherein the oxazole may be substituted with one or more $C_1$-$C_6$alkyl substituents.

In certain embodiments, $R^2$ is hydrogen. In certain embodiments, $R^2$ is halogen. Suitable halogens include, but are not limited to, fluorine, chlorine, bromine and iodine. In certain embodiments, $R^2$ is CN. In certain embodiments, $R^2$ is OH. In certain embodiments, $R^2$ is $C_1$-$C_6$alkylOH. Suitable $C_1$-$C_6$alkylOHs include, but are not limited to, methanol, propanol, isopropanol, ethanol and butanol.

In certain embodiments, $R^2$ is $C_1$-$C_6$alkoxy. Suitable $C_1$-$C_6$alkoxys include but are not limited to, methoxy and ethoxy. In certain embodiments, $R^2$ is halo$C_1$-$C_6$alkoxy. Suitable halo$C_1$-$C_6$alkoxys include, but are not limited to, trifluoromethoxy and difluoromethoxy. In certain embodiments, $R^2$ is $C_1$-$C_6$alkyl$C_1$-$C_6$alkoxy. Suitable $C_1$-$C_6$alkyl$C_1$-$C_6$alkoxys include, but are not limited to, methylpropoxy. In certain embodiments, $R^2$ is $C_1$-$C_6$alkoxy$C_3$-$C_6$cycloalkyl. Suitable $C_3$-$C_6$cycloalkyl$C_1$-$C_6$alkoxys include, but are not limited to, cyclopropylmethoxy and benzyloxy. In certain embodiments, $R^2$ is $C_1$-$C_6$alkyl. Suitable $C_1$-$C_6$alkyls include but are not limited to, methyl, ethyl and isopropyl. In certain embodiments, $R^2$ is halo$C_1$-$C_6$alkyl. Suitable halo$C_1$-$C_6$alkyls include, but are not limited to, trifluoromethyl, difluoroethyl and difluoroethyl. In certain embodiments, $R^2$ is $C_3$-$C_6$cycloalkyl. Suitable $C_3$-$C_6$cycloalkyls include, but are not limited to, cyclopropyl, cyclobutyl, cyclopentyl, phenyl and cyclohexyl. In certain embodiments, $R^2$ is $C_2$-$C_6$alkenyl. Suitable $C_2$-$C_6$alkenyls include but are not limited to, vinyl. In certain embodiments, $R^2$ is $C_1$-$C_6$alkyl$C_3$-$C_6$cycloalkyl. Suitable $C_1$-$C_6$alkyl$C_3$-$C_6$cycloalkyls include, but are not limited to, cyclopropylmethyl and cyclopropylethyl.

In certain embodiments, $R^2$ is —O$C_1$-$C_6$alkyl$C_3$-$C_6$cycloalkyl. Suitable —O$C_1$-$C_6$alkyl$C_3$-$C_6$cycloalkyls include, but are not limited to, cyclopropylmethoxy.

In certain embodiments, $R^2$ is COO$C_1$-$C_6$alkyl. Suitable COO$C_1$-$C_6$alkyls include, but are not limited to, methoxycarbonyl, ethoxycarbonyl, propoxycarbonyl and butoxycarbonyl. In certain embodiments, $R^2$ is CO$C_1$-$C_6$alkyl. Suitable CO$C_1$-$C_6$alkyls include, but are not limited to, acetyl. In certain embodiments, $R^2$ is COO$C_1$-$C_6$alkyl$C_3$-$C_6$cycloalkyl. Suitable COO$C_1$-$C_6$alkyl$C_3$-$C_6$cycloalkyls include, but are not limited to, —COO-methylcyclopropyl. In certain embodiments, $R^2$ is CO$C_3$-$C_6$cycloalkyl. Suitable CO$C_3$-$C_6$cycloalkyl include, but are not limited to, —CO-cyclopropyl.

In certain embodiments, $R^2$ is CONH($C_1$-$C_6$alkyl). Suitable examples of CONH($C_1$-$C_6$alkyl) include, but are not limited to, CONH(CH$_2$CH$_3$). In certain embodiments, $R^2$ is CONH($C_1$-$C_6$alkyl $C_3$-$C_6$cycloalkyl). Suitable CONH($C_1$-$C_6$alkyl$C_3$-$C_6$cycloalkyl)s include, but are not limited to, CONH(CH$_2$C$_3$Hs). In certain embodiments, $R^2$ is CONH($C_3$-$C_6$cycloalkyl). Suitable CONH($C_3$-$C_6$cycloalkyl)s include, but are not limited to, CONH(bicyclopentane). In certain embodiments, $R^2$ is $SO_2(C_1\text{-}C_6\text{alkyl})$. Suitable examples of $SO_2(C_1\text{-}C_6\text{alkyl})$s include, but are not limited to, methane sulfonyl.

In certain embodiments, $R^2$ is pyridine. In certain embodiments, $R^2$ is $C_1\text{-}C_6\text{alkoxypyridine}$. In certain embodiments, $R^2$ is triazole. In certain embodiments, $R^2$ is phenyl. In certain embodiments, $R^2$ is oxazole. In certain embodiments, $R^2$ is oxazole, wherein the oxazole is substituted with one or more $C_1\text{-}C_6\text{alkyl}$ substituents. For example, when $R^2$ is oxazole, the oxazole is substituted with one methyl.

With regard to the compounds described herein, $R^3$ is selected from the group consisting of hydrogen, halogen, CN, OH, $C_1\text{-}C_6\text{alkylOH}$, $C_1\text{-}C_6\text{alkoxy}$, $C_1\text{-}C_6\text{alkylC}_1\text{-}C_6\text{alkoxy}$, $haloC_1\text{-}C_6\text{alkoxy}$, $C_3\text{-}C_6\text{cycloalkylC}_1\text{-}C_6\text{alkoxy}$, $C_1\text{-}C_6\text{alkyl}$, $haloC_1\text{-}C_6\text{alkyl}$, $C_3\text{-}C_6\text{cycloalkyl}$, $C_2\text{-}C_6\text{alkenyl}$, $COOC_1\text{-}C_6\text{alkyl}$, $COOC_1\text{-}C_6\text{alkylC}_3\text{-}C_6\text{cycloalkyl}$ and oxazole.

In certain embodiments, $R^3$ is hydrogen. In certain embodiments, $R^3$ is halogen. Suitable halogens include, but are not limited to, fluorine, chlorine, bromine and iodine. In certain embodiments, $R^3$ is CN. In certain embodiments, $R^3$ is OH. In certain embodiments, $R^3$ is $C_1\text{-}C_6\text{alkylOH}$. Suitable $C_1\text{-}C_6\text{alkylOH}$s include, but are not limited to, methanol, propanol, ethanol and butanol.

In certain embodiments, $R^3$ is $C_1\text{-}C_6\text{alkoxy}$. Suitable $C_1\text{-}C_6\text{alkoxys}$ include but are not limited to, methoxy and ethoxy. In certain embodiments, $R^3$ is $haloC_1\text{-}C_6\text{alkoxy}$. Suitable $haloC_1\text{-}C_6\text{alkoxys}$ include, but are not limited to, trifluoromethoxy. In certain embodiments, $R^3$ is $C_1\text{-}C_6\text{alkylC}_1\text{-}C_6\text{alkoxy}$. Suitable $C_1\text{-}C_6\text{alkylC}_1\text{-}C_6\text{alkoxys}$ include, but are not limited to, methylpropoxy. In certain embodiments, $R^3$ is $C_3\text{-}C_6\text{cycloalkylC}_1\text{-}C_6\text{alkoxy}$. Suitable $C_3\text{-}C_6\text{cycloalkylC}_1\text{-}C_6\text{alkoxys}$ include, but are not limited to, cyclopropylmethoxy. In certain embodiments, $R^3$ is $C_1\text{-}C_6\text{alkyl}$. Suitable $C_1\text{-}C_6\text{alkyls}$ include but are not limited to, methyl, ethyl and isopropyl. In certain embodiments, $R^3$ is $haloC_1\text{-}C_6\text{alkyl}$. Suitable $haloC_1\text{-}C_6\text{alkyls}$ include, but are not limited to, trifluoromethyl and difluoroethyl. In certain embodiments, $R^3$ is $C_3\text{-}C_6\text{cycloalkyl}$. Suitable $C_3\text{-}C_6\text{cycloalkyls}$ include, but are not limited to, cyclopropyl, cyclobutyl, cyclopentyl and cyclohexyl. In certain embodiments, $R^3$ is $C_2\text{-}C_6\text{alkenyl}$. Suitable $C_2\text{-}C_6\text{alkenyls}$ include but are not limited to, vinyl.

In certain embodiments, $R^3$ is $COOC_1\text{-}C_6\text{alkyl}$. Suitable $COOC_1\text{-}C_6\text{alkyls}$ include, but are not limited to, methoxycarbonyl, ethoxycarbonyl, propoxycarbonyl and butoxycarbonyl. In certain embodiments, $R^3$ is $COOC_1\text{-}C_6\text{alkylC}_3\text{-}C_6\text{cycloalkyl}$.

In certain embodiments, $R^3$ is phenyl. In certain embodiments, $R^3$ is oxazole.

With regard to the compounds described herein, $R^4$ is selected from the group consisting of hydrogen, halogen, CN, OH, $C_1\text{-}C_6\text{alkylOH}$, $C_1\text{-}C_6\text{alkoxy}$, $C_1\text{-}C_6\text{alkylC}_1\text{-}C_6\text{alkoxy}$, $haloC_1\text{-}C_6\text{alkoxy}$, $C_3\text{-}C_6\text{cycloalkylC}_1\text{-}C_6\text{alkoxy}$, $C_1\text{-}C_6\text{alkyl}$, $haloC_1\text{-}C_6\text{alkyl}$, $C_3\text{-}C_6\text{cycloalkyl}$, $C_2\text{-}C_6\text{alkenyl}$, $COOC_1\text{-}C_6\text{alkyl}$, $COOC_1\text{-}C_6\text{alkylC}_3\text{-}C_6\text{cycloalkyl}$ and oxazole.

In certain embodiments, $R^4$ is hydrogen. In certain embodiments, $R^4$ is halogen. Suitable halogens include, but are not limited to, fluorine, chlorine, bromine and iodine. In certain embodiments, $R^4$ is CN. In certain embodiments, $R^4$ is OH. In certain embodiments, $R^4$ is $C_1\text{-}C_6\text{alkylOH}$. Suitable $C_1\text{-}C_6\text{alkylOH}$s include, but are not limited to, methanol, propanol, ethanol and butanol.

In certain embodiments, $R^4$ is $C_1\text{-}C_6\text{alkoxy}$. Suitable $C_1\text{-}C_6\text{alkoxys}$ include, but are not limited to, methoxy and ethoxy. In certain embodiments, $R^4$ is $haloC_1\text{-}C_6\text{alkoxy}$. Suitable $haloC_1\text{-}C_6\text{alkoxys}$ include, but are not limited to, trifluoromethoxy. In certain embodiments, $R^4$ is $C_1\text{-}C_6\text{alkylC}_1\text{-}C_6\text{alkoxy}$. Suitable $C_1\text{-}C_6\text{alkylC}_1\text{-}C_6\text{alkoxys}$ include, but are not limited to, methylpropoxy. In certain embodiments, $R^4$ is $C_3\text{-}C_6\text{cycloalkylC}_1\text{-}C_6\text{alkoxy}$. Suitable $C_3\text{-}C_6\text{cycloalkylC}_1\text{-}C_6\text{alkoxys}$ include, but are not limited to, cyclopropylmethoxy. In certain embodiments, $R^4$ is $C_1\text{-}C_6\text{alkyl}$. Suitable $C_1\text{-}C_6\text{alkyls}$ include but are not limited to, methyl, ethyl and isopropyl. In certain embodiments, $R^4$ is $haloC_1\text{-}C_6\text{alkyl}$. Suitable $haloC_1\text{-}C_6\text{alkyls}$ include, but are not limited to, trifluoromethyl and difluoroethyl. In certain embodiments, $R^4$ is $C_3\text{-}C_6\text{cycloalkyl}$. Suitable $C_3\text{-}C_6\text{cycloalkyls}$ include, but are not limited to, cyclopropyl, cyclobutyl, cyclopentyl and cyclohexyl. In certain embodiments, $R^4$ is $C_2\text{-}C_6\text{alkenyl}$. Suitable $C_2\text{-}C_6\text{alkenyls}$ include but are not limited to, vinyl.

In certain embodiments, $R^4$ is $COOC_1\text{-}C_6\text{alkyl}$. Suitable $COOC_1\text{-}C_6\text{alkyls}$ include, but are not limited to, methoxycarbonyl, ethoxycarbonyl, propoxycarbonyl and butoxycarbonyl. In certain embodiments, $R^4$ is $COOC_1\text{-}C_6\text{alkylC}_3\text{-}C_6\text{cycloalkyl}$.

In certain embodiments, $R^4$ is phenyl. In certain embodiments, $R^4$ is oxazole.

With regard to the compounds described herein, $R^5$ is selected from the group consisting of hydrogen, halogen, $C_1\text{-}C_6\text{alkyl}$, $C_3\text{-}C_6\text{cycloalkyl}$, $C_1\text{-}C_6\text{alkoxy}$ and $haloC_1\text{-}C_6\text{alkyl}$ or when taken with $R^{10}$, and the carbon to which $R^{10}$ and $R^5$ are attached, forms a $C_3\text{-}C_6\text{cycloalkyl}$.

In certain embodiments, $R^5$ is hydrogen. In certain embodiments, $R^5$ is halogen. Suitable halogens include, but are not limited to, fluorine, chlorine, bromine and iodine. In certain embodiments, $R^5$ is $C_1\text{-}C_6\text{alkyl}$. Suitable $C_1\text{-}C_6\text{alkyls}$ include but are not limited to, methyl, ethyl and isopropyl. In certain embodiments, $R^5$ is $C_3\text{-}C_6\text{cycloalkyl}$. Suitable $C_3\text{-}C_6\text{cycloalkyls}$ include, but are not limited to, cyclopropyl and cyclobutyl. In certain embodiments, $R^5$ is $C_1\text{-}C_6\text{alkoxy}$. Suitable $C_1\text{-}C_6\text{alkoxys}$ include but are not limited to, methoxy and ethoxy. In certain embodiments, $R^5$ is $haloC_1\text{-}C_6\text{alkyl}$. Suitable $haloC_1\text{-}C_6\text{alkyls}$ include but are not limited to, trifluoromethyl.

In certain embodiments, $R^5$ forms a $C_3\text{-}C_6\text{cycloalkyl}$ with $R^{10}$ and the carbon in which $R^5$ and $R^{10}$ are attached. Suitable $C_3\text{-}C_6\text{cycloalkyls}$ include, but are not limited to, cyclopropyl and cyclobutyl.

With regard to the compounds described herein, $R^6$ is selected from the group consisting of hydrogen, halogen, $C_1\text{-}C_6\text{alkyl}$, $C_3\text{-}C_6\text{cycloalkyl}$, $C_1\text{-}C_6\text{alkoxy}$ and $haloC_1\text{-}C_6\text{alkyl}$ or when taken with $R^7$, and the carbon to which $R^6$ and $R^7$ are attached, forms a $C_3\text{-}C_6\text{cycloalkyl}$ or when taken with $R^{11}$, and the carbon to which $R^6$ and $R^{11}$ are attached, form a $C_3\text{-}C_6\text{cycloalkyl}$.

In certain embodiments, $R^6$ is hydrogen. In certain embodiments, $R^6$ is halogen. Suitable halogens include, but are not limited to, fluorine, chlorine, bromine and iodine. In certain embodiments, $R^6$ is $C_1\text{-}C_6\text{alkyl}$. Suitable $C_1\text{-}C_6\text{alkyls}$ include but are not limited to, methyl, ethyl and isopropyl. In certain embodiments, $R^6$ is $C_3\text{-}C_6\text{cycloalkyl}$. Suitable $C_3\text{-}C_6\text{cycloalkyls}$ include, but are not limited to, cyclopropyl and cyclobutyl. In certain embodiments, $R^6$ is $C_1\text{-}C_6\text{alkoxy}$. Suitable $C_1\text{-}C_6\text{alkoxys}$ include but are not limited to, methoxy and ethoxy. In certain embodiments, $R^6$ is $haloC_1\text{-}C_6\text{alkyl}$. Suitable $haloC_1\text{-}C_6\text{alkyls}$ include but are not limited to, trifluoromethyl.

In certain embodiments, $R^6$ forms a $C_3$-$C_6$cycloalkyl with $R^7$ and the carbon in which $R^6$ and $R^7$ are attached. Suitable $C_3$-$C_6$cycloalkyls include, but are not limited to, cyclopropyl and cyclobutyl.

In certain embodiments, $R^6$ forms a $C_3$-$C_6$cycloalkyl with $R^{11}$ and the carbon in which $R^6$ and $R^{11}$ are attached. Suitable $C_3$-$C_6$cycloalkyls include, but are not limited to, cyclopropyl and cyclobutyl.

With regard to the compounds described herein, $R^7$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^6$, and the carbon to which $R^7$ and $R^6$ are attached, forms a $C_3$-$C_6$cycloalkyl.

In certain embodiments, $R^7$ is hydrogen. In certain embodiments, $R^7$ is halogen. Suitable halogens include, but are not limited to, fluorine, chlorine, bromine and iodine. In certain embodiments, $R^7$ is $C_1$-$C_6$alkyl. Suitable $C_1$-$C_6$alkyls include but are not limited to, methyl, ethyl and isopropyl. In certain embodiments, $R^7$ is $C_3$-$C_6$cycloalkyl. Suitable $C_3$-$C_6$cycloalkyls include, but are not limited to, cyclopropyl and cyclobutyl. In certain embodiments, $R^7$ is $C_1$-$C_6$alkoxy. Suitable $C_1$-$C_6$alkoxys include but are not limited to, methoxy and ethoxy. In certain embodiments, $R^7$ is halo$C_1$-$C_6$alkyl. Suitable halo$C_1$-$C_6$alkyls include but are not limited to, trifluoromethyl.

In certain embodiments, $R^7$ forms a $C_3$-$C_6$cycloalkyl with $R^6$ and the carbon in which $R^7$ and $R^6$ are attached. Suitable $C_3$-$C_6$cycloalkyls include, but are not limited to, cyclopropyl and cyclobutyl.

With regard to the compounds described herein, $R^8$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl.

In certain embodiments, $R^8$ is hydrogen. In certain embodiments, $R^8$ is halogen. Suitable halogens include, but are not limited to, fluorine, chlorine, bromine and iodine. In certain embodiments, $R^8$ is $C_1$-$C_6$alkyl. Suitable $C_1$-$C_6$alkyls include but are not limited to, methyl, ethyl and isopropyl. In certain embodiments, $R^8$ is $C_3$-$C_6$cycloalkyl. Suitable $C_3$-$C_6$cycloalkyls include, but are not limited to, cyclopropyl and cyclobutyl. In certain embodiments, $R^8$ is $C_1$-$C_6$alkoxy. Suitable $C_1$-$C_6$alkoxys include but are not limited to, methoxy and ethoxy. In certain embodiments, $R^8$ is halo$C_1$-$C_6$alkyl. Suitable halo$C_1$-$C_6$alkyls include but are not limited to, trifluoromethyl.

With regard to the compounds described herein, $R^9$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl.

In certain embodiments, $R^9$ is hydrogen. In certain embodiments, $R^9$ is halogen. Suitable halogens include, but are not limited to, fluorine, chlorine, bromine and iodine. In certain embodiments, $R^9$ is $C_1$-$C_6$alkyl. Suitable $C_1$-$C_6$alkyls include but are not limited to, methyl, ethyl and isopropyl. In certain embodiments, $R^9$ is $C_3$-$C_6$cycloalkyl. Suitable $C_3$-$C_6$cycloalkyls include, but are not limited to, cyclopropyl and cyclobutyl. In certain embodiments, $R^9$ is $C_1$-$C_6$alkoxy. Suitable $C_1$-$C_6$alkoxys include but are not limited to, methoxy and ethoxy. In certain embodiments, $R^9$ is halo$C_1$-$C_6$alkyl. Suitable halo$C_1$-$C_6$alkyls include but are not limited to, trifluoromethyl.

With regard to the compounds described herein, $R^{10}$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^5$, and the carbon to which $R^{10}$ and $R^5$ are attached, forms a $C_3$-$C_6$cycloalkyl.

In certain embodiments, $R^{10}$ is hydrogen. In certain embodiments, $R^{10}$ is halogen. Suitable halogens include, but are not limited to, fluorine, chlorine, bromine and iodine. In certain embodiments, $R^{10}$ is $C_1$-$C_6$alkyl. Suitable $C_1$-$C_6$alkyls include but are not limited to, methyl, ethyl and isopropyl. In certain embodiments, $R^{10}$ is $C_3$-$C_6$cycloalkyl. Suitable $C_3$-$C_6$cycloalkyls include, but are not limited to, cyclopropyl and cyclobutyl. In certain embodiments, $R^{10}$ is $C_1$-$C_6$alkoxy. Suitable $C_1$-$C_6$alkoxys include but are not limited to, methoxy and ethoxy. In certain embodiments, $R^{10}$ is halo$C_1$-$C_6$alkyl. Suitable halo$C_1$-$C_6$alkyls include but are not limited to, trifluoromethyl.

In certain embodiments, $R^{10}$ forms a $C_3$-$C_6$cycloalkyl with $R^5$ and the carbon in which $R^{10}$ and $R^5$ are attached. Suitable $C_3$-$C_6$cycloalkyls include, but are not limited to, cyclopropyl and cyclobutyl.

With regard to the compounds described herein, $R^{11}$ is selected from the group consisting of hydrogen, halogen, OH, $C_1$-$C_6$alkyl, and halo$C_1$-$C_6$alkyl or when taken with $R^6$, and the carbon to which $R^{11}$ and $R^6$ are attached, forms a $C_3$-$C_6$cycloalkyl. In certain embodiments, $R^{11}$ is hydrogen. In certain embodiments, $R^{11}$ is halogen. Suitable halogens include, but are not limited to, fluorine, chlorine, bromine and iodine. In certain embodiments, $R^{11}$ is —OH. In certain embodiments, $R^{11}$ is $C_1$-$C_6$alkyl. Suitable $C_1$-$C_6$alkyls include but are not limited to, methyl, ethyl and isopropyl. In certain embodiments, $R^{11}$ is halo$C_1$-$C_6$alkyl. Suitable halo$C_1$-$C_6$alkyls include but are not limited to, trifluoromethyl.

In certain embodiments, $R^{11}$ forms a $C_3$-$C_6$cycloalkyl with $R^6$ and the carbon in which $R^{11}$ and $R^6$ are attached. Suitable $C_3$-$C_6$cycloalkyls include, but are not limited to, cyclopropyl and cyclobutyl.

With regard to the compounds described herein, $R^{12}$ is selected from the group consisting of hydrogen, halogen, OH, $C_1$-$C_6$alkyl, $C_3$-$C_6$cycloalkyl and halo$C_1$-$C_6$alkyl. In certain embodiments, $R^{12}$ is hydrogen. In certain embodiments, $R^{12}$ is halogen. Suitable halogens include, but are not limited to, fluorine, chlorine, bromine and iodine. In certain embodiments, $R^{12}$ is —OH. In certain embodiments, $R^{12}$ is $C_1$-$C_6$alkyl. Suitable $C_1$-$C_6$alkyls include but are not limited to, methyl, ethyl and isopropyl. In certain embodiments, $R^{12}$ is $C_3$-$C_6$cycloalkyl. Suitable $C_3$-$C_6$cycloalkyls include, but are not limited to, cyclopropyl and cyclobutyl. In certain embodiments, $R^{12}$ is halo$C_1$-$C_6$alkyl. Suitable halo$C_1$-$C_6$alkyls include but are not limited to, trifluoromethyl.

With regard to the compounds described herein, $R^{13}$ is selected from the group consisting of hydrogen, halogen, OH, $C_1$-$C_6$alkyl, $C_3$-$C_6$cycloalkyl and halo$C_1$-$C_6$alkyl. In certain embodiments, $R^{13}$ is hydrogen. In certain embodiments, $R^{13}$ is halogen. Suitable halogens include, but are not limited to, fluorine, chlorine, bromine and iodine. In certain embodiments, $R^{13}$ is —OH. In certain embodiments, $R^{13}$ is $C_1$-$C_6$alkyl. Suitable $C_1$-$C_6$alkyls include but are not limited to, methyl, ethyl and isopropyl. In certain embodiments, $R^{13}$ is $C_3$-$C_6$cycloalkyl. Suitable $C_3$-$C_6$cycloalkyls include, but are not limited to, cyclopropyl and cyclobutyl. In certain embodiments, $R^{13}$ is halo$C_1$-$C_6$alkyl. Suitable halo$C_1$-$C_6$alkyls include but are not limited to, trifluoromethyl.

With regard to the compounds described herein, $R^{14}$ is selected from the group consisting of hydrogen, halogen, OH, $C_1$-$C_6$alkyl, $C_3$-$C_6$cycloalkyl and halo$C_1$-$C_6$alkyl. In certain embodiments, $R^{14}$ is hydrogen. In certain embodiments, $R^{14}$ is halogen. Suitable halogens include, but are not limited to, fluorine, chlorine, bromine and iodine. In certain embodiments, $R^{14}$ is —OH. In certain embodiments, $R^{14}$ is $C_1$-$C_6$alkyl. Suitable $C_1$-$C_6$alkyls include but are not limited to, methyl, ethyl and isopropyl. In certain embodiments, $R^{14}$ is $C_3$-$C_6$cycloalkyl. Suitable $C_3$-$C_6$cycloalkyls include, but are not limited to, cyclopropyl and cyclobutyl. In certain embodiments, $R^{14}$ is halo$C_1$-$C_6$alkyl. Suitable halo$C_1$-$C_6$alkyls include but are not limited to, trifluoromethyl.

With regard to the compounds described herein, $R^{15}$ is selected from the group consisting of hydrogen, halogen, OH, $C_1$-$C_6$alkyl, and halo$C_1$-$C_6$alkyl. In certain embodiments, $R^{15}$ is hydrogen. In certain embodiments, $R^{15}$ is halogen. Suitable halogens include, but are not limited to, fluorine, chlorine, bromine and iodine. In certain embodiments, $R^{15}$ is —OH. In certain embodiments, $R^{15}$ is $C_1$-$C_6$alkyl. Suitable $C_1$-$C_6$alkyls include but are not limited to, methyl, ethyl and isopropyl. In certain embodiments, $R^{15}$ is halo$C_1$-$C_6$alkyl. Suitable halo$C_1$-$C_6$alkyls include but are not limited to, trifluoromethyl.

With regard to the compounds described herein, $R^{16}$ is selected from the group consisting of hydrogen, halogen, OH, $C_1$-$C_6$alkyl, and halo$C_1$-$C_6$alkyl. In certain embodiments, $R^{16}$ is hydrogen. In certain embodiments, $R^{16}$ is halogen. Suitable halogens include, but are not limited to, fluorine, chlorine, bromine and iodine. In certain embodiments, $R^{16}$ is —OH. In certain embodiments, $R^{16}$ is $C_1$-$C_6$alkyl. Suitable $C_1$-$C_6$alkyls include but are not limited to, methyl, ethyl and isopropyl. In certain embodiments, $R^{16}$ is halo$C_1$-$C_6$alkyl. Suitable halo$C_1$-$C_6$alkyls include but are not limited to, trifluoromethyl.

With regard to the compounds described herein, $R^{17}$ is selected from the group consisting of hydrogen, halogen, $C_1$-$C_6$alkyl, $C_1$-$C_6$alkoxy, and halo$C_1$-$C_6$alkyl. In certain embodiments, $R^{17}$ is hydrogen. In certain embodiments, $R^{17}$ is halogen. Suitable halogens include, but are not limited to, fluorine, chlorine, bromine and iodine. In certain embodiments, $R^{17}$ is $C_1$-$C_6$alkyl. Suitable $C_1$-$C_6$alkyls include but are not limited to, methyl, ethyl and isopropyl. In certain embodiments, $R^{17}$ is $C_1$-$C_6$alkoxy. Suitable $C_1$-$C_6$alkoxys include but are not limited to, methoxy and ethoxy. In certain embodiments, $R^{17}$ is halo$C_1$-$C_6$alkyl. Suitable halo$C_1$-$C_6$alkyls include but are not limited to, trifluoromethyl.

With regard to the compounds described herein, $R^{18}$ is selected from the group consisting of hydrogen, halogen, $C_1$-$C_6$alkyl, $C_3$-$C_6$cycloalkyl, $C_1$-$C_6$alkoxy, $NO^2$, $CONH_2$, halo$C_1$-$C_6$alkyl and $COOC_1$-$C_6$alkyl. In certain embodiments, $R^{18}$ is hydrogen. In certain embodiments, $R^{18}$ is halogen. Suitable halogens include, but are not limited to, fluorine, chlorine, bromine and iodine. In certain embodiments, $R^{18}$ is $C_1$-$C_6$alkyl. Suitable $C_1$-$C_6$alkyls include but are not limited to, methyl, ethyl and isopropyl. In certain embodiments, $R^{18}$ is $C_3$-$C_6$cycloalkyl. Suitable $C_3$-$C_6$cycloalkyls include, but are not limited to, cyclopropyl and cyclobutyl. In certain embodiments, $R^{18}$ is $C_1$-$C_6$alkoxy. Suitable $C_1$-$C_6$alkoxys include but are not limited to, methoxy and ethoxy. In certain embodiments, $R^{18}$ is halo$C_1$-$C_6$alkyl. Suitable halo$C_1$-$C_6$alkyls include but are not limited to, trifluoromethyl. In certain embodiments, $R^{18}$ is $NO^2$. In certain embodiments, $R^{18}$ is $CONH_2$. In certain embodiments, $R^{18}$ is $COOC_1$-$C_6$alkyl. Suitable $COOC_1$-$C_6$alkyls include, but are not limited to, methoxycarbonyl, ethoxycarbonyl, propoxycarbonyl and butoxycarbonyl.

The dashed lines in Formula I indicate the possibility of aromaticity, unsaturation or saturation in the ring depending on the substitution of the ring. In certain embodiments, the compounds of Formula I have the following aromaticity:

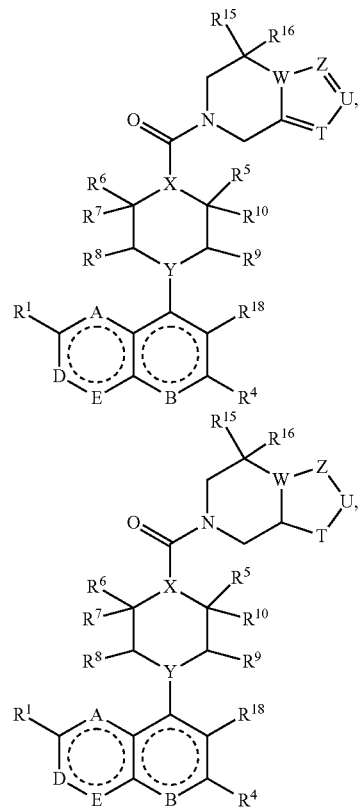

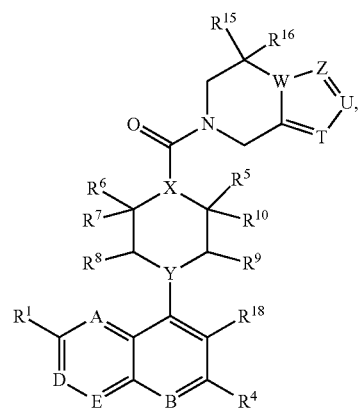

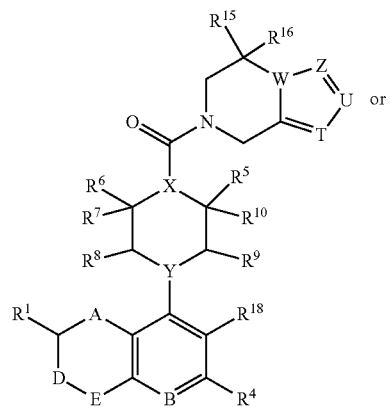

or

-continued
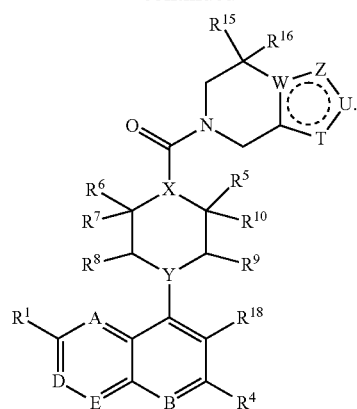
Examples of compounds described herein are as follows:
-continued
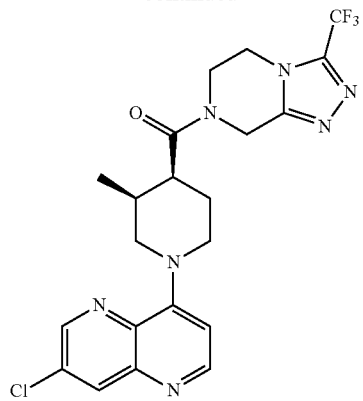

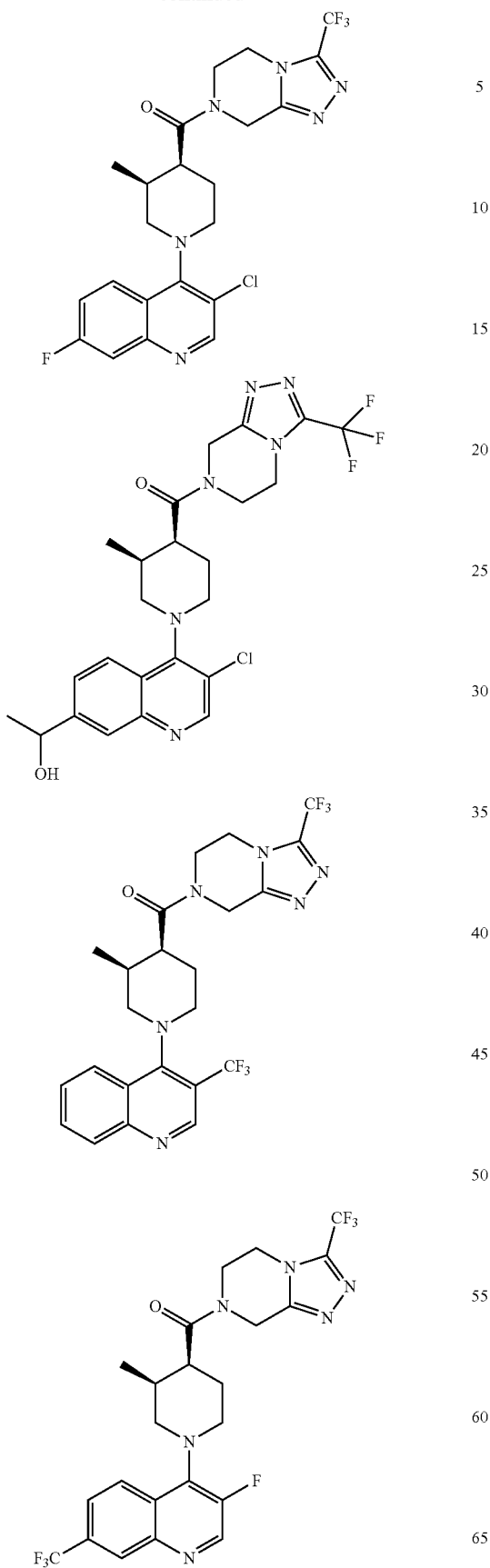
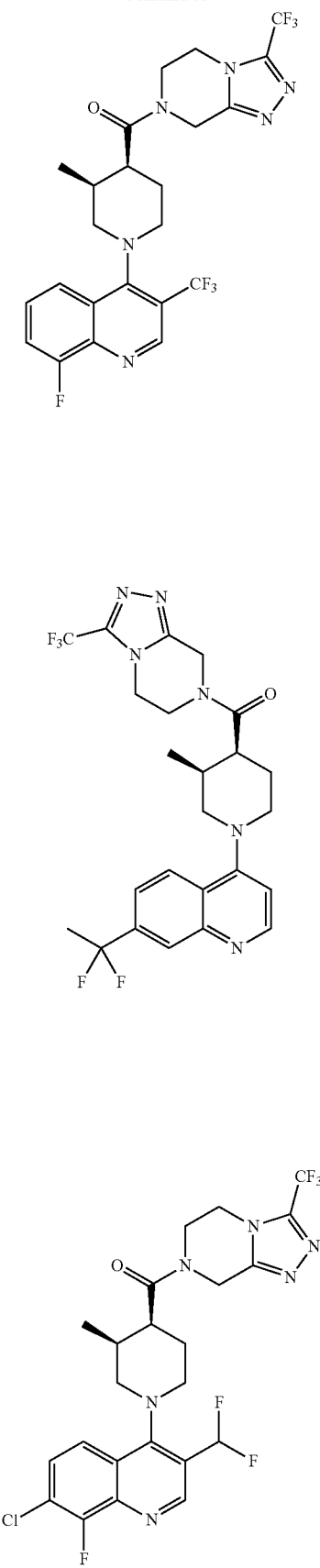

-continued
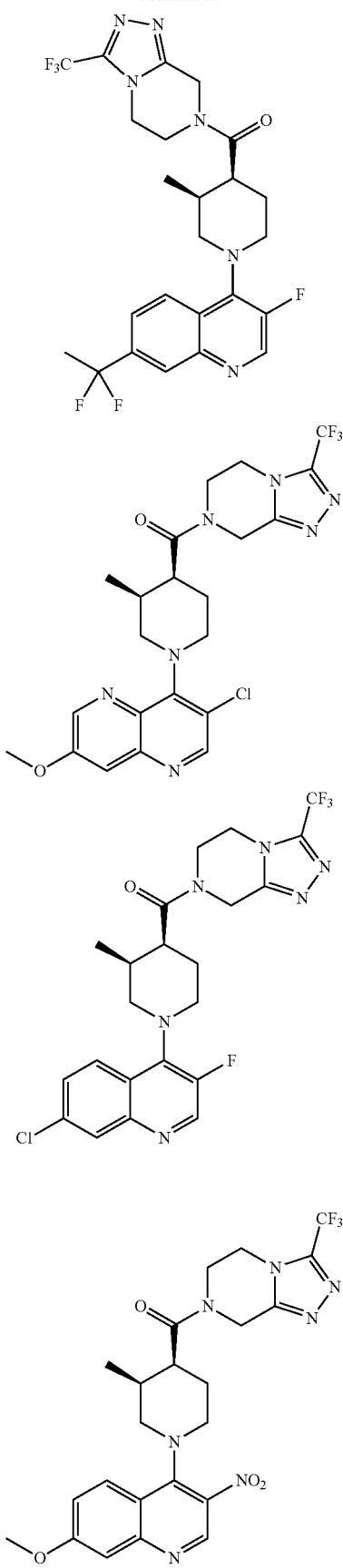
-continued
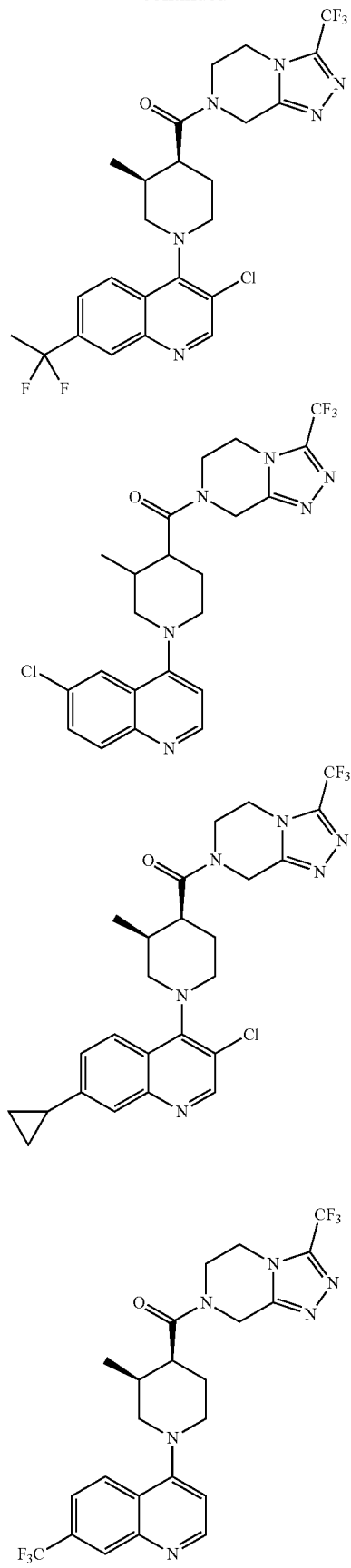

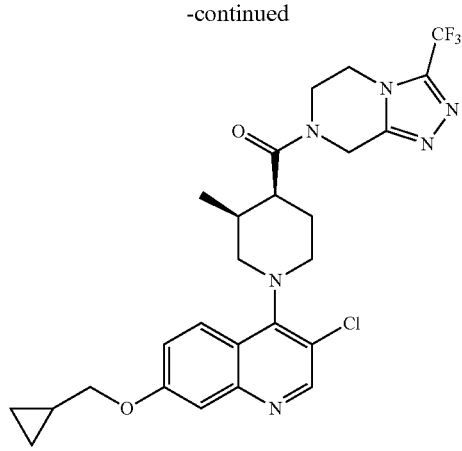
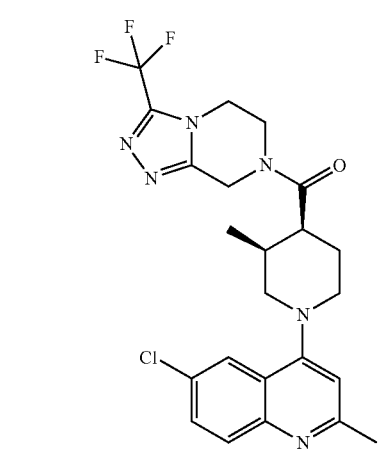
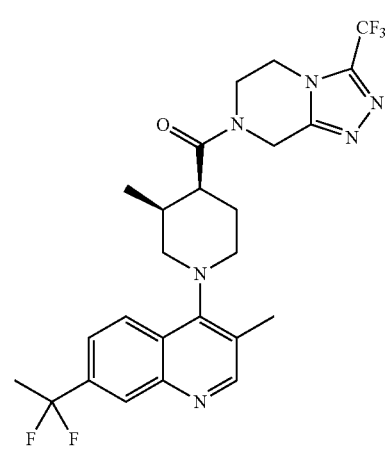
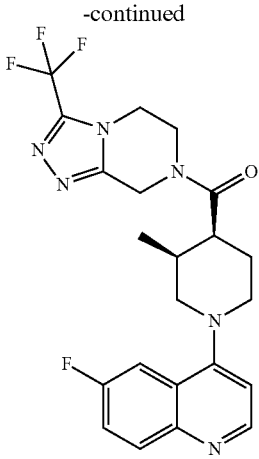
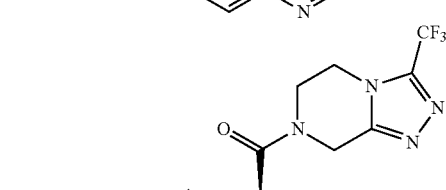
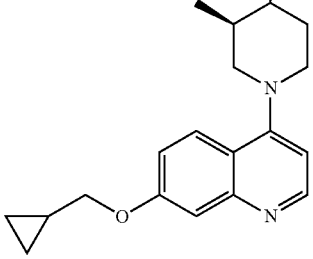
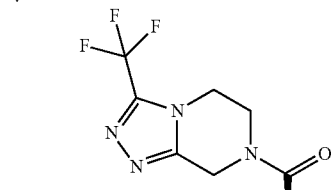
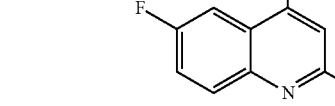
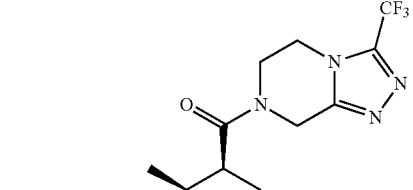
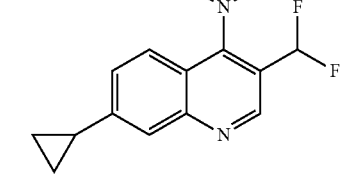

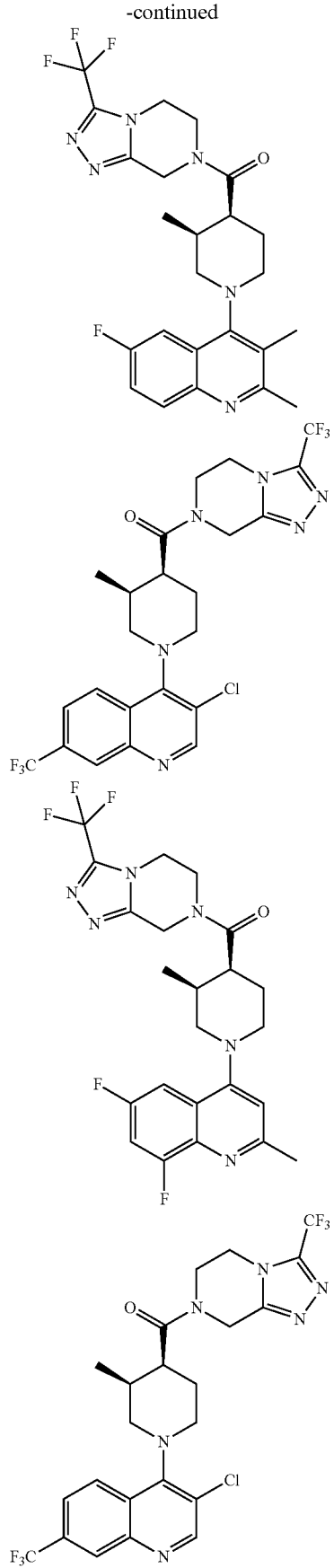
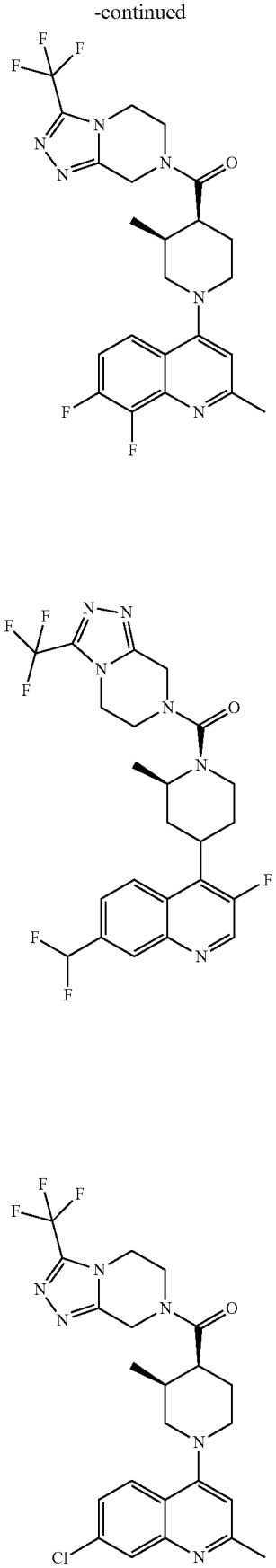

25
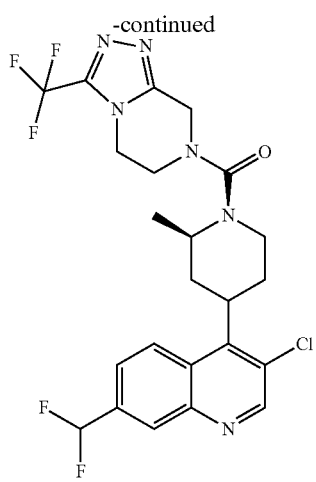
26
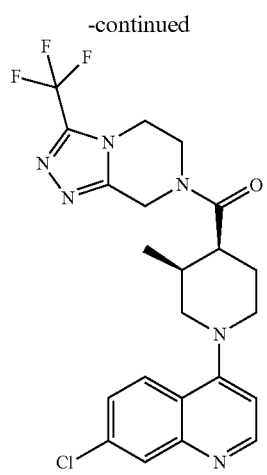
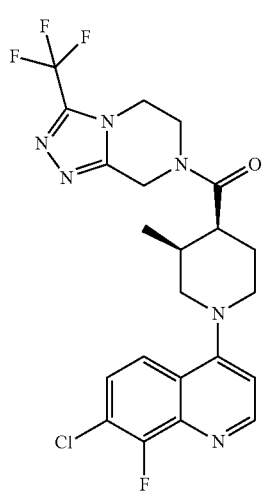
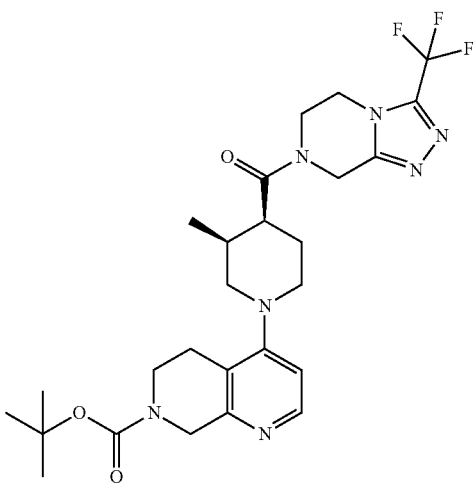
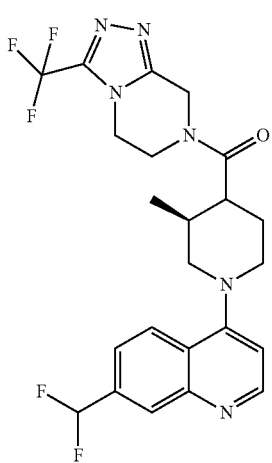
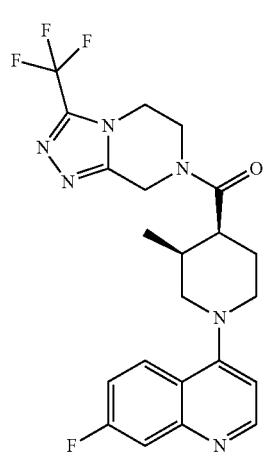

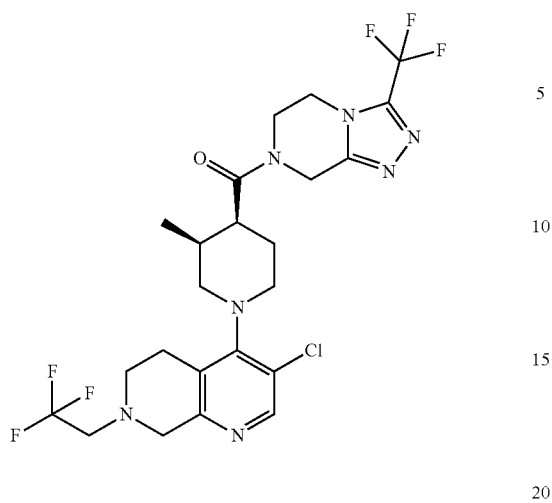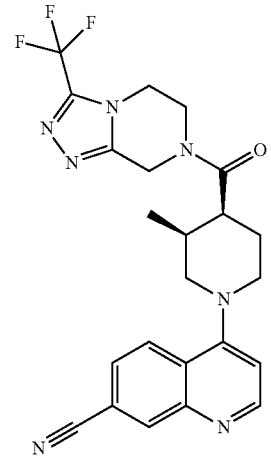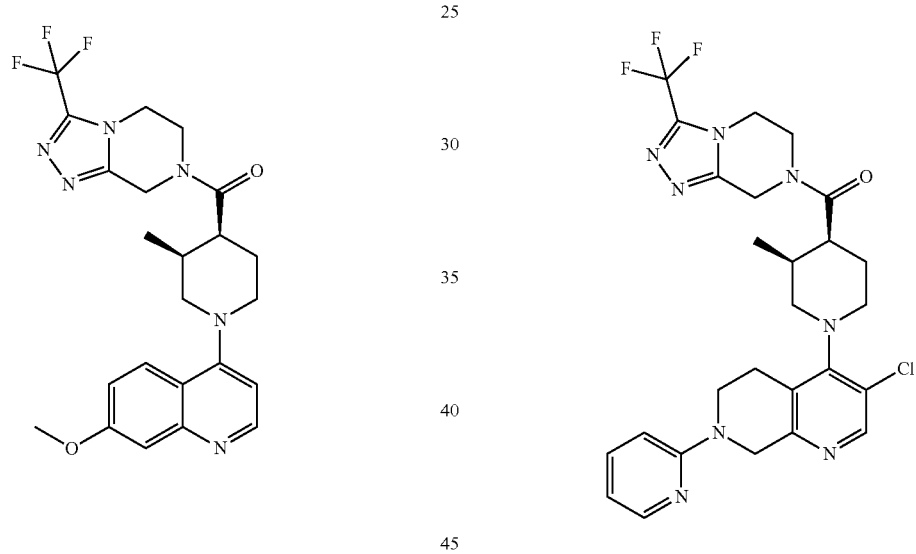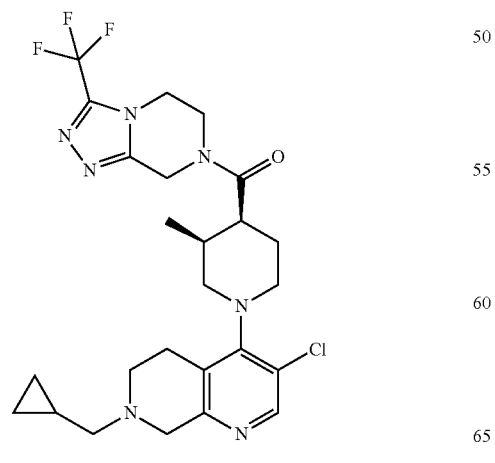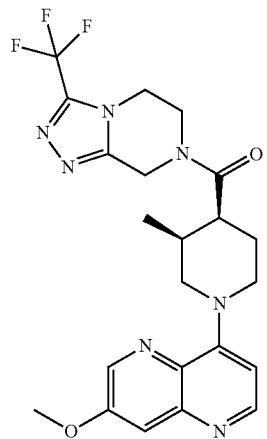

-continued
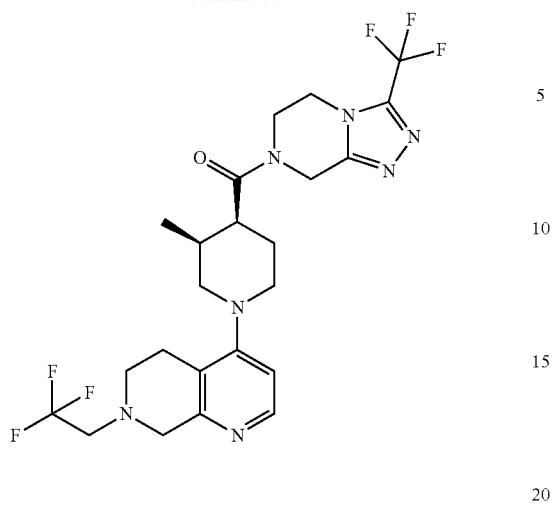
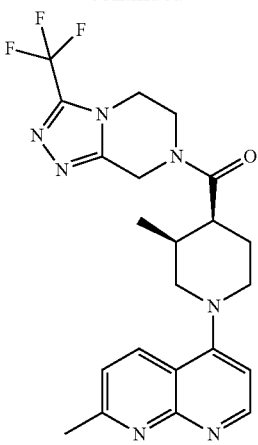
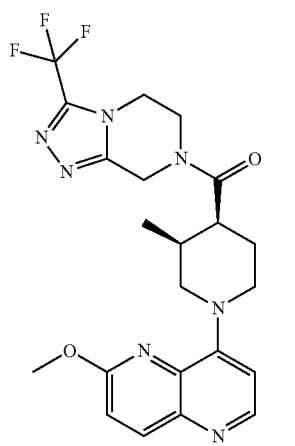
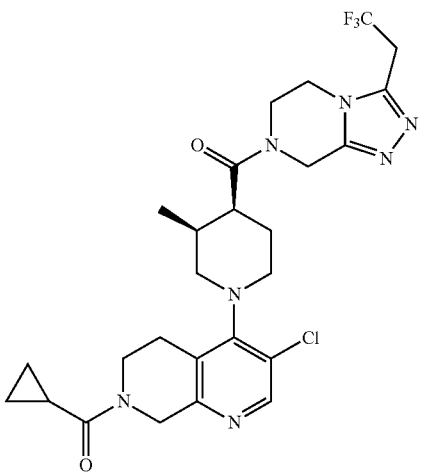
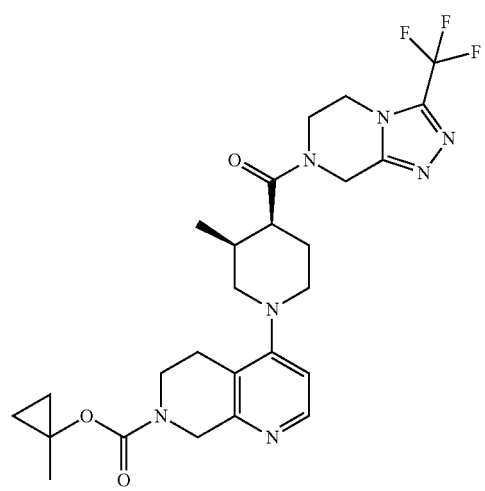
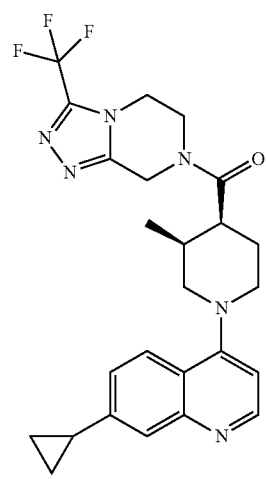

-continued
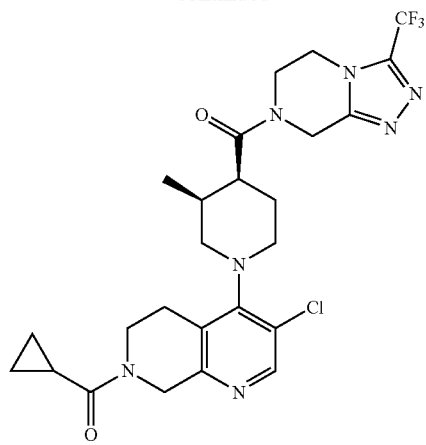
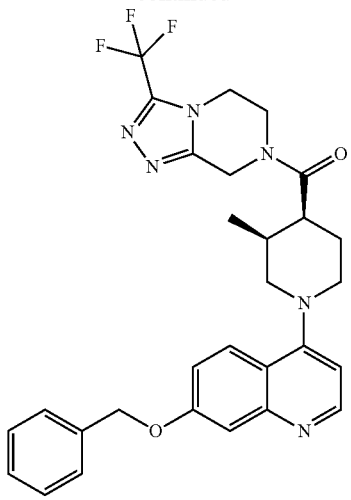
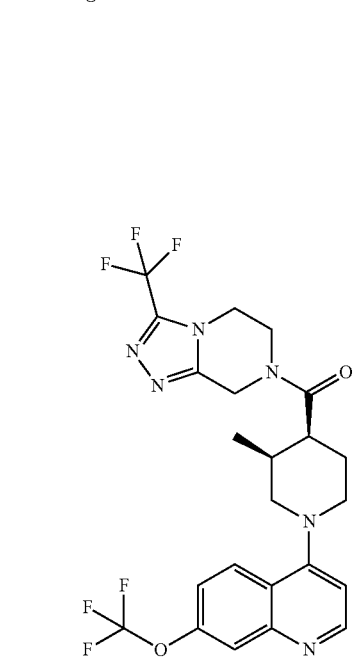
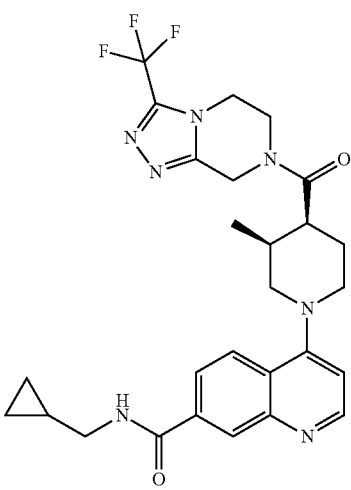
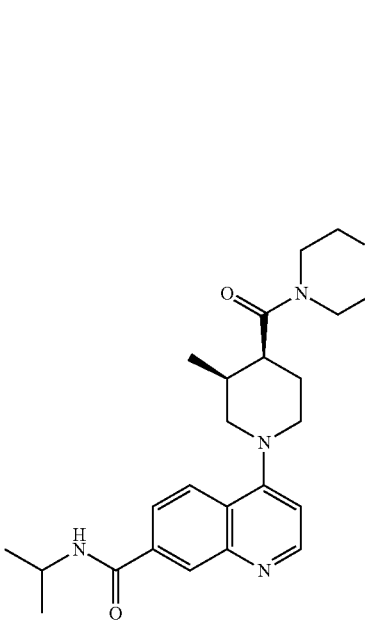
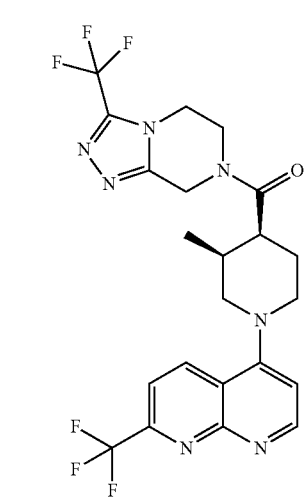

33
-continued
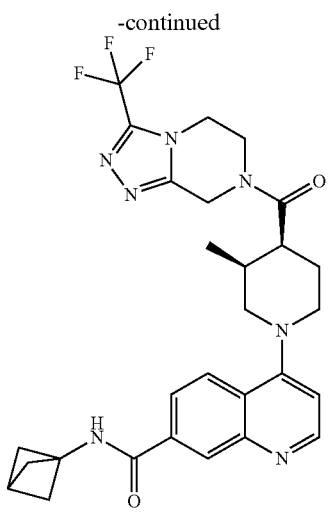
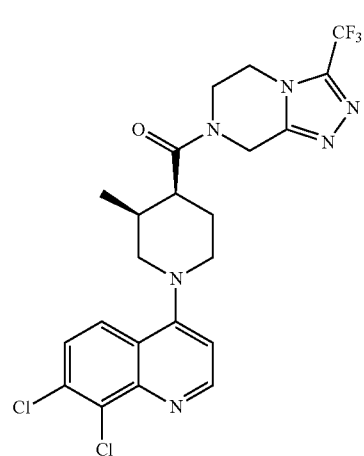
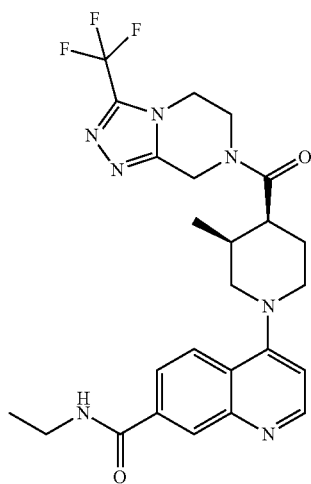
34
-continued
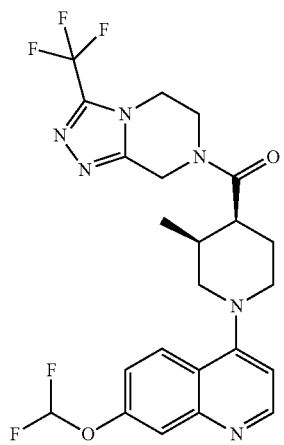
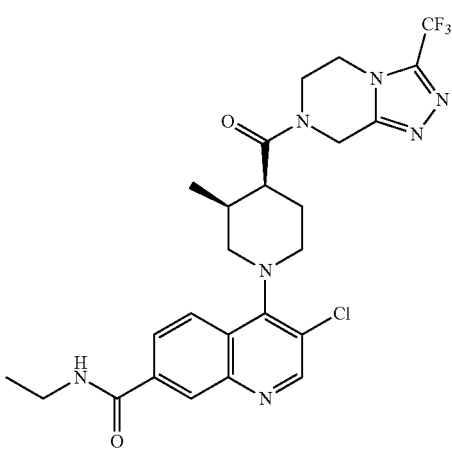
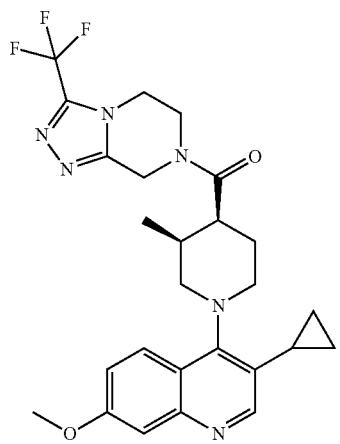

35
-continued

36
-continued

37
-continued
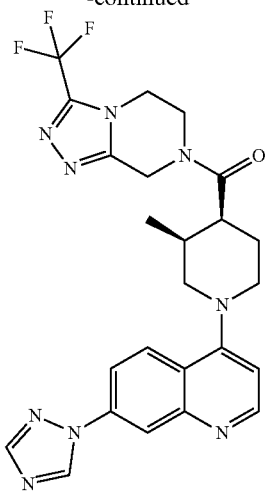
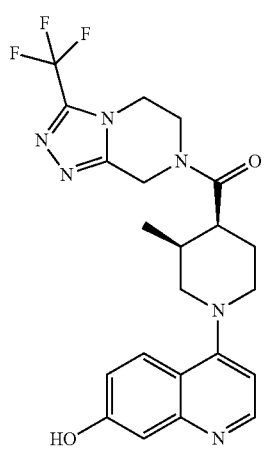
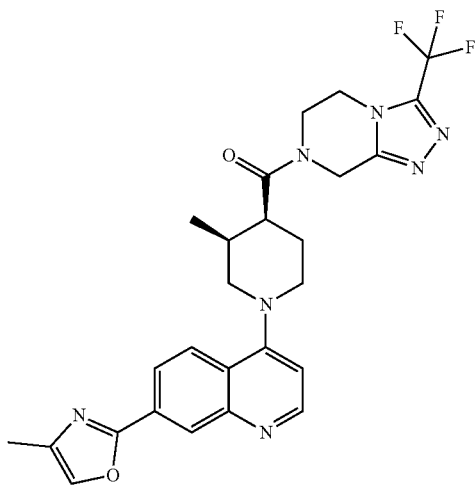
38
-continued
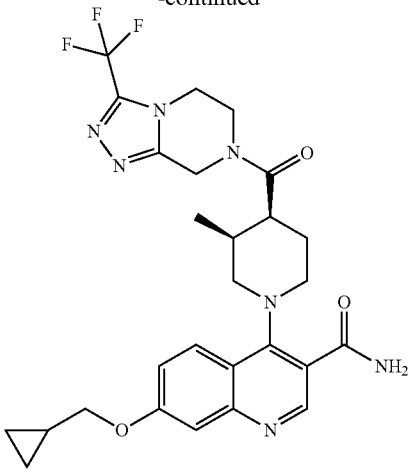
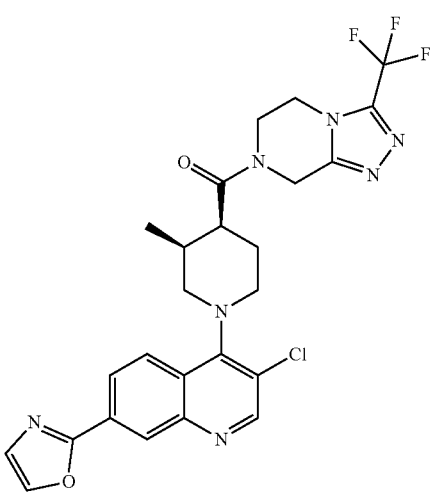
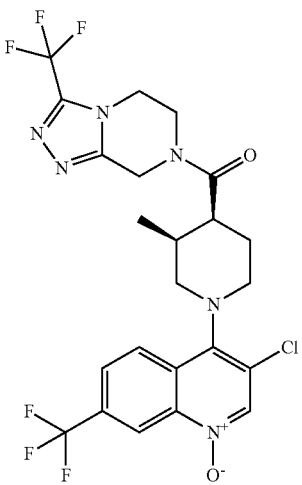

-continued

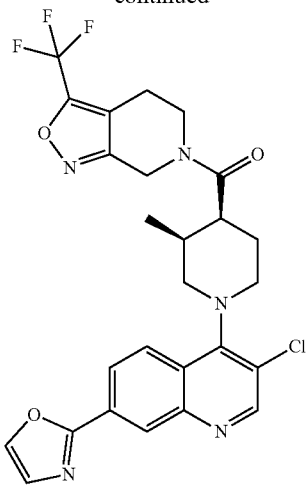
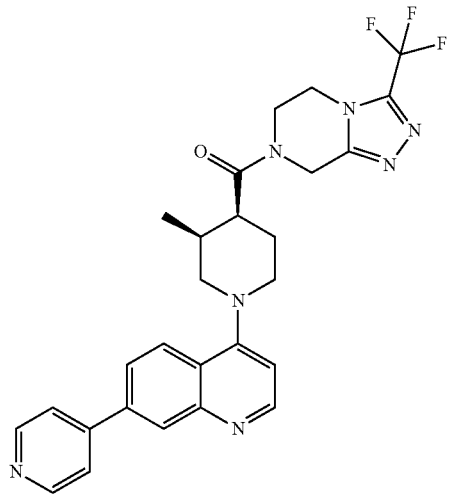
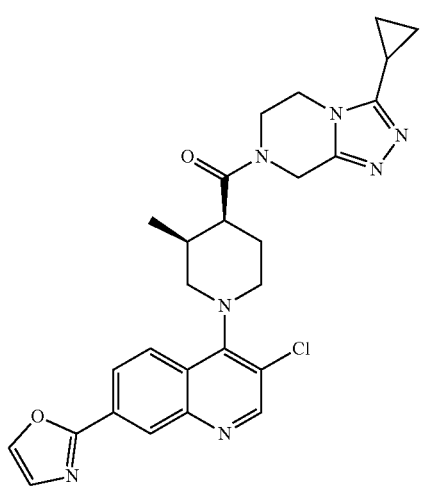

-continued

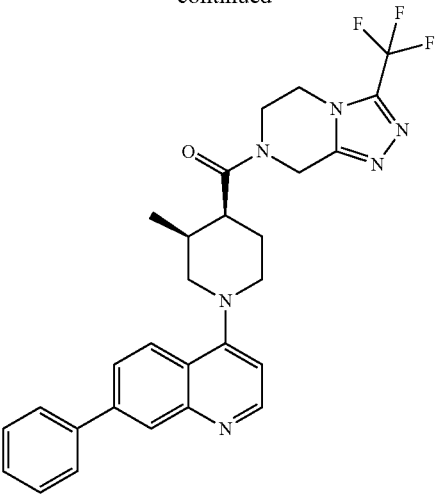

Definitions

The term "halogen" includes a fluorine atom, a chlorine atom, a bromine atom, and an iodine atom.

The term "$C_1$-$C_6$alkyl" encompasses straight alkyl having a carbon number of 1 to 6 and branched alkyl having a carbon number of 3 to 6. Specific examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, and the like.

The term "$C_1$-$C_6$alkoxy" refers to an alkyl group having 1 to 6 carbons linked to oxygen. Examples include methoxy, ethoxy, butoxy and propoxy.

The term "halo$C_1$-$C_6$alkyl" refers to a $C_1$-$C_6$alkyl with the hydrogen atoms thereof being partially or completely substituted with halogen, examples thereof including fluoromethyl, difluoromethyl, trifluoromethyl, 2-fluoroethyl, 1,2-difluoroethyl, 2,2-difluoroethyl and the like.

The term "halo$C_1$-$C_6$alkoxy" refers to —O$C_1$-$C_6$alkyl as defined above, which is substituted with 1-3 halogen atoms which are identical or different, and specifically includes, for example, a trifluoromethoxy group.

The term "—COO$C_1$-$C_6$alkyl" refers to a —COOH group wherein the —OH is replaced with an alkoxy group as defined above. Examples include methoxycarbonyl, ethoxycarbonyl and butoxycarbonyl.

The term "$C_3$-$C_6$cycloalkyl" encompasses bridged, saturated, unsaturated or aromatic cycloalkyls having 3 to 6 carbons. Examples of cycloalkyls include cyclopropyl, cyclobutyl, cyclopentyl, cyclohexyl, bicyclo[1.1.1]pentane, phenyl and the like.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The term "patient" refers to a mammalian patient, preferably a human patient, receiving to receive medical treatment.

The compounds of the present invention contain one or more asymmetric centers and can thus occur as racemates, racemic mixtures, single enantiomers, diastereomeric mixtures, and individual diastereomers. The present invention is meant to comprehend all such isomeric forms of these compounds.

Some of the compounds described herein contain olefinic double bonds, and unless specified otherwise, are meant to include both E and Z geometric isomers.

Some of the compounds described herein contain substituted cycloalkanes having cis- and trans-isomers, and unless specified otherwise, are meant to include both cis- and trans-geometric isomers.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that the present invention encompasses compounds described herein is meant to include the pharmaceutically acceptable salts, and also salts that are not pharmaceutically acceptable when they are used as precursors to the free compounds or their pharmaceutically acceptable salts or in other synthetic manipulations.

Solvates, and in particular, the hydrates of the compounds of the structural formulas described herein are included in the present invention as well.

Some of the compounds described herein may exist as tautomers, which have different points of attachment of hydrogen accompanied by one or more double bond shifts.

For example, a ketone and its enol form are keto-enol tautomers. The individual tautomers as well as mixtures thereof are encompassed with compounds of the present invention.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the Schemes and Examples herein using appropriate isotopically-enriched reagents and/or Intermediates.

Methods of Treatment

Also encompassed by the present invention are methods of treating Cyp8b1-related diseases. The compounds described herein can be effective in preventing or treating various Cyp8b1-related diseases, such as cardiometabolic diseases associated with elevated LDL, such as atherosclerosis, fatty liver and nonalcoholic steatohepatitis (NASH), and noninsulin-dependent diabetes (NIDDM), hyperglycemia, and other symptoms associated with NIDDM. The compounds of the invention can be useful as a preventive or a remedy for noninsulin-dependent diabetes (NIDDM), hyperglycemia, and other symptoms associated with NIDDM.

One aspect of the invention that is of interest relates to a method of treating hyperglycemia, diabetes or insulin resistance in a mammalian patient in need of such treatment which comprises administering to said patient a compound described herein or a pharmaceutically acceptable salt thereof or a pharmaceutical composition comprising the compound or pharmaceutically acceptable salt, in an amount that is effective to treat hyperglycemia, diabetes or insulin resistance.

More particularly, another aspect of the invention that is of interest relates to a method of treating type 2 diabetes in a mammalian patient in need of such treatment comprising administering to the patient a compound described herein or a pharmaceutically acceptable salt thereof or a pharmaceutical composition comprising the compound or pharmaceutically acceptable salt, in an amount that is effective to treat type 2 diabetes.

Yet another aspect of the invention that is of interest relates to a method of treating non-insulin dependent diabetes mellitus in a mammalian patient in need of such treatment comprising administering to the patient a compound described herein or a pharmaceutically acceptable salt thereof or a pharmaceutical composition comprising the compound or pharmaceutically acceptable salt, in an amount that is effective to treat non-insulin dependent diabetes mellitus.

The present invention is also directed to the use of a compound described herein or a pharmaceutically acceptable salt thereof in the manufacture of a medicament for use in treating various CYP8B1-related diseases, such as cardiometabolic diseases associated with elevated LDL, such as atherosclerosis, fatty liver and nonalcoholic steatohepatitis (NASH), and noninsulin-dependent diabetes (NIDDM), hyperglycemia, and other symptoms associated with NIDDM, metabolic diseases such as obesity, diabetes, hormone secretion disorder, hyperlipemia, gout, fatty liver, and the like; circulatory diseases such as angina pectoris, acute/congestive cardiac insufficiency, myocardial infarction, coronary arteriosclerosis, hypertension, nephropathy, electrolyte abnormality, and the like. The compounds described herein may be especially useful as a preventive or a remedy for noninsulin-dependent diabetes (NIDDM), hyperglycemia, and other symptoms associated with NIDDM.

For example, the present invention is directed to the use of a compound described herein or a pharmaceutically acceptable salt thereof in the manufacture of a medicament for use in treating noninsulin-dependent diabetes (NIDDM), hyperglycemia, and other symptoms associated with NIDDM.

Additionally, the present invention is directed to the use of a compound described herein or a pharmaceutically acceptable salt thereof in the manufacture of a medicament for use in treating diabetes.

Additionally, the present invention is directed to the use of a compound described herein or a pharmaceutically acceptable salt thereof in the manufacture of a medicament for use in treating fatty liver and nonalcoholic steatohepatitis (NASH).

Pharmaceutical Compositions

Compounds described herein may be administered orally or parenterally. As formulated into a dosage form suitable for administration, the compounds described herein can be used as a pharmaceutical composition for the prevention, treatment, or remedy of the above diseases.

In clinical use of the compounds described herein, usually, the compound is formulated into various preparations together with pharmaceutically acceptable additives according to the dosage form, and may then be administered. By "pharmaceutically acceptable" it is meant the additive, carrier, diluent or excipient must be compatible with the other ingredients of the formulation and not deleterious to the recipient thereof. As such, various additives ordinarily used in the field of pharmaceutical preparations are usable. Specific examples thereof include gelatin, lactose, sucrose, titanium oxide, starch, crystalline cellulose, hydroxypropyl methylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, hydroxypropyl cyclodextrin, and the like.

Preparations to be formed with those additives include, for example, solid preparations such as tablets, capsules, granules, powders, suppositories; and liquid preparations such as syrups, elixirs, injections. These may be formulated according to conventional methods known in the field of pharmaceutical preparations. The liquid preparations may also be in such a form that may be dissolved or suspended in water or in any other suitable medium in their use. Especially for injections, if desired, the preparations may be dissolved or suspended in physiological saline or glucose liquid, and a buffer or a preservative may be optionally added thereto.

The pharmaceutical compositions may contain the compound of the invention in an amount of from 1 to 99.9% by weight, preferably from 1 to 60% by weight of the composition. The compositions may further contain any other therapeutically-effective compounds.

In case where the compounds of the invention are used for prevention or treatment for the above-mentioned diseases, the dose and the dosing frequency may be varied, depending on the sex, the age, the body weight and the disease condition of the patient and on the type and the range of the intended remedial effect. In general, when orally administered, the dose may be from 0.001 to 50 mg/kg of body weight/day, and it may be administered at a time or in several times. In specific embodiments, the dose is from about 0.01 to about 25 mg/kg/day, in particular embodiments, from about 0.05 to about 10 mg/kg/day. For oral administration, the compositions are preferably provided in the form of tablets or capsules containing from 0.01 mg to 1,000 mg. In specific embodiments, the dose is 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 or 1,000 milligrams of a compound described herein. This dosage regimen may be adjusted to provide the optimal therapeutic response.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds described herein or the other drugs may have utility, where the combination of the drugs together are safer or more effective than either drug alone. Such other drug(s) may be administered in an amount commonly used therefore, contemporaneously or sequentially with a compound described herein or a pharmaceutically acceptable salt thereof. When a compound described herein is used contemporaneously with one or more other drugs, the pharmaceutical composition may in specific embodiments contain such other drugs and the compound described herein or its pharmaceutically acceptable salt in unit dosage form. However, the combination therapy may also include therapies in which the compound described herein or its pharmaceutically acceptable salt and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound described herein or a pharmaceutically acceptable salt thereof.

Examples of other active ingredients that may be administered in combination with a compound of any of the Formulas described herein or a pharmaceutically acceptable salt thereof and either administered separately or in the same pharmaceutical composition, include, but are not limited to:

(1) dipeptidyl peptidase-IV (DPP-4) inhibitors, such as, sitagliptin (disclosed in U.S. Pat. No. 6,699,871), vildagliptin, saxagliptin, alogliptin, denagliptin, carmegliptin, dutogliptin, melogliptin, linagliptin;

(2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), such as those disclosed in WO 02/060388, WO 02/08188, WO 2004/019869, WO 2004/020409, WO 2004/020408, and WO 2004/066963, and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors;

(3) insulin or insulin analogs, such as insulin lispro, insulin detemir, insulin glargine, insulin glulisine, and inhalable formulations of each thereof;

(4) leptin and leptin derivatives and agonists;

(5) amylin and amylin analogs, such as pramlintide;

(6) sulfonylurea and non-sulfonylurea insulin secretagogues, such as tolbutamide, glyburide, glipizide, glimepiride, mitiglinide, and meglitinides, such as nateglinide and repaglinide;

(7) α-glucosidase inhibitors (such as acarbose, voglibose and miglitol);

(8) glucagon receptor antagonists, such as those disclosed in WO 98/04528, WO 99/01423, WO 00/39088, and WO 00/69810;

(9) incretin mimetics, such as GLP-1, GLP-1 analogs, derivatives, and mimetics; and GLP-1 receptor agonists, such as exenatide, liraglutide, taspoglutide, AVE0010, CJC-1131, and BIM-51077, including intranasal, transdermal, and once-weekly formulations thereof;

(10) LDL cholesterol lowering agents such as (i) HMG-CoA reductase inhibitors (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;

(11) HDL-raising drugs, such as niacin or a salt thereof and extended-release versions thereof;

(12) antiobesity compounds such as topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide Y1 or Y5 antagonists (such as MK-0557); CB1 receptor inverse agonists and antagonists (such as rimonabant and taranabant); 33 adrenergic receptor agonists; ghrelin antagonists; bombesin receptor agonists (such as bombesin receptor subtype-3 agonists); and 5-hydroxytryptamine-2c (5-HT2c) agonists, such as lorcaserin;

(13) agents intended for use in inflammatory conditions, such as aspirin, non-steroidal anti-inflammatory drugs (NSAIDs), glucocorticoids, and selective cyclooxygenase-2 (COX-2) inhibitors;

(14) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers (such as and calcium channel blockers (such as;

(15) glucokinase activators (GKAs), such as LY2599506;

(16) inhibitors of 11β-hydroxysteroid dehydrogenase type 1, such as those disclosed in U.S. Pat. No. 6,730,690; WO 03/104207; and WO 04/058741;

(17) inhibitors of cholesteryl ester transfer protein (CETP), such as torcetrapib and MK-0859;

(18) inhibitors of fructose 1,6-bisphosphatase, such as those disclosed in U.S. Pat. Nos. 6,054,587; 6,110,903; 6,284,748; 6,399,782; and 6,489,476;

(19) inhibitors of acetyl CoA carboxylase-1 or 2 (ACC1 or ACC2);

(20) AMP-activated Protein Kinase (AMPK) activators;

(21) agonists of the G-protein-coupled receptors: GPR-109, GPR-119, and GPR-40;

(22) SSTR3 antagonists, such as those disclosed in WO 2009/011836;

(23) neuromedin U receptor agonists, such as those disclosed in WO2009/042053, including, but not limited to, neuromedin S (NMS);

(24) inhibitors of stearoyl-coenzyme A delta-9 desaturase (SCD);

(25) GPR-105 antagonists, such as those disclosed in WO 2009/000087;

(26) inhibitors of glucose uptake, such as sodium-glucose transporter (SGLT) inhibitors and its various isoforms, such as SGLT-1; SGLT-2, such as dapagliflozin, canagliflozin, ertugliflozin, empagliflozin, ipragliflozin and remogliflozin; and SGLT-3;

(27) inhibitors of acyl coenzyme A:diacylglycerol acyltransferase 1 and 2 (DGAT-1 and DGAT-2);

(28) inhibitors of fatty acid synthase;

(29) inhibitors of acetyl-CoA carboxylase-1 and 2 (ACC-1 and ACC-2);

(30) inhibitors of acyl coenzyme A:monoacylglycerol acyltransferase 1 and 2 (MGAT-1 and MGAT-2);

(31) agonists of the TGR5 receptor (also known as GPBAR1, BG37, GPCR19, GPR131, and M-BAR); and

(32) bromocriptine mesylate and rapid-release formulations thereof.

In another aspect of the invention, a pharmaceutical composition is disclosed which comprises:

(a) a compound described herein or a pharmaceutically acceptable salt thereof;

(b) one or more compounds selected from the group consisting of:
(1) dipeptidyl peptidase-IV (DPP-4) inhibitors;
(2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors;
(3) sulfonylurea and non-sulfonylurea insulin secretagogues, such as tolbutamide, glyburide, glipizide, glimepiride, mitiglinide, and meglitinides, such as nateglinide and repaglinide;
(4) α-glucosidase inhibitors (such as acarbose, voglibose and miglitol);
(5) glucagon receptor antagonists;
(6) LDL cholesterol lowering agents such as (i) HMG-CoA reductase inhibitors (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;
(7) HDL-raising drugs, such as niacin or a salt thereof and extended-release versions thereof;
(8) antiobesity compounds;
(9) agents intended for use in inflammatory conditions, such as aspirin, non-steroidal anti-inflammatory drugs (NSAIDs), glucocorticoids, and selective cyclooxygenase-2 (COX-2) inhibitors;
(10) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers and calcium channel blockers;
(11) glucokinase activators (GKAs), such as LY2599506;
(12) inhibitors of 11β-hydroxysteroid dehydrogenase type 1;
(13) inhibitors of cholesteryl ester transfer protein (CETP), such as torcetrapib and MK-0859;
(14) inhibitors of fructose 1,6-bisphosphatase;
(15) inhibitors of acetyl CoA carboxylase-1 or 2 (ACC1 or ACC2);
(16) AMP-activated Protein Kinase (AMPK) activators;
(17) agonists of the G-protein-coupled receptors: GPR-109, GPR-119, and GPR-40;
(18) SSTR3 antagonists;
(19) neuromedin U receptor agonists, including, but not limited to, neuromedin S (NMS);
(20) inhibitors of stearoyl-coenzyme A delta-9 desaturase (SCD);
(21) GPR-105 antagonists;
(22) inhibitors of glucose uptake, such as sodium-glucose transporter (SGLT) inhibitors and its various isoforms, such as SGLT-1; SGLT-2, such as dapagliflozin, canagliflozin, ertugliflozin, empagliflozin, ipragliflozin and remogliflozin; and SGLT-3;
(23) inhibitors of acyl coenzyme A:diacylglycerol acyltransferase 1 and 2 (DGAT-1 and DGAT-2);
(24) inhibitors of fatty acid synthase;
(25) inhibitors of acetyl-CoA carboxylase-1 and 2 (ACC-1 and ACC-2);
(26) inhibitors of acyl coenzyme A:monoacylglycerol acyltransferase 1 and 2 (MGAT-1 and MGAT-2);
(27) agonists of the TGR5 receptor (also known as GPBAR1, BG37, GPCR19, GPR131, and M-BAR); and
(28) bromocriptine mesylate and rapid-release formulations thereof; and
(c) a pharmaceutically acceptable carrier.

When a compound of the present invention is used contemporaneously with one or more other drugs a specific embodiment hereof pertains to, a pharmaceutical composition containing such other drugs in addition to the compound of the present invention. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, in particular embodiments from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

EXAMPLES

The meanings of the abbreviations in Examples are shown below.
ACN=MeCN=acetonitrile
BAST=bis-(2-methoxyethyl)aminosulfur trifluoride
CELITE=diatomaceous earth
Conc.=concentrated
CuI=Copper(I) iodide
$Cs_2CO_3$=Cesium carbonate
DAST—diethylaminosulfurtrifluoride
DCM=dichloromethane
DEA=diethylamine
DIBALH=diisobutylaluminum hydride
DIEA=DIPEA=N,N-Diisopropylethylamine
DMA=Dimethylacetamide
DMAP=4-dimethylaminopyridine
DMF=N,N-Dimethylformamide
DMSO=Dimethyl sulfoxide
DOWNTHERM A=a eutectic mixture of 26% diphenyl and 74% diphenyl ether DTBPFPdCl$_2$=[1,1'-Bis(di-tert-butylphosphino)ferrocene]dichloropalladium(II)
ee=enantiomeric excess
Et$_2$O=diethyl ether
EtOAc=ethyl acetate
EtOH=ethanol Me=methyl
h=hours
HATU=(1-[Bis(dimethylamino)methylene]-1H-1,2,3-triazolo[4,5-b]pyridinium 3-oxid hexafluorophosphate)
HOAt=1-Hydroxy-7-azabenzotriazole
HCl=hydrochloric acid
HOBt=hydroxybenzotriazole
IPA=isopropyl alcohol
K$_2$CO$_3$=potassium carbonate
K$_3$PO$_4$=Tripotassium phosphate
LCMS=Liquid chromatography-mass spectrometry
LDA=Lithium diisopropylamide
LDH=lactic acid dehydrogenase
LHMDS=LiHMDS=lithium bis(trimethylsilyl)amide
LiOH=lithium hydroxide
mCPBA=meta-Chloroperoxybenzoic acid
min=minutes
MeOH=methanol
MgSO$_4$=magnesium sulfate
MPLC=medium pressure liquid chromatography
NaHCO$_3$=sodium bicarbonate
NaSO$_3$=sodium sulfite
Na$_2$SO$_4$=sodium sulfate
NCS=N-chlorosuccinimide
NH$_4$Cl=Ammonium chloride
NH$_4$OH=Ammonium hydroxide
NMP=N-methyl-2-pyrrolidone
PdCl$_2$(dppf)-CH$_2$Cl$_2$=[1,1'-Bis(diphenylphosphino)ferrocene]dichloropalladium(II)
PCl$_5$=Phosphorus pentachloride
P-HPLC or prep-HPLC=preparative high performance liquid chromatography
POCl$_3$=Phosphorus oxychloride
P-TLC=preparative thin layer chromatography
Py=pyridine
RT=room temperature
SFC=Supercritical Fluid Chromatography
TEA=triethylamine
TFA=trifluoroacetic acid
THF=tetrahydrofuran
TLC=thin layer chromatography
TMS=Trimethylsilyl
Xantphos=4,5-Bis(diphenylphosphino)-9,9-dimethylxanthene
CDCl$_3$=heavy chloroform
CD$_3$OD=heavy methanol
DMSO=dimethylsulfoxide The meanings of the abbreviations in the nuclear magnetic resonance spectra are shown below:
s=singlet, d=doublet, dd=double doublet, dt=double triplet, ddd=double double doublet, Sept=septet, t=triplet, m=multiplet, br=broad, brs=broad singlet, q=quartet J=coupling constant and Hz=hertz.

Compounds of this invention can be prepared using the Intermediates and processes outlined below. The various starting materials used are commercially available or are readily made by persons skilled in the art.

Intermediates

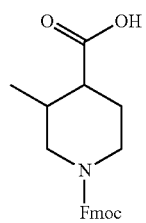

Intermediate 1

1-[(9H-fluoren-9-ylmethoxy)carbonyl]-3-methylpiperidine-4-carboxylic acid 1-(tert-butoxycarbonyl)-3-methylpiperidine-4-carboxylic acid (15.0 g, 61.7 mmol) was combined with DCM (308 mL) and TFA (15.90 mL, 206 mmol) and stirred at room temperature for 15 h. The mixture was concentrated and the reaction was diluted with 1,4-dioxane (400 mL). Sodium carbonate (2.1M in water, 294 mL, 617 mmol) was added to the reaction mixture and the reaction was placed under an overhead stirrer. (9H-fluoren-9-yl)methyl carbonochloridate (16.0 g, 61.7 mmol) was added to the reaction mixture and the reaction was stirred at room temperature for 15 h. The reaction was diluted with water and extracted with EtOAc (1×). The aqueous layer was then acidified to pH 2 with 1N HCl. EtOAc was added and the aqueous layer was extracted with EtOAc (2×). The residue was purified by column chromatography (0-70% 3:1 EtOAc:EtOH in Hexanes) to afford the title compound. MS: 366 (M+1).

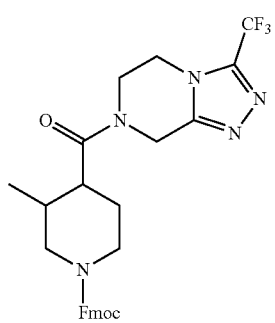

Intermediate 2

9H-fluoren-9-ylmethyl 3-methyl-4-{[3-(trifluoromethyl)-5,6-dihydro[1,2,4]triazolo[4,3-a]pyrazin-7(8H)-yl]carbonyl}piperidine-1-carboxylate A mixture of HATU (23.1 g, 60.8 mmol), 3-(trifluoromethyl)-5,6,7,8-tetrahydro-[1,2,4]triazolo[4,3-a]pyrazin-7-ium chloride (11.75 g, 51.4 mmol) and 1-(((9H-fluoren-9-yl)methoxy)carbonyl)-3-methylpiperidine-4-carboxylic acid (17.08 g, 46.7 mmol) was flushed with nitrogen gas three times and anhydrous DMF (160 mL) was added, followed by DIPEA (24.42 mL, 140 mmol). The mixture was stirred at room temperature overnight. Water was added to the reaction and the combined fractions were extracted with EtOAc (3×). The combined organic layers were dried with magnesium sulfate, filtered, and concentrated. The residue was purified by silica gel chromatography (0-100% 3:1 EtOAc:EtOH in Hexane). The fractions were combined and concentrated to give a clear oil. MS: 540 (M+1).

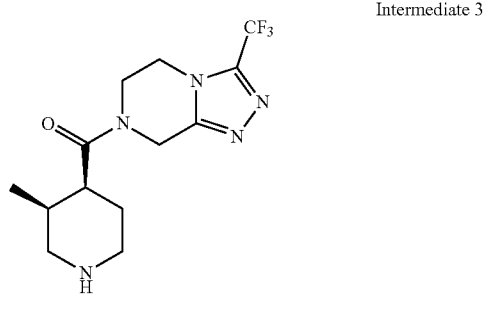 [SMILES: C[C@@H]1CNCC[C@@H]1C(=O)N1CCn2c(nnc2C(F)(F)F)C1]

Intermediate 3

[(3S,4S)-3-methylpiperidin-4-yl][3-(trifluoromethyl)-5,6-dihydro[1,2,4]triazolo[4,3-a]pyrazin-7(8H)-yl]methanone 9H-fluoren-9-ylmethyl 3-methyl-4-{[3-(trifluoromethyl)-5,6-dihydro[1,2,4]triazolo[4,3-a]pyrazin-7(8H)-yl]carbonyl}piperidine-1-carboxylate (17.29 g, 32.0 mmol) was separated (Column: IC (2×15 cm), injection volume 0.8 mL at 30 mg/mL in 3:1 MeOH:DCM, wavelength 220 nm, 30% MeOH (0.1% NH$_4$OH)/CO$_2$ at 100 bar). The single diastereomers were analyzed at 99% ee before drying down. DCM (156 mL) and MeOH (67 mL) was added to major peak 1. Piperidine (5.51 mL, 55.6 mmol) was added and the reaction was stirred for 15 h at room temperature. The slurry was directly concentrated and purified by silica gel chromatography (0-10% MeOH in DCM w/0.1% NH$_4$OH, then 20% MeOH in DCM w/0.1% NH$_4$OH isocratic). The fractions were combined and concentrated to give the title compound.

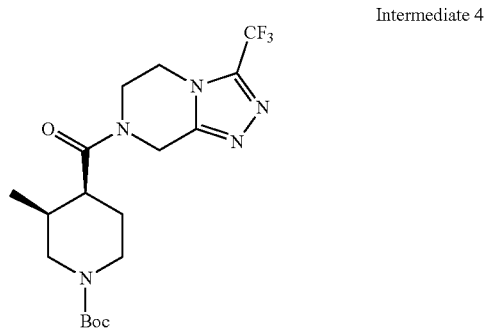 [SMILES: C[C@@H]1CN(C(=O)OC(C)(C)C)CC[C@@H]1C(=O)N1CCn2c(nnc2C(F)(F)F)C1]

Intermediate 4 tert-butyl (3S,4S)-3-methyl-4-{[3-(trifluoromethyl)-5,6-dihydro[1,2,4]triazolo[4,3-a]pyrazin-7(8H)-yl]carbonyl}piperidine-1-carboxylate ((3S,4S)-3-methylpiperidin-4-yl)(3-(trifluoromethyl)-5,6-dihydro-[1,2,4]triazolo[4,3-a]pyrazin-7(8H)-yl)methanone (2.25 g, 7.09 mmol) was dissolved in DCM (35.5 mL). Boc-anhydride (2.32 g, 10.6 mmol) was added followed by DIPEA (2.48 mL, 14.2 mmol) and the mixture was left to stir for 8 h. Water was added to the reaction and the combined fractions were extracted with EtOAc 2×. The combined organic layers were dried with magnesium sulfate, filtered, and concentrated. The residue was purified by silica gel chromatography (0-100% 3:1 EtOAc:EtOH in Hex). The fractions were combined and concentrated to give the title compound. MS: 418 (M+1).

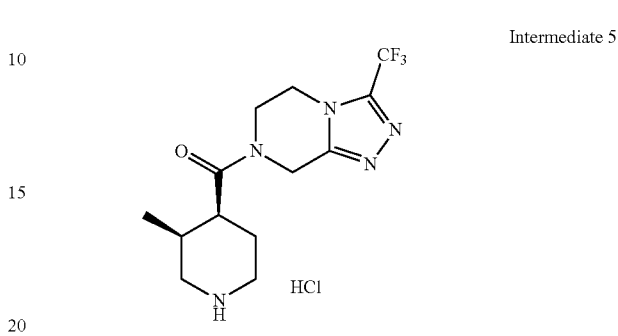

Intermediate 5

[(3S,4S)-3-methylpiperidin-4-yl][3-(trifluoromethyl)-5,6-dihydro[1,2,4]triazolo[4,3-a]pyrazin-7(8H)-yl]methanone hydrochloride HCl (1M in dioxane, 8.26 mL, 33.1 mmol) was added to a mixture of tert-butyl (3S,4S)-3-methyl-4-{[3-(trifluoromethyl)-5,6-dihydro[1,2,4]triazolo[4,3-a]pyrazin-7(8H)-yl]carbonyl}piperidine-1-carboxylate (2.76 g, 6.61 mmol) in DCM (33 mL). The mixture was stirred for 12 h at room temperature, then was concentrated and dried under vacuum to provide the title compound.

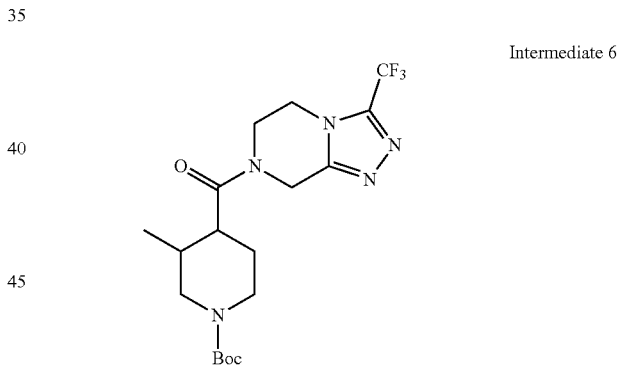

Intermediate 6 tert-butyl 3-methyl-4-(3-(trifluoromethyl)-5,6,7,8-tetrahydro-[1,2,4]triazolo[4,3-a]pyrazine-7-carbonyl)piperidine-1-carboxylate DIPEA (6.00 g, 15.78 mmol) was added to a mixture of 3-(trifluoromethyl)-5,6,7,8-tetrahydro-[1,2,4]triazolo[4,3-a]pyrazine hydrochloride (2.26 g, 9.86 mmol), 1-(tert-butoxycarbonyl)-3-methylpiperidine-4-carboxylic acid (2.4 g, 9.86 mmol) and HATU in DMF (50 mL) (6.89 mL, 39.5 mmol) in DMF (50 mL). The mixture was stirred at 25° C. for 23 h. The reaction was quenched with water (100 mL) and extracted with EtOAc (60 mL×4). The combined organic phases were washed with brine (50 mL), dried over Na$_2$SO$_4$, filtered and concentrated. The residue was purified by silica gel chromatography (PE:EtOAc=2: 1-1:2, added 0.5% NH$_4$OH) to give tert-butyl 3-methyl-4-(3-(trifluoromethyl)-

5,6,7,8-tetrahydro-[1,2,4]triazolo[4,3-a]pyrazine-7-carbonyl)piperidine-1-carboxylate. MS: 418 (M+1).

Intermediates 6a and 6b

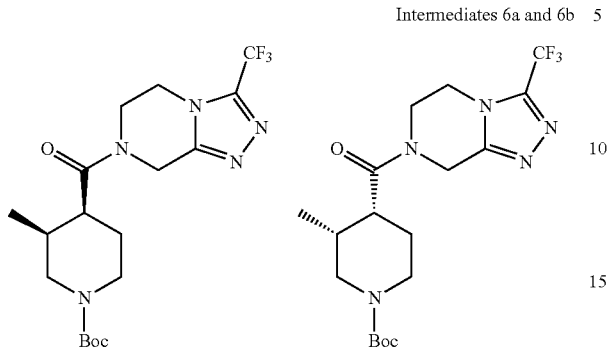

(3S,4S)-tert-butyl 3-methyl-4-(3-(trifluoromethyl)-5,6,7,8-tetrahydro-[1,2,4]triazolo[4,3-a]pyrazine-7-carbonyl)piperidine-1-carboxylate (3R,4R)-tert-butyl 3-methyl-4-(3-(trifluoromethyl)-5,6,7,8-tetrahydro-[1,2,4]triazolo[4,3-a]pyrazine-7-carbonyl)piperidine-1-carboxylate Tert-butyl 3-methyl-4-(3-(trifluoromethyl)-5,6,7,8-tetrahydro-[1,2,4]triazolo[4,3-a]pyrazine-7-carbonyl)piperidine-1-carboxylate (3.6 g, 8.62 mmol) was resolved by supercritical fluid chromatography (Column: Chiralpak AD-3 Mobile phase: A: $CO_2$ B: Methanol (0.05% DEA); Gradient: from 5% to 40% of B.) to give (3R,4R)-tert-butyl 3-methyl-4-(3-(trifluoromethyl)-5,6,7,8-tetrahydro-[1,2,4]triazolo[4,3-a]pyrazine-7-carbonyl)piperidine-1-carboxylate (peak 2, SFC $t_R$=2.36 min) MS: 418 (M+1) and (3S,4S)-tert-butyl 3-methyl-4-(3-(trifluoromethyl)-5,6,7,8-tetrahydro-[1,2,4]triazolo[4,3-a]pyrazine-7-carbonyl)piperidine-1-carboxylate (peak 3, SFC $t_R$=2.64 min). MS: 418 (M+1).

Intermediate 7

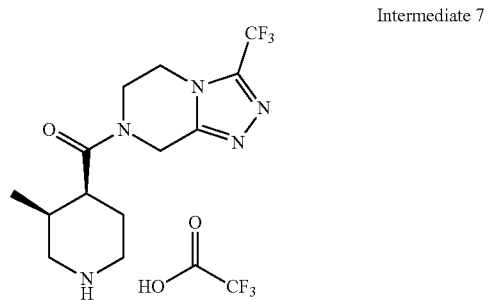

[(3S,4S)-3-methylpiperidin-4-yl][3-(trifluoromethyl)-5,6-dihydro[1,2,4]triazolo[4,3-a]pyrazin-7(8H)-yl]methanone trifluoroacetate TFA (3 mL, 38.9 mmol) was added to a mixture of (3S,4S)-tert-butyl 3-methyl-4-(3-(trifluoromethyl)-5,6,7,8-tetrahydro-[1,2,4]triazolo[4,3-a]pyrazine-7-carbonyl)piperidine-1-carboxylate (1.1 g, 2.64 mmol) in DCM (9 mL) at 0° C. The reaction mixture was stirred at 25° C. for 2 h. The reaction was concentrated and dried under reduced pressure to provide the title compound. MS: 318 (M+1).

Intermediate 8

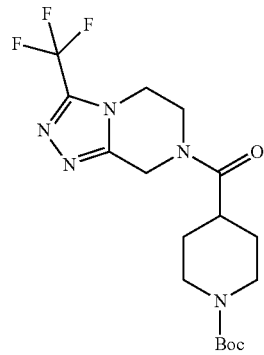

tert-butyl 4-(3-(trifluoromethyl)-5,6,7,8-tetrahydro-[1,2,4]triazolo[4,3-a]pyrazine-7-carbonyl)piperidine-1-carboxylate A mixture of HATU (6.47 g, 17.0 mmol), 3-(trifluoromethyl)-5,6,7,8-tetrahydro-[1,2,4]triazolo[4,3-a]pyrazin-7-ium chloride (3.29 g, 14.4 mmol) and 1-(tert-butoxycarbonyl)piperidine-4-carboxylic acid (3.0 g, 13.1 mmol) was flushed with nitrogen gas three times and anhydrous DMF (26.2 mL) was added, followed by DIPEA (6.84 mL, 39.3 mmol). The mixture was stirred at room temperature overnight. Water was added to the reaction mixture and the combined fractions were extracted 3× with EtOAc. The combined organic layers were dried with magnesium sulfate, filtered, and concentrated. The residue was purified by silica gel chromatography (0-60% 3:1 EtOAc:EtOH in Hexanes). The fractions were combined and concentrated to give the title compound. MS: 404 (M+1).

Intermediate 9

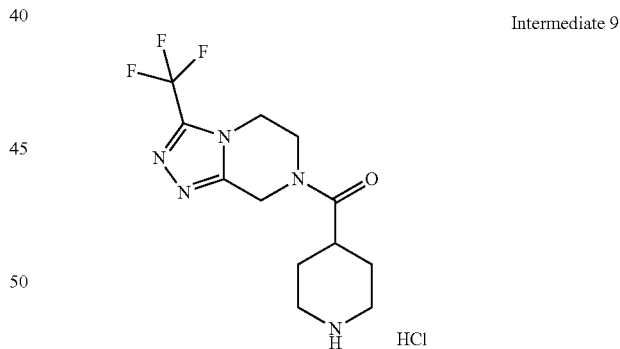

piperidin-4-yl[3-(trifluoromethyl)-5,6-dihydro[1,2,4]triazolo[4,3-a]pyrazin-7(8H)-yl]methanone hydrochloride HCl in dioxane (14.13 mL, 56.5 mmol) was added to a mixture of tert-butyl 4-(3-(trifluoromethyl)-5,6,7,8-tetrahydro-[1,2,4]triazolo[4,3-a]pyrazine-7-carbonyl)piperidine-1-carboxylate (4.56 g, 11.30 mmol) in MeOH (56.5 mL). The mixture was stirred for 12 h at room temperature, then was concentrated and dried under vacuum to provide the title compound.

Intermediate 10

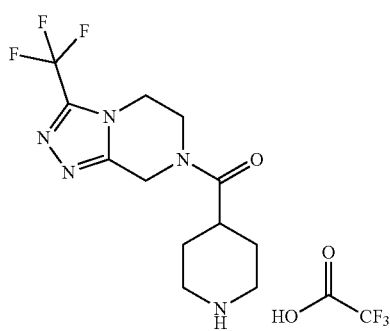

piperidin-4-yl(3-(trifluoromethyl)-5,6-dihydro-[1,2,4]triazolo[4,3-a]pyrazin-7(8H)-yl)methanone 2,2,2-trifluoroacetate TFA (2 mL, 26.0 mmol) was added to a mixture of tert-butyl 4-(3-(trifluoromethyl)-5,6,7,8-tetrahydro-[1,2,4]triazolo[4,3-a]pyrazine-7-carbonyl)piperidine-1-carboxylate (500 mg, 1.24 mmol) in DCM (6 mL) and stirred at 18° C. for 1.5 h. The reaction was concentrated to give piperidin-4-yl(3-(trifluoromethyl)-5,6-dihydro-[1,2,4]triazolo[4,3-a]pyrazin-7(8H)-yl)methanone 2,2,2-trifluoroacetate. MS: 304 (M+1).

Intermediate 11

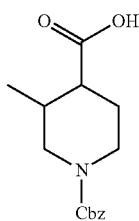

1-[(benzyloxy)carbonyl]-3-methylpiperidine-4-carboxylic acid 1-(tert-butoxycarbonyl)-3-methylpiperidine-4-carboxylic acid (10.0 g, 41.1 mmol) was combined with DCM (206 mL) and TFA (15.8 mL, 206 mmol) and stirred at room temperature for 15 h. The mixture was concentrated and the reaction diluted with dioxane (200 mL). Added potassium carbonate (56.8 g, 411 mmol) in water (200 mL) followed by benzyl chloroformate (7.04 mL, 49.3 mmol) and stirred at room temperature for 15 h. The reaction was diluted with water and extracted with EtOAc (1×). The aqueous layer was then acidified to pH 2 with 1N HCl. Added EtOAc and extracted (3×). The organic layers were combined and dried with magnesium sulfate, filtered, and concentrated. The residue was purified by silica gel chromatography (0-70% 3:1 EtOAc:EtOH in hexane). The combined fractions were concentrated to give the title compound. MS: 278 (M+1).

Intermediate 12

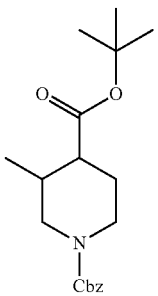

1-benzyl 4-tert-butyl 3-methylpiperidine-1,4-dicarboxylate 1-((benzyloxy)carbonyl)-3-methylpiperidine-4-carboxylic acid (9.08 g, 32.7 mmol), tert-butanol (4.70 mL, 49.1 mmol), 1-ethyl-3-(-3-dimethylaminopropyl) carbodiimide hydrochloride (7.53 g, 39.3 mmol), and DMAP (4.00 g, 32.7 mmol) were combined with DCM (164 mL). TEA (13.7 mL, 98 mmol) was added to the reaction and the reaction was stirred at room temperature over the weekend. Additional tert-butanol (4.70 mL, 49.1 mmol), 1-ethyl-3-(-3-dimethylaminopropyl) carbodiimide hydrochloride (7.53 g, 39.3 mmol), and DMAP (4.00 g, 32.7 mmol) was added and the mixture was stirred at room temperature for 15 h. Water was added to the reaction and the combined fractions were extracted with EtOAc (3×). The combined organic layers were dried with magnesium sulfate, filtered, concentrated and purified by silica gel chromatography (0-50% EtOAc in Hexane). The fractions were combined and concentrated to give the title compound. MS: 334 (M+1).

Intermediates 12a and 12b

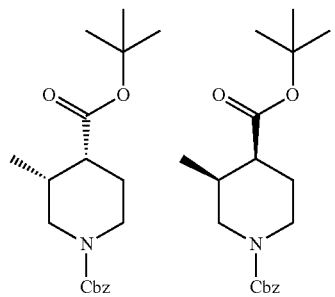

1-benzyl 4-tert-butyl (3R,4R)-3-methylpiperidine-1,4-dicarboxylate 1-benzyl 4-tert-butyl (3S,4S)-3-methylpiperidine-1,4-dicarboxylate 1-benzyl 4-tert-butyl 3-methylpiperidine-1,4-dicarboxylate (4.30 g, 12.9 mmol) was separated into diasteromers by SFC (Column: AD-H (2×25 cm), injection volume 0.5 mL at 17 mg/mL in MeOH, wavelength 210 nm, 30% MeOH/CO$_2$ at 100 bar). SFC separation afforded 1-benzyl 4-tert-butyl (3R,4R)-3-methylpiperidine-1,4-dicarboxylate MS: 334 (M+1) (peak 1, SFC $t_R$=1.83 min) and 1-benzyl 4-tert-butyl (3S,4S)-3-methylpiperidine-1,4-dicarboxylate MS: 334 (M+1) (peak 2, SFC $t_R$=2.93 in).

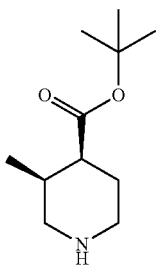

Intermediate 13a tert-butyl (3S,4S)-3-methylpiperidine-4-carboxylate 1-benzyl 4-tert-butyl (3S,4S)-3-methylpiperidine-1,4-dicarboxylate (1.47 g, 4.41 mmol) was dissolved in EtOAc (88 mL). 10% Pd—C (469 mg, 0.44 mmol) was added. The reaction was run under an atmosphere of hydrogen gas on the Parr shaker for 15 h at room temperature and 50 psi. The reaction was filtered through CELITE, washing the CELITE cake with EtOAc. The filtrate was concentrated to give the title compound. MS: 200 (M+1).

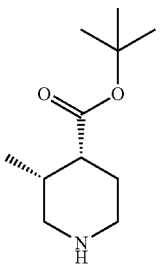

Intermediate 13b tert-butyl (3R,4R)-3-methylpiperidine-4-carboxylate 1-benzyl 4-tert-butyl (3R,4R)-3-methylpiperidine-1,4-dicarboxylate (75 mg, 0.23 mmol) was dissolved in EtOAc (4.5 mL). 10% Pd—C (24 mg, 0.022 mmol) was added. The reaction was run under an atmosphere of hydrogen gas on the Parr shaker for 15 h at room temperature and 50 psi. The reaction was filtered through CELITE, washing the CELITE cake with EtOAc. The filtrate was concentrated to give the title compound. MS: 200 (M+1).

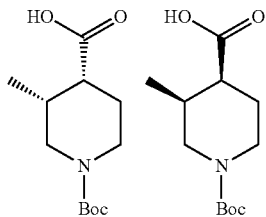

Intermediate 14a and 14b (3R,4R)-1-(tert-butoxycarbonyl)-3-methylpiperidine-4-carboxylic acid (3S,4S)-1-(tert-butoxycarbonyl)-3-methylpiperidine-4-carboxylic acid Rhodium (30 g, 292 mmol) was added to a solution of 3-methylpyridine-4-carboxylic acid hydrochloride (200 g, 461 mmol) in MeOH (2000 mL). The reaction was flushed with hydrogen gas (10 atmospheres). The reaction mixture was stirred for 5 days at 50° C. The solids were filtered out and the filtrate concentrated in vacuo. The residue was dissolved in water (1000 ml). Then NaOH (46.1 g, 1152 mmol) and Boc$_2$O (151 g, 691 mmol) was added. The mixture was stirred overnight at room temperature. The pH value of the solution was adjusted to 2-3 with 3N HCl and the combined fractions were extracted with EtOAc (800 mL, ×2). The combined organic layer was washed with brine and dried over anhydrous sodium sulfate and concentrated under vacuum. The solid was stirred overnight in EtOAc/n-hexane (1:10, 300 ml) and filtered. The solid was collected to afford racemic 1-(tert-butoxycarbonyl)-3-methylpiperidine-4-carboxylic acid. 1-(tert-butoxycarbonyl)-3-methylpiperidine-4-carboxylic acid (80 g, 329 mmol) was purified by SFC (twice) (Instrument: Thar SFC 350 Column: CHIRALPAK AD-H Mobile phase: % Solvent A: CO$_2$:85% Solvent B: MeOH (0.1% DEA)) to afford (3R,4R)-1-(tert-butoxycarbonyl)-3-methylpiperidine-4-carboxylic acid. MS: 266 (M+Na) (peak 1, SFC $t_R$=0.80 min) and (3S,4S)-1-(tert-butoxycarbonyl)-3-methylpiperidine-4-carboxylic acid. MS: 266 (M+Na) (peak 2, SFC $t_R$=1.14 min).

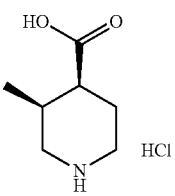

Intermediate 15a (3R,4R)-3-methylpiperidine-4-carboxylic acid hydrochloride (3R,4R)-1-(tert-butoxycarbonyl)-3-methylpiperidine-4-carboxylic acid (100 mg, 0.411 mmol) was dissolved in DCM (2.06 mL). HCl (4M in dioxane, 1.03 mL, 4.11 mmol) was added and the reaction was stirred at room temperature for 15 h. The reaction was concentrated and dried on the lyophilizer to give the title compound.

Intermediate 15b (3S,4S)-3-methylpiperidine-4-carboxylic acid hydrochloride (3S,4S)-3-methylpiperidine-4-carboxylic acid hydrochloride was made in a similar way to Intermediate 15a, using (3S,4S)-1-(tert-butoxycarbonyl)-3-methylpiperidine-4-carboxylic acid.

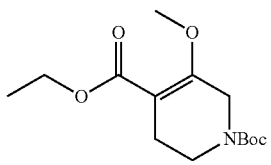

Intermediate 16

1-(tert-butyl) 4-ethyl 5-methoxy-3,6-dihydropyridine-1,4(2H)-dicarboxylate

NaH (0.451 g, 11.28 mmol) was gradually added to a solution of 1-(tert-butyl) 4-ethyl 3-oxopiperidine-1,4-dicarboxylate (2 g, 7.37 mmol) in THF (20.48 mL). The mixture was stirred at 20° C. for 1 h. To the mixture was added Me$_2$SO$_4$ (1.021 mL, 10.69 mmol) and the mixture was stirred at 60° C. for 3 h. The mixture was poured into water (100 mL), extracted with EtOAc (50 mL×2). The combined extracts were dried over Na$_2$SO$_4$, filtered and concentrated in vacuo. The residue was purified by silica gel chromatography (PE:EtOAc=10:1~5:1) to 1-(tert-butyl) 4-ethyl 5-methoxy-3,6-dihydropyridine-1,4(2H)-dicarboxylate. $^1$H NMR (400 MHz, chloroform-d) δ=4.19 (q, J=8.0 Hz, 2H), 4.14-4.00 (m, 2H), 3.77 (s, 3H), 3.43 (t, J=5.3 Hz, 2H), 2.41 (br. s., 2H), 1.46 (s, 9H), 1.29 (t, J=8.0 Hz, 3H)

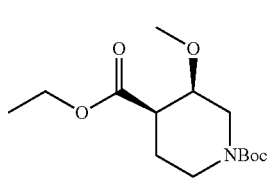

Intermediate 16a cis-1-(tert-butyl) 4-ethyl 3-methoxypiperidine-1,4-dicarboxylate A mixture of 1-(tert-butyl) 4-ethyl 5-methoxy-3,6-dihydropyridine-1,4(2H)-dicarboxylate (0.9 g, 3.15 mmol) and Pd—C (0.336 g, 0.315 mmol) in MeOH (20 mL) was stirred under hydrogen balloon at 20° C. for 1 h. The mixture was filtered, and the filter cake washed with EtOH (30 mL). The filtrate was concentrated in vacuo to give cis-1-(tert-butyl) 4-ethyl 3-methoxypiperidine-1,4-dicarboxylate as an oil. $^1$H NMR (400 MHz, chloroform-d) δ=4.53-4.29 (m, 1H), 4.25-4.08 (m, 3H), 3.76-3.69 (m, 1H), 3.35 (s, 3H), 2.87-2.58 (m, 2H), 2.51 (td, J=3.4, 12.1 Hz, 1H), 1.98 (dq, J=4.1, 12.7 Hz, 1H), 1.62 (br. s., 1H), 1.45 (s, 9H), 1.26 (t, J=8.0 Hz, 3H)

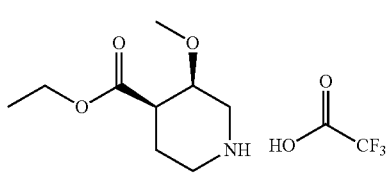

Intermediate 17 cis-ethyl-3-methoxypiperidine-4-carboxylate 2,2,2-trifluoroacetate

TFA (4.34 mL, 56.4 mmol) was added to a solution of cis-1-(tert-butyl) 4-ethyl 3-methoxypiperidine-1,4-dicarboxylate (0.81 g, 2.82 mmol) in DCM (14.09 mL). The resulting mixture was stirred at 20° C. for 5 h. The mixture was concentrated in vacuo directly to give the title compound. $^1$H NMR (400 MHz, METHANOL-d$_4$) δ=4.29-4.08 (m, 3H), 3.63 (d, J=13.5 Hz, 1H), 3.40 (s, 3H), 3.39-3.34 (m, 1H), 3.09-2.95 (m, 2H), 2.81 (td, J=3.5, 12.5 Hz, 1H), 2.14 (dq, J=4.3, 13.6 Hz, 1H), 2.02-1.96 (m, 1H), 1.28 (t, J=8.0 Hz, 3H)

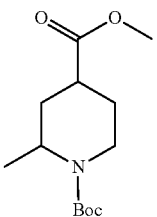

Intermediate 18

1-(tert-butyl) 4-methyl 2-methylpiperidine-1,4-dicarboxylate

A mixture of di-tert-butyl dicarbonate (8.0 g, 36.7 mmol), methyl 2-methylisonicotinate (2.6 g, 17.20 mmol) and platinum(IV) oxide (260 mg, 1.145 mmol) in MeOH (30 mL) was stirred under hydrogen atmosphere (50 psi) for 5 days at 25° C. The mixture was filtered through CELITE and concentrated. The residue was purified by silica gel chromatography (PE:EtOAc=50:1) to afford 1-tert-butyl 4-methyl 2-methylpiperidine-1,4-dicarboxylate. $^1$H NMR (400 MHz, CDCl$_3$): δ=4.21-4.13 (m, 1H), 3.87-3.78 (m, 1H), 3.70 (s, 3H), 3.17-3.00 (m, 1H), 2.63-2.51 (m, 1H), 2.02-1.82 (m, 3H), 1.73 (tt, J=6.2, 12.8 Hz, 1H), 1.45 (s, 9H), 1.07 (d, J=6.8 Hz, 3H).

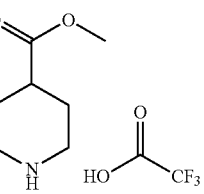

Intermediate 19 methyl 2-methylpiperidine-4-carboxylate 2,2,2-trifluoroacetate

TFA (2.5 mL, 32.4 mmol) was added to a mixture of 1-(tert-butyl) 4-methyl 2-methylpiperidine-1,4-dicarboxylate (800 mg, 3.11 mmol) in DCM (5 mL). The reaction was stirred at 20° C. for 2.5 h. The reaction was concentrated to give methyl 2-methylpiperidine-4-carboxylate 2,2,2-trifluoroacetate. MS: 158 (M+1).

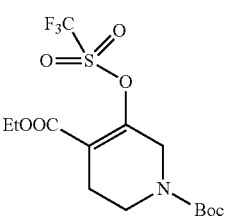

Intermediate 20

1-tert-butyl 4-ethyl 5-{[(trifluoromethyl)sulfonyl]oxy}-3,6-dihydropyridine-1,4(2H)-dicarboxylate A solution of 1-tert-butyl 4-ethyl 3-oxopiperidine-1,4-dicarboxylate (5.0 g, 18.43 mmol) and DIEA (4.83 mL, 27.6 mmol) in CH$_2$Cl$_2$ (80 mL) was cooled to −78° C. under a nitrogen atmosphere. Triflic anhydride (Tf$_2$O) (3.74 mL, 22.11 mmol) was added dropwise, and the reaction mixture was stirred at this temperature for 45 min. The mixture was treated with saturated NaHCO$_3$ (50 mL). The organic phase was separated and the aqueous phase was extracted with DCM (2×60 mL). The combined organic layers were dried over Na$_2$SO$_4$, filtered and concentrated to give 1-tert-butyl 4-ethyl 5-{[(trifluoromethyl)sulfonyl]oxy}-3,6-dihydropyridine-1,4(2H)-dicarboxylate. $^1$H NMR (400 MHz, chloroform-d) δ=4.28 (q, J=7.1 Hz, 2H), 4.10 (br. s., 2H), 3.51 (t, J=5.5 Hz, 2H), 2.58 (br. s., 2H), 1.46 (s, 9H), 1.32 (t, J=7.2 Hz, 3H).

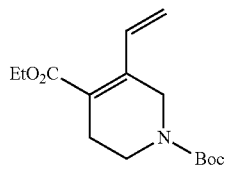

Intermediate 21

1-tert-butyl 4-ethyl 3-vinyl-5,6-dihydropyridine-1,4(2H)-dicarboxylate

A mixture of 1-tert-butyl 4-ethyl 5-{[(trifluoromethyl)sulfonyl]oxy}-3,6-dihydropyridine-1,4(2H)-dicarboxylate (12.39 g, 18.43 mmol), 4,4,5,5-tetramethyl-2-vinyl-1,3,2-dioxaborolane (3.41 g, 22.12 mmol), Cs$_2$CO$_3$ (12.01 g, 36.9 mmol) and [1,1'-bis(diphenylphosphino)ferrocene]dichloropalladium(II) complex with dichloromethane (1.505 g, 1.843 mmol) in 1,4-dioxane (73.7 mL) and water (18.43 mL) was heated under N$_2$ atmosphere (1 atm) at 80° C. for 4 h. The reaction mixture was cooled to room temperature and poured into water (100 mL). The mixture was extracted with EtOAc (3×80 mL). The combined organic layers were dried with Na$_2$SO$_4$, filtered and concentrated. The residue was purified by column chromatography on silica gel eluting with EtOAc/petroleum ether (1:20) to give 1-tert-butyl 4-ethyl 3-vinyl-5,6-dihydropyridine-1,4(2H)-dicarboxylate. $^1$H NMR (400 MHz, chloroform-d) δ=7.31-7.20 (m, 1H), 5.40 (br. s., 1H), 5.31-5.21 (m, 1H), 4.28-4.12 (m, 4H), 3.49 (br. s., 2H), 2.49 (br. s., 2H), 1.47 (s, 9H), 1.31 (t, J=7.0 Hz, 3H).

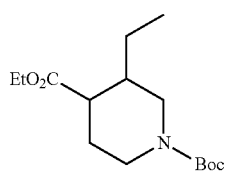

Intermediate 22

1-tert-butyl 4-ethyl 3-ethylpiperidine-1,4-dicarboxylate

A mixture of 1-tert-butyl 4-ethyl 3-vinyl-5,6-dihydropyridine-1,4(2H)-dicarboxylate (503 mg, 1.788 mmol) and Pd—C (19.03 mg, 0.179 mmol) in MeOH (8 mL) was stirred at 25° C. under H$_2$ atmosphere (15 psi) for 18 h. The mixture was filtered and the filter cake washed with MeOH (8 mL). The filtrate was concentrated to give 1-tert-butyl 4-ethyl 3-ethylpiperidine-1,4-dicarboxylate. MS: 286 (M+1).

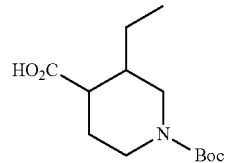

Intermediate 23

1-(tert-butoxycarbonyl)-3-ethylpiperidine-4-carboxylic acid

NaOH (2.124 mL, 8.50 mmol) was added to a solution of 1-tert-butyl 4-ethyl 3-ethylpiperidine-1,4-dicarboxylate (485 mg, 1.70 mmol) in EtOH (8 mL). The mixture was stirred at 25° C. for 16 h. The mixture was heated to 50° C. and stirred for additional 2 h. The mixture was neutralized with concentrated HCl to pH=7. The reaction was concentrated to give 1-(tert-butoxycarbonyl)-3-ethylpiperidine-4-carboxylic acid. MS: 515 (2M+1).

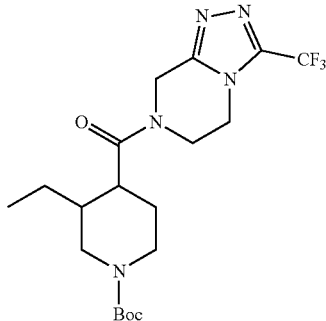

Intermediate 24 tert-butyl 3-ethyl-4-{[3-(trifluoromethyl)-5,6-dihydro[1,2,4]triazolo[4,3-a]pyrazin-7(8H)-yl]carbonyl}piperidine-1-carboxylate DIEA (1.19 mL, 6.80 mmol) was added to a stirred mixture of 1-(tert-butoxycarbonyl)-3-ethylpiperidine-4-carboxylic acid (437 mg, 1.70 mmol), 3-(trifluoromethyl)-5,6,7,8-tetrahydro-[1,2,4]triazolo[4,3-a]pyrazine hydrochloride (427 mg, 1.87 mmol) and HATU (711 mg, 1.87 mmol) in DMF (5663 μL) and the mixture was stirred at 25° C. for 16 h. The reaction mixture was cooled and poured into water (20 mL). The mixture was extracted with EtOAc (3×20 mL). The combined organic layers were dried with Na$_2$SO$_4$, filtered and concentrated. The residue was purified by column chromatography on silica gel eluting with EtOAc/petroleum ether/NH$_4$OH (1:1:0.1) to give tert-butyl 3-ethyl-4-(3-(trifluoromethyl)-5,6,7,8-tetrahydro-[1,2,4]triazolo[4,3-a]pyrazine-7-carbonyl)piperidine-1-carboxylate. MS: 432 (2M+1).

Intermediate 24a and 24b

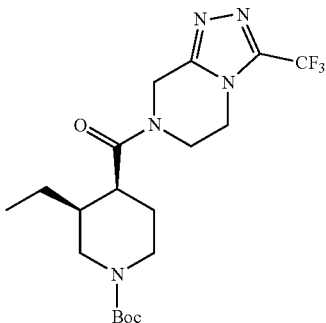

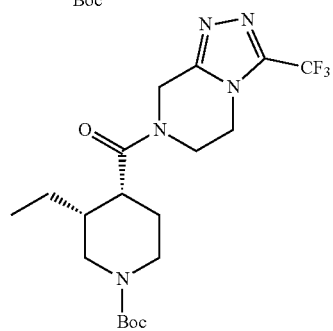

tert-butyl (3S,4S)-3-ethyl-4-{[3-(trifluoromethyl)-5,6-dihydro[1,2,4]triazolo[4,3-a]pyrazin-7(8H)-yl]carbonyl}piperidine-1-carboxylate tert-butyl (3R,4R)-3-ethyl-4-{[3-(trifluoromethyl)-5,6-dihydro[1,2,4]triazolo[4,3-a]pyrazin-7(8H)-yl]carbonyl}piperidine-1-carboxylate Tert-butyl 3-ethyl-4-(3-(trifluoromethyl)-5,6,7,8-tetrahydro-[1,2,4]triazolo[4,3-a]pyrazine-7-carbonyl)piperidine-1-carboxylate (584 mg, 1.354 mmol) was separated. Column: Lux Cellulose-2 150×4.6 mm I.D., 3 μm. Mobile phase: A: $CO_2$ B:IPA (0.05% DEA). Gradient: from 5% to 40% of B in 5.5 min, held at 40% of B for 3 min, then at 5% of B for 1.5 min. Flow rate: 2.5 mL/min Column temperature: 40° C. The SFC separation yielded the titled cis diastereomers (major peak 1, tert-butyl (3R,4R)-3-ethyl-4-{[3-(trifluoromethyl)-5,6-dihydro[1,2,4]triazolo[4,3-a]pyrazin-7(8H)-yl]carbonyl}piperidine-1-carboxylate, at 4.73 minutes; major peak 2, tert-butyl (3S,4S)-3-ethyl-4-{[3-(trifluoromethyl)-5,6-dihydro[1,2,4]triazolo[4,3-a]pyrazin-7(8H)-yl]carbonyl}piperidine-1-carboxylate, at 5.35 min.). MS: 432 (2M+1).

Intermediate 25b

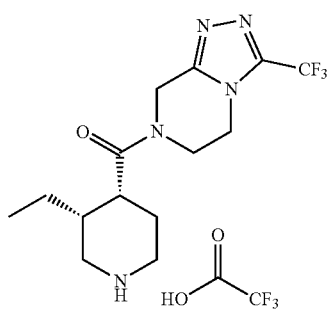

[(3R,4R)-3-ethylpiperidin-4-yl][3-(trifluoromethyl)-5,6-dihydro[1,2,4]triazolo[4,3-a]pyrazin-7(8H)-yl]methanone trifluoroacetate TFA (0.557 mL, 7.23 mmol) was added dropwise to a solution of tert-butyl (3R,4R)-3-ethyl-4-{[3-(trifluoromethyl)-5,6-dihydro[1,2,4]triazolo[4,3-a]pyrazin-7(8H)-yl]carbonyl}piperidine-1-carboxylate (SFC major peak 1) in DCM (5 mL) and the mixture was stirred at 30° C. for 1.5 h. The reaction mixture was concentrated to give [(3R,4R)-3-ethylpiperidin-4-yl][3-(trifluoromethyl)-5,6-dihydro[1,2,4]triazolo[4,3-a]pyrazin-7(8H)-yl]methanone trifluoroacetate. MS: 332 (M+1) $[a]D_{25}$=−15.39 (MeOH, c=1 mg/mL).

Intermediate 25a

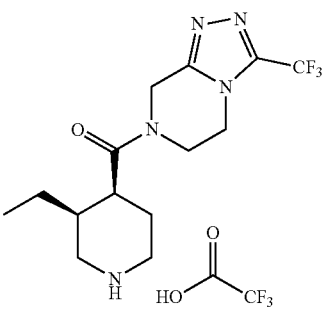

[(3S,4S)-3-ethylpiperidin-4-yl][3-(trifluoromethyl)-5,6-dihydro[1,2,4]triazolo[4,3-a]pyrazin-7(8H)-yl]methanone trifluoroacetate TFA (0.656 mL, 8.52 mmol) was added dropwise to a solution of tert-butyl (3S,4S)-3-ethyl-4-{[3-(trifluoromethyl)-5,6-dihydro[1,2,4]triazolo[4,3-a]pyrazin-7(8H)-yl]carbonyl}piperidine-1-carboxylate (SFC major peak 2, 245 mg, 0.568 mmol) in DCM (5 mL) was added, and the mixture was stirred at 30° C. for 1.5 h. The reaction mixture was concentrated to give [(3S,4S)-3-ethylpiperidin-4-yl][3-(trifluoromethyl)-5,6-dihydro[1,2,4]triazolo[4,3-a]pyrazin-7(8H)-yl]methanone trifluoroacetate. MS: 332 (M+1) [M+H$^+$]. $[a]D_{25}$=+19.41 (MeOH, c=1 mg/mL).

Intermediate 26

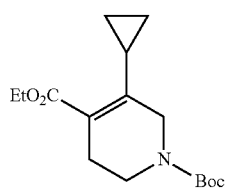

1-(tert-butyl) 4-ethyl 5-cyclopropyl-3,6-dihydropyridine-1,4(2H)-dicarboxylate

A mixture of 1-tert-butyl 4-ethyl 5-{[(trifluoromethyl)sulfonyl]oxy}-3,6-dihydropyridine-1,4(2H)-dicarboxylate (12.39 g, 18.43 mmol), cyclopropylboronic acid (1.900 g, 22.12 mmol), $Cs_2CO_3$ (12.01 g, 36.9 mmol) and [1,1'-bis(diphenylphosphino)ferrocene]dichloropalladium(II) complex with dichloromethane (1.505 g, 1.843 mmol) in 1,4-dioxane (73.7 mL) and water (18.43 mL) was heated under $N_2$ atmosphere (1 atm) at 80° C. for 5 h. The reaction mixture was cooled and poured into water (80 mL). The mixture was extracted with EtOAc (3×50 mL). The combined organic layers were dried with Na₂SO₄, filtered and concentrated. The residue was purified by silica gel chromatography (EtOAc:petroleum ether 1:20) to give the title compound. ¹H NMR (400 MHz, chloroform-d) δ=4.21 (q, J=7.2 Hz, 2H), 3.64 (br. s., 2H), 3.42 (t, J=5.1 Hz, 2H), 2.50 (br. s., 1H), 2.39 (br. s., 2H), 1.44 (s, 9H), 1.29 (t, J=7.2 Hz, 3H), 0.82-0.53 (m, 4H).

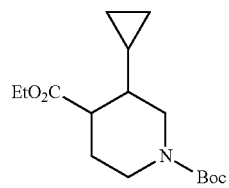

Intermediate 27

1-(tert-butyl) 4-ethyl 3-cyclopropylpiperidine-1,4-dicarboxylate

A mixture of 1-tert-butyl 4-ethyl 3-cyclopropyl-5,6-dihydropyridine-1,4(2H)-dicarboxylate (500 mg, 1.693 mmol) and Rh/C (87 mg, 0.846 mmol) in MeOH (5 mL) was stirred at 25° C. under H₂ atmosphere (15 psi) for 16 h. The mixture was filtered through CELITE, washed with MeOH (5 mL), and the filtrate was concentrated to give 1-tert-butyl 4-ethyl 3-cyclopropylpiperidine-1,4-dicarboxylate. MS: 298 (M+1)

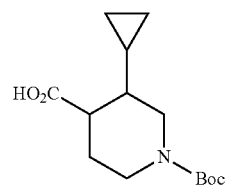

Intermediate 28

1-(tert-butoxycarbonyl)-3-cyclopropylpiperidine-4-carboxylic acid

To a solution of 1-tert-butyl 4-ethyl 3-cyclopropylpiperidine-1,4-dicarboxylate (0.503 g, 1.693 mmol) in EtOH (5 mL) was added NaOH (4.23 mL, 16.93 mmol). The mixture was stirred at 25° C. for 16 h. The mixture was heated to 50° C. and stirred for additional 3 h. The mixture was neutralized with conc HCl to pH=7 and concentrated to give 1-(tert-butoxycarbonyl)-3-cyclopropylpiperidine-4-carboxylic acid. MS: 539 (2M+1)

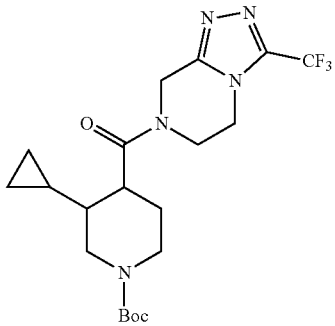

Intermediate 29 tert-butyl 3-cyclopropyl-4-(3-(trifluoromethyl)-5,6,7,8-tetrahydro-[1,2,4]triazolo[4,3-a]pyrazine-7-carbonyl)piperidine-1-carboxylate DIEA (1500 μL, 8.59 mmol) was added to a stirred mixture of 1-(tert-butoxycarbonyl)-3-cyclopropylpiperidine-4-carboxylic acid (578 mg, 2.147 mmol), 3-(trifluoromethyl)-5,6,7,8-tetrahydro-[1,2,4]triazolo[4,3-a]pyrazine hydrochloride (540 mg, 2.362 mmol) and HATU (898 mg, 2.362 mmol) in DMF (7.16 mL) and the mixture was stirred at 25° C. for 16 h. The reaction mixture was cooled and poured into water (20 mL). The mixture was extracted with EtOAc (3×20 ml). The combined organic layers were dried with Na₂SO₄, filtered and concentrated. The residue was purified by column chromatography on silica gel eluting with EtOAc/petroleum ether/NH₄OH (1:1:0.1) to give tert-butyl 3-cyclopropyl-4-(3-(trifluoromethyl)-5,6,7,8-tetrahydro-[1,2,4]triazolo[4,3-a]pyrazine-7-carbonyl)piperidine-1-carboxylate. MS: 887.5 (2M+1).

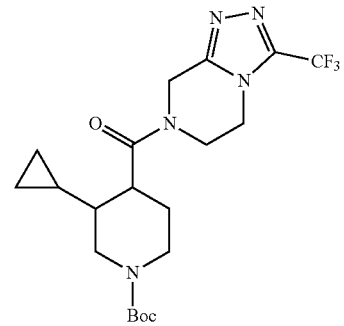
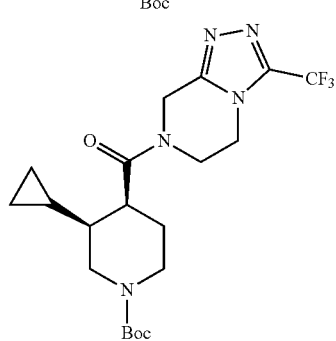

Intermediates 30, 30a and 30b

-continued

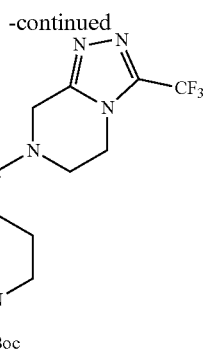

tert-butyl (3S,4S)-3-cyclopropyl-4-{[3-(trifluoromethyl)-5,6-dihydro[1,2,4]triazolo[4,3-a]pyrazin-7(8H)-yl]carbonyl}piperidine-1-carboxylate tert-butyl (3R,4R)-3-cyclopropyl-4-{[3-(trifluoromethyl)-5,6-dihydro[1,2,4]triazolo[4,3-a]pyrazin-7(8H)-yl]carbonyl}piperidine-1-carboxylate trans tert-butyl-3-cyclopropyl-4-{[3-(trifluoromethyl)-5,6-dihydro[1,2,4]triazolol[4,3-a]pyrazin-7(8H)-yl]carbonyl}piperidine-1-carboxylate tert-butyl 3-cyclopropyl-4-(3-(trifluoromethyl)-5,6,7,8-tetrahydro-[1,2,4]triazolo[4,3-a]pyrazine-7-carbonyl)piperidine-1-carboxylate (766 mg, 1.727 mmol) was separated (Column: Pheno Lux Cellulose-2 150×4.6 mm I.D., 5 um, Mobile phase: methanol (0.05% DEA) in carbon dioxide from 5% to 40%, Flow rate: 2.4 mL/min, Wavelength: 220 nm). Separation yielded cis Peak 1 (Rt=5.43 min) (238 mg, 0.534 mmol) which contained about 15% of trans isomer 1; cis Peak 2 (Rt=5.63 min) (212 mg, 0.476 mmol), and trans isomer 2 (Rt=5.94 min) (87 mg, 0.181 mmol) MS: 887.5 (2M+1).

Intermediate 31

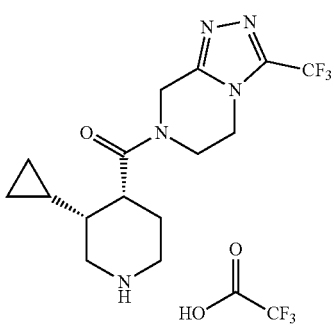

[(3R,4R)-3-cyclopropylpiperidin-4-yl][3-(trifluoromethyl)-5,6-dihydro[1,2,4]triazolo[4,3-a]pyrazin-7(8H)-yl]methanone trifluoroacetate TFA (0.503 mL, 6.53 mmol) was added dropwise to a solution of tert-butyl (3R,4R)-3-cyclopropyl-4-{[3-(trifluoromethyl)-5,6-dihydro[1,2,4]triazolo[4,3-a]pyrazin-7(8H)-yl]carbonyl}piperidine-1-carboxylate (193 mg, 0.435 mmol) in DCM (5 mL). The mixture was stirred at 30° C. for 3 h. The reaction mixture was concentrated to give the title compound. MS: 344 (2M+1). $[a]_D^{25}$=−8.046 (MeOH, c=1 mg/mL).

Intermediate 32

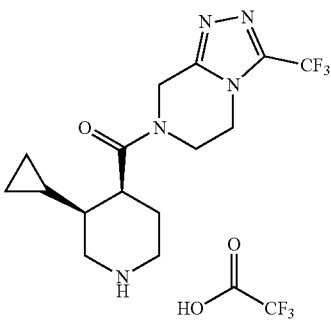

[(3S,4S)-3-cyclopropylpiperidin-4-yl][3-(trifluoromethyl)-5,6-dihydro[1,2,4]triazolo[4,3-a]pyrazin-7(8H)-yl]methanone trifluoroacetate TFA (0.552 mL, 7.17 mmol) was added dropwise to a solution of tert-butyl (3S,4S)-3-cyclopropyl-4-{[3-(trifluoromethyl)-5,6-dihydro[1,2,4]triazolo[4,3-a]pyrazin-7(8H)-yl]carbonyl}piperidine-1-carboxylate (212 mg, 0.478 mmol) in DCM (5 mL), the mixture was stirred at 30° C. for 3 h. The reaction mixture was concentrated to give the title compound. MS: 344 (2M+1). $[a]_D^{25}$=5.688 (MeOH, c=1 mg/mL).

Intermediate 33

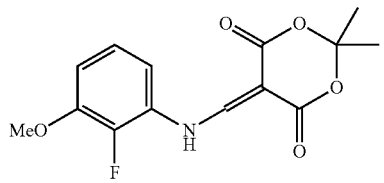

5-{[(2-fluoro-3-methoxyphenyl)amino]methylidene}-2,2-dimethyl-1,3-dioxane-4,6-dione 2,2-dimethyl-1,3-dioxane-4,6-dione (4.58 g, 31.78 mmol) in trimethyl orthoformate (27.3 mL, 245.9 mmol) was refluxed at 100° C. for 1 hr. 2-fluoro-3-methoxyaniline (3.9 g, 27.63 mmol) was then added and refluxing was continued for an additional hour. The reaction was cooled to room temperature and the suspension was filtered. The solid was washed with MeOH (60 mL) and dried under vacuum to yield the title compound. $^1$H NMR H20438-004-04 (400 MHz, chloroform-d) 6=11.36-11.38 (m, 1H), 8.63-8.60 (m, 1H), 7.26-6.83 (m, 3H), 3.92 (s, 3H), 1.75 (s, 6H).

Intermediate 34

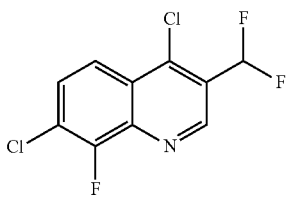

4,7-dichloro-3-(difluoromethyl)-8-fluoroquinoline

DIBAL-H (5.0 ml, 5.0 mmol) at −78° C. was added to a solution of 4,7-dichloro-8-fluoroquinoline-3-carbonitrile (400 mg, 1.7 mmol)) in THF (1.0 mL). The resulting mixture was stirred for 2 hrs at −78° C., then allowed to warm slowly to room temperature and stirred for 3 h. The mixture was diluted with saturated $NH_4Cl$ aqueous solution and extracted with EtOAc (2×). The combined organic layers were washed with water and brine, dried over anhydrous sodium sulfate, filtered and concentrated. The crude product was purified by MPLC ($SiO_2$; 100% $CH_2Cl_2$) to provide 4,7-dichloro-8-fluoroquinoline-3-carbaldehyde. MS: 245 (M+1).

DAST (0.087 mL, 0.67 mmol) was added to a solution of 4,7-dichloro-8-fluoroquinoline-3-carbaldehyde (80 mg, 0.33 mmol) in DCM (4 mL) at 0° C. and the cooling bath was removed. After 3 h at room temperature the mixture was diluted with $NaHCO_3$ and EtOAc and the layers were separated. The organic layer was washed with brine, dried with $Na_2SO_4$, filtered and concentrated to provide the desired product. MS: 266 (M+1).

Intermediate 35

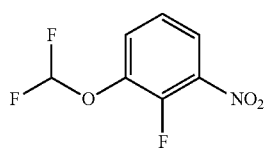

1-(difluoromethoxy)-2-fluoro-3-nitrobenzene 2-fluoro-3-nitrophenol (9 g, 57.3 mmol) was added to a mixture of sodium chlorodifluoroacetate (26.2 g, 172 mmol) and potassium carbonate (11.88 g, 86 mmol) in DMF (400 mL) and the mixture was stirred at 80° C. for 16 h. After cooling, the mixture was quenched with water (500 mL) and extracted with EtOAc (200 mL×3). The organic layer was then washed with water (100 mL), brine (50 mL×2) and dried over $Na_2SO_4$, filtered and concentrated. The crude material was purified by flash column chromatography on silica gel (PE:EtOAc=50:1) to afford the title compound. $^1$H NMR (400 MHz, $CDCl_3$) δ=7.95 (t, J=6.8 Hz, 1H), 7.59 (t, J=7.2 Hz, 1H), 7.34-7.27 (m, 1H), 6.83-6.43 (m, 1H).

Intermediate 36

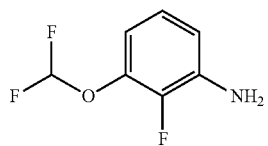

3-(difluoromethoxy)-2-fluoroaniline

Concentrated HCl (8.56 g, 87 mmol) was added to a mixture of 1-(difluoromethoxy)-2-fluoro-3-nitrobenzene (2 g, 7.24 mmol) and $SnCl_2$ (4.81 g, 25.3 mmol) in 2-propanol (100 ml) and the mixture was stirred for 30 min at 110° C. The reaction mixture was cooled to 25° C., diluted with water (30 mL) and the pH adjusted to 10 by addition of 2 N NaOH. The mixture was extracted with EtOAc (40 mL×3) and the organic layer was washed with brine (35 mL), dried over $Na_2SO_4$, filtered and concentrated to afford the title compound. $^1$H NMR (400 MHz, $CDCl_3$) δ=6.88 (dt, J=1.6, 8.2 Hz, 1H), 6.71-6.34 (m, 1H), 6.67-6.61 (m, 1H), 6.58 (t, J=7.6 Hz, 1H), 3.83 (br. s., 2H).

Intermediate 37

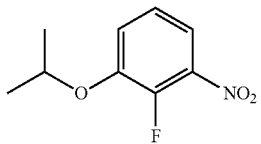

2-fluoro-1-isopropoxy-3-nitrobenzene $Cs_2CO_3$ (8.30 g, 25.5 mmol) was added to a mixture of 2-iodopropane (4.33 g, 25.5 mmol) and 2-fluoro-3-nitrophenol (2.0 g, 12.73 mmol) in DMF (30 mL) and the mixture was stirred at 25° C. for 16 h. The mixture was quenched with water (100 mL) and extracted with EtOAc (50 mL×3). The organic layer was then washed with water (20 mL), brine (30 mL×2) and dried over $Na_2SO_4$, filtered and concentrated. The crude material was purified by flash column chromatography on silica gel (PE:EtOAc=80:1) to afford 2-fluoro-1-isopropoxy-3-nitrobenzene. $^1$H NMR (400 MHz, $CDCl_3$) δ=7.61-7.52 (m, 1H), 7.23 (d, J=7.1 Hz, 1H), 7.18-7.12 (m, 1H, 4.59 (spt, J=6.0 Hz, 1H), 1.39 (d, J=6.0 Hz, 6H).

Intermediate 38

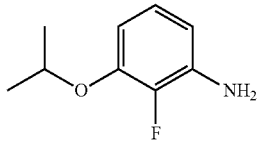

2-fluoro-3-isopropoxyaniline

Concentrated HCl (5.94 g, 60.2 mmol) was added to a mixture of 2-fluoro-1-isopropoxy-3-nitrobenzene (1.0 g, 5.02 mmol) and $SnCl_2$ (3.33 g, 17.57 mmol) in 2-propanol (10 ml) and stirred for 60 min at 110° C. The reaction mixture was cooled to 25° C., diluted with water (30 mL) and the pH adjusted to 10 by addition of 2 N NaOH. The mixture was extracted with EtOAc (30 mL×3) and the organic layer was washed with brine (20 mL), dried over $Na_2SO_4$, filtered and concentrated to afford 2-fluoro-3-isopropoxyaniline. $^1$H NMR (400 MHz, $CDCl_3$) δ=6.80 (dt, J=1.4, 8.1 Hz, 1H), 6.38 (t, J=8.0 Hz, 2H), 4.50 (quind, J=6.0, 12.1 Hz, 1H), 3.71 (br. s., 2H), 1.35 (d, J=5.9 Hz, 6H).

Intermediate 39

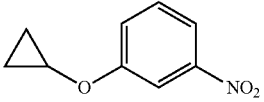

1-cyclopropoxy-3-nitrobenzene

A mixture of $Cs_2CO_3$ (58.6 g, 180 mmol), bromocyclopropane (26.1 g, 216 mmol) and 3-nitrophenol (10 g, 71.9 mmol) in DMF (200 mL) was stirred at 130° C. for 32 h. The mixture was diluted with water (300 mL) and extracted with EtOAc (150 mL×3). The organic layer was washed with brine (50 mL×3), dried over $Na_2SO_4$, filtered and concentrated. The residue was purified by silica gel chromatography (PE:EtOAc=10:1) to afford the title compound. $^1$H NMR (400 MHz, $CDCl_3$) δ=7.92 (s, 1H), 7.84 (d, J=8.2 Hz, 1H), 7.42 (t, J=8.2 Hz, 1H), 7.37-7.29 (m, 1H), 3.88-3.75 (m, 1H), 0.93-0.84 (m, 2H), 0.84-0.75 (m, 2H).

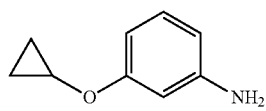

Intermediate 40

3-cyclopropoxyaniline

A mixture of 1-cyclopropoxy-3-nitrobenzene (2.18 g, 12.17 mmol) and Pd/C (1 g, 0.940 mmol) in MeOH (30 mL) was stirred at 25° C. for 2 h under $H_2$ (15 Psi). The mixture was filtered through CELITE and concentrated. The residue was purified by silica gel chromatography (PE:EtOAc=10:1) to afford the title compound. $^1$H NMR (400 MHz, $CDCl_3$) δ=7.06 (t, J=7.9 Hz, 1H), 6.48 (d, J=8.2 Hz, 1H), 6.39 (s, 1H), 6.31 (dd, J=1.2, 7.8 Hz, 1H), 3.74-3.65 (m, 1H), 0.75 s 4H).

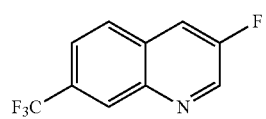

Intermediate 41

3-fluoro-7-(trifluoromethyl)quinoline

A 100 ml single neck round bottom flask was charged with 7-(trifluoromethyl)quinolin-3-amine (927 mg, 4.37 mmol) and tetrafluoroboric acid (48% solution in water, 5.71 ml, 43.7 mmol) and stirred vigorously at room temperature. The reaction mixture was cooled to 0° C. using salt-ice bath and added dropwise a solution of sodium nitrite (452 mg, 6.55 mmol) in water (1 ml) over 10 mins. After complete addition, the reaction mixture was allowed to stir at same temperature for 1 h, warmed to room temperature slowly over a period of 20 mins and stirred at ambient temperature for 10 mins. The precipitated solid was filtered through a Buckner Funnel, washed with 1 ml of water and vacuum dried for 15 mins. The solid was washed further with hexane (50 ml) and dried for another 15 mins under vacuum. The solid was transferred to a flask and diluted with Toluene (19.9 ml) and heated to reflux at 100° C. for 1 h. The solvent was evaporated under reduced pressure and the residue diluted with EtOAc and aqueous saturated sodium bicarbonate and stirred for 15 min at room temperature. The organic layer was separated and the aqueous layer back extracted with EtOAc. The combined organic layers were washed with water (1×), brine (1×) and dried over sodium sulfate. The organic layer was filtered and the solvent evaporated under reduced pressure. The residue was purified by silica gel chromatography (Hexanes/EtOAc) to provide the title compound. MS: 216 (M+1).

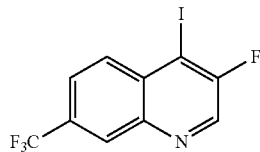

Intermediate 42

3-fluoro-4-iodo-7-(trifluoromethyl)quinoline nBuLi (1.6 M in hexane, 1.73 ml, 2.77 mmol) was added to a solution of diisopropylamine (0.395 ml, 2.77 mmol) in THF (2 ml) at 0° C. The reaction was stirred for 30 min at 0° C. 3-fluoro-7-(trifluoromethyl)quinoline (398 mg, 1.85 mmol) was cooled in THF (15 ml) to −78° C. for 30 min. The LDA solution was transferred to the quinoline solution at −78° C. dropwise. The reaction was stirred for 1 h at −78° C. Iodine (563 mg, 2.22 mmol) in THF (3 ml) was added and the reaction stirred for 30 min at −78° C. then taken out of the acetone bath and warmed up to room temperature for 4 h. The reaction was quenched with saturated ammonium chloride and extracted with EtOAc 3×. The combined organics layers were dried with magnesium sulfate, filtered and concentrated. The residue was purified by silica gel chromatography (EtOAc in Hexane). The combined fractions were concentrated to give the title compound. MS: 342 (M+1).

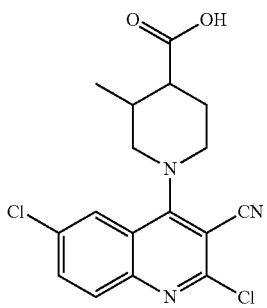

Intermediate 43

1-(2,6-dichloro-3-cyanoquinolin-4-yl)-3-methylpiperidine-4-carboxylic acid

DIPEA (8.36 ml, 47.9 mmol) was added to a stirred mixture of 2,4,6-trichloroquinoline-3-carbonitrile (4.11 g, 16.0 mmol) and 3-methylpiperidine-4-carboxylic acid hydrochloride (4.30 g, 23.9 mmol) in DMF (53 ml) at room temperature and the resulting mixture was heated at 70° C. for 1 hour. The reaction mixture was concentrated in vacuo and the resulting residue was purified by reverse phase chromatography (0-60% acetonitrile in water). The fractions were combined and concentrated to give the title compound. MS: 364 (M+1).

Intermediate 44

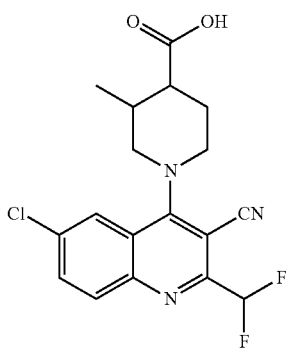

1-(6-chloro-3-cyano-2-(difluoromethyl)quinolin-4-yl)-3-methylpiperidine-4-carboxylic acid TFA (0.322 ml, 4.17 mmol) was added to a mixture of 1-(tert-butoxycarbonyl)-3-methylpiperidine-4-carboxylic acid (110 mg, 0.45 mmol) in DCM (1.04 mL). The mixture was stirred for 12 h at room temperature, then concentrated and dried under vacuum. 4,6-dichloro-2-(difluoromethyl) quinoline-3-carbonitrile (114 mg, 0.42 mmol) in DMF (1.04 mL) was added to the piperidine residue and the reaction heated at 70° C. for 3 hour. The reaction mixture was filtered and purified by reverse phase HPLC (10-100% MeCN/Water with 0.05% TFA). The combined fractions were extracted with EtOAc (3×). The combined organic layers were dried with magnesium sulfate, filtered, and concentrated to give the title compound. MS: 380 (M+1).

Intermediate 45

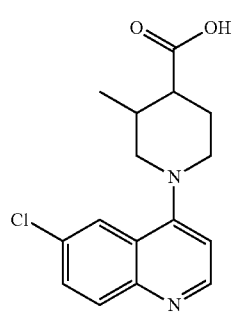

1-(6-chloroquinolin-4-yl)-3-methylpiperidine-4-carboxylic acid 1-(6-chloroquinolin-4-yl)-3-methylpiperidine-4-carboxylic acid was made in a similar way to 1-(6-chloro-3-cyano-2-(difluoromethyl)quinolin-4-yl)-3-methylpiperidine-4-carboxylic acid, starting with 4,6-dichloroquinoline (500 mg, 2.52 mmol). The reaction temperature of the piperidine coupling was changed to 90° C. for 15 hours to afford the title compound. MS: 305 (M+1).

Intermediate 46

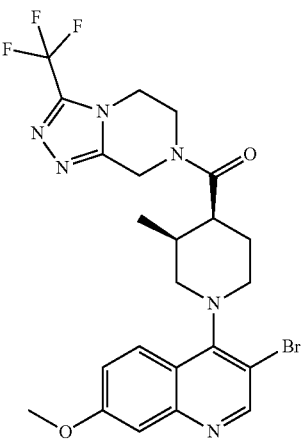

[(3S,4S)-1-(3-bromo-7-methoxyquinolin-4-yl)-3-methylpiperidin-4-yl][3-(trifluoromethyl)-5,6-dihydro[1,2,4]triazolo[4,3-a]pyrazin-7(8H)-yl]methanone 3-bromo-4-chloro-7-methoxyquinoline (100 mg, 0.37 mmol), DIPEA (0.192 mL, 1.10 mmol), ((3 S,4S)-3-methylpiperidin-4-yl)(3-(trifluoromethyl)-5,6-dihydro-[1,2,4]triazolo[4,3-a]pyrazin-7(8H)-yl)methanone hydrochloride (130 mg, 0.37 mmol), and DMF (1.84 mL) were combined in a sealed tube. The reaction was heated to 90° C. for 24 h. ((3S,4S)-3-methylpiperidin-4-yl)(3-(trifluoromethyl)-5,6-dihydro-[1,2,4]triazolo[4,3-a]pyrazin-7(8H)-yl)methanone hydrochloride (130 mg, 0.37 mmol) was added and the mixture was stirred for 36 h. Additional ((3S,4S)-3-methylpiperidin-4-yl)(3-(trifluoromethyl)-5,6-dihydro-[1,2,4]triazolo[4,3-a]pyrazin-7(8H)-yl)methanone hydrochloride (130 mg, 0.37 mmol) was added and stirred at 100° C. for 60 h. The reaction was filtered and purified by reverse phase HPLC (10-100% MeCN/Water, with 0.05% TFA). The combined fractions were neutralized with saturated sodium bicarbonate and extracted with EtOAc (2×). The organic layer was dried with magnesium sulfate, filtered, and concentrated to give the title compound. MS: 555 (M+1).

Intermediate 47

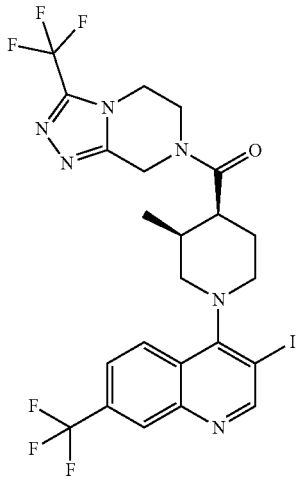

{(3S,4S)-1-[3-iodo-7-(trifluoromethyl)quinolin-4-yl]-3-methylpiperidin-4-yl}[3-(trifluoromethyl)-5,6-dihydro[1,2,4]triazolo[4,3-a]pyrazin-7(8H)-yl]methanone {(3S,4S)-1-[3-iodo-7-(trifluoromethyl)quinolin-4-yl]-3-methylpiperidin-4-yl}[3-(trifluoromethyl)-5,6-dihydro[1,2,4]triazolo[4,3-a]pyrazin-7(8H)-yl]methanone was made in a similar way to [(3S,4S)-1-(3-bromo-7-methoxyquinolin-4-yl)-3-methylpiperidin-4-yl][3-(trifluoromethyl)-5,6-dihydro[1,2,4]triazolo[4,3-a]pyrazin-7(8H)-yl]methanone, starting with 4-chloro-3-iodo-7-(trifluoromethyl)quinoline. MS: 639 (M+1).

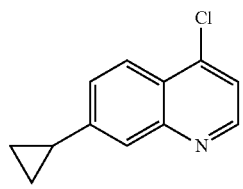

Intermediate 48

4-chloro-7-cyclopropylquinoline 7-bromo-4-chloroquinoline (550 mg, 2.27 mmol), potassium cyclopropyltrifluoroborate (369 mg, 2.50 mmol), PdCl$_2$(dppf)-CH$_2$Cl$_2$Adduct (185 mg, 0.23 mmol) and potassium phosphate tribasic (1M in water, 6.80 mL, 6.80 mmol) were added to a sealed tube. Dioxane (45.4 mL) was added and the reaction was purged with nitrogen gas for 5 min. The reaction was heated to 60° C. for 4 h, then cooled to room temperature. Additional potassium, cyclopropyltrifluoroborate (369 mg, 2.50 mmol) and PdCl$_2$(dppf)-CH$_2$Cl$_2$Adduct (185 mg, 0.23 mmol) was added. The reaction was sealed and purged with nitrogen gas and heated to 60° C. for 15 h. The reaction mixture was diluted with water and extracted with EtOAc (3×). The combined organic layers were dried with magnesium sulfate, filtered, concentrated and purified by silica gel chromatography (0-50% 3:1 EtOAc:EtOH in hexane). The combined fractions were concentrated to give the title compound. MS: 204 (M+1).

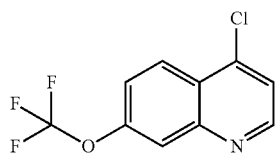

Intermediate 49

4-chloro-7-(trifluoromethoxy)quinoline

POCl$_3$ (0.305 mL, 3.27 mmol) was added to a stirred slurry of 7-(trifluoromethoxy)quinolin-4(1H)-one (250 mg, 1.09 mmol) in dioxane (5.45 mL). The reaction was heated at 90° C. for 3 h. The reaction was cooled and poured over ice. The reaction was quenched with saturated sodium bicarbonate and the aqueous layer extracted with EtOAc (3×). The combined organic layers were dried with magnesium sulfate, filtered and concentrated. The residue was purified by silica gel chromatography (0-100% 3:1 EtoAc:EtOH in hexane). The fractions were combined and concentrated to give the title compound. MS: 248 (M+1).

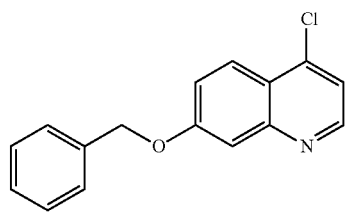

Intermediate 50

7-(benzyloxy)-4-chloroquinoline 7-(benzyloxy)-4-chloroquinoline was made in a similar way to 4-chloro-7-(trifluoromethoxy)quinoline, starting with 7-(benzyloxy)quinolin-4(1H)-one. MS: 270 (M+1).

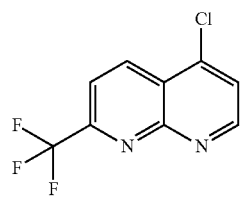

Intermediate 51

5-chloro-2-(trifluoromethyl)-1,8-naphthyridine 5-chloro-2-(trifluoromethyl)-1,8-naphthyridine was made in a similar way to 4-chloro-7-(trifluoromethoxy)quinoline, starting with 7-(trifluoromethyl)-1,8-naphthyridin-4(1H)-one. MS: 232 (M+1).

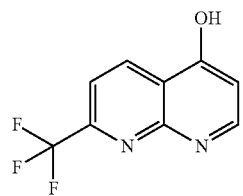

Intermediate 52

7-(trifluoromethyl)-1,8-naphthyridin-4(1H)-one 4-hydroxy-7-(trifluoromethyl)-1,8-naphthyridine-3-carboxylic acid (500 mg, 1.94 mmol) and Dowtherm A (5 mL) were combined in a round bottom flask. The reaction was heated to 260° C. for about 15 h. The heat was then turned off and the mixture was cooled to room temperature. Ether was added and the precipitate collected by filtration. The precipitate was washed with ether to give the title compound. MS: 215 (M+1).

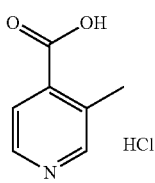

Intermediate 53

3-methylpyridine-4-carboxylic acid hydrochloride

LiOH (42.8 g, 1786 mmol) was added to a solution of methyl 3-methylisonicotinate (90 g, 596 mmol) in MeOH (900 ml) and water (450 ml) and the reaction mixture was stirred for 15 h at room temperature. Then the reaction mixture was adjusted to 3-4 with 1N HCl. The mixture was concentrated and purified on a silica gel chromatography (DCM:MeOH 3:1) to afford 3-methylisonicotinic acid. The 3-methylisonicotinic acid was stirred with HCl (4N in dioxane, 173 mL, 693 mmol) for 3 h at room temperature and filtered. The solid was washed with ether and dried to afford the title compound. MS: 138 (M+1).

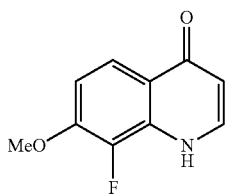

Intermediate 54

8-fluoro-7-methoxyquinolin-4(1H)-one

A mixture of 5-{[(2-fluoro-3-methoxyphenyl)amino]methylidene}-2,2-dimethyl-1,3-dioxane-4,6-dione (8.078 g, 27.4 mmol) in diphenylether (45 mL) was heated at 230° C. for 1 h. The reaction mixture was cooled to room temperature and filtered, the desired solid was washed with petroleum ether (3×30 mL) to give 8-fluoro-7-methoxyquinolin-4(1H)-one (4.461 g, 21.94 mmol). MS: 194 (M+1).

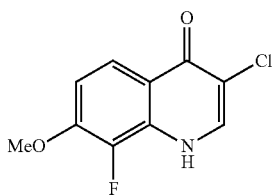

Intermediate 55

3-chloro-8-fluoro-7-methoxyquinolin-4(1H)-one

A mixture of 8-fluoro-7-methoxyquinolin-4(1H)-one (1.5 g, 7.77 mmol) and N-chlorosuccinimide (NCS) (1.14 g, 8.54 mmol) in acetic acid (51.8 mL) was heated at 60° C. for 5 h. The reaction mixture was cooled to room temperature and concentrated to dryness. Saturated NaHCO₃ (aqueous, 50 mL) was added and the solid collected and washed with water (3×15 mL) and dried in vacuo to give the title compound as a solid. MS: 228 (M+1).

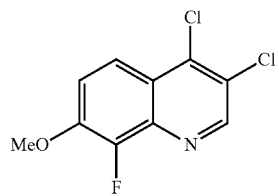

Intermediate 56

3,4-dichloro-8-fluoro-7-methoxyquinoline

To a stirred slurry of 3-chloro-8-fluoro-7-methoxyquinolin-4(1H)-one (1.606 g, 7.06 mmol) in 1,4-dioxane (23.52 mL) was added POCl₃ (1.973 mL, 21.17 mmol). The reaction was heated at 90° C. for 1.5 h. The reaction was cooled and poured into ice water (150 mL), then basified to pH=8 with solid K₂CO₃. The mixture was extracted with EtOAc (2×80 mL). The combined organic layers were dried over Na₂SO₄, filtered and concentrated to give the title compound. MS: 245.9 (M+1).

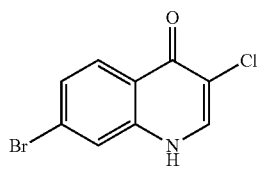

Intermediate 57

7-bromo-3-chloroquinolin-4(1H)-one

A mixture of 7-bromoquinolin-4(1H)-one (4.084 g, 18.23 mmol) and NCS (2.68 g, 20.05 mmol) in acetic acid (91 mL) was heated at 60° C. for 5 h. The reaction mixture was cooled to room temperature and concentrated to dryness. Saturated NaHCO₃ (aqueous, 80 mL) was added and the solid collected. The solid was washed with water (3×30 mL) and dried in vacuo to give the title compound which was used directly without purification. MS: 260 (M+1).

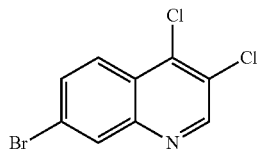

Intermediate 58

7-bromo-3,4-dichloroquinoline

POCl₃ (4.39 mL, 47.1 mmol) was added to a stirred slurry of 7-bromo-3-chloroquinolin-4(1H)-one (4.06 g, 15.71 mmol) in 1,4-dioxane (70 mL). The reaction was heated at 90° C. for 2.5 h. The reaction was cooled and poured into ice water (150 mL), then basified to pH=8 with solid K₂CO₃. The mixture was extracted with EtOAc (2×80 mL). The combined organic layers were dried over Na₂SO₄, filtered and concentrated. The residue was chromatographed on silica gel (EtOAc:petroleum ether=1:200) to give the title compound. MS: 277.7 (M+1).

Intermediate 59

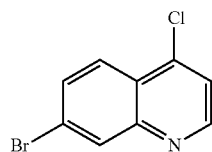

7-bromo-4-chloroquinoline

POCl$_3$ (6.99 mL, 75.0 mmol) was added to a mixture of 7-bromoquinolin-4-ol (5.6 g, 24.99 mmol) in dioxane (50 mL) and the mixture was stirred at 90° C. for 5 h. The mixture was poured into cold water (150 mL) and adjusted to pH-8 with solid Na$_2$CO$_3$. The mixture was extracted with EtOAc (50 mL×3). The organic layers were combined and washed with brine (1×50 mL), dried over Na$_2$SO$_4$, filtered and concentrated. The crude product was purified by silica gel chromatography (PE:EtOAc=30:1) to afford the title compound. MS: 243.9 (M+1).

Intermediate 60

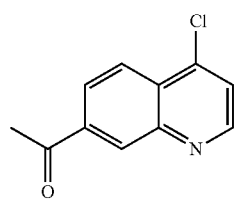

1-(4-chloroquinolin-7-yl)ethan-1-one

A mixture of tributyl(1-ethoxyvinyl)tin (1.392 mL, 4.12 mmol), 7-bromo-4-chloroquinoline (1 g, 4.12 mmol), bis(triphenylphosphine)palladium (II) dichloride (0.289 g, 0.412 mmol) and toluene (10 mL) was purged with N$_2$, then heated to 110° C. under N$_2$ atmosphere for 5 h. The mixture was cooled to room temperature and was used in the next step directly without further purification. A solution of THF/1.0 N HCl (1:1, 10 mL) was added to 4-chloro-7-(1-ethoxyvinyl)quinoline (964 mg, 4.13 mmol) and stirred at 25° C. vigorously for 1 h. Saturated KF (aqueous, 30 mL) was added to the mixture and the mixture was stirred at 25° C. for 0.5 h. The mixture was extracted with EtOAc (30 mL×3). The combined organic layers was washed with saturated aqueous solution of NaCl (10 mL), then dried over Na$_2$SO$_4$, filtered and concentrated. The residue was purified by silica gel chromatography (EtOAc/petroleum ether=1/7) to give the title compound. $^1$H NMR 1000126-064-1A (400 MHz, CDCl$_3$): δ 8.88 (d, J=4.8 Hz, 1H), 8.70 (d, J=1.3 Hz, 1H), 8.35-8.29 (m, 1H), 8.22 (dd, J=1.8, 8.8 Hz, 1H), 7.60 (d, J=4.5 Hz, 1H), 2.78 (s, 3H).

Intermediate 61

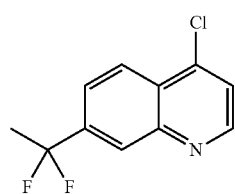

4-chloro-7-(1,1-difluoroethyl)quinoline

A mixture of pyridine hydrofluoride (32.8 mg, 0.331 mmol), 1-(4-chloroquinolin-7-yl)ethan-1-one (680 mg, 3.31 mmol) and BAST (1463 mg, 6.61 mmol) was stirred at 25° C. for 40 h. The mixture was diluted with saturated NaHCO$_3$ (100 mL) and extracted with EtOAc (30 mL*3). The organic layer was washed with brine (20 mL), dried over Na$_2$SO$_4$, filtered and concentrated. The residue was purified by silica gel chromatography (PE:EtOAc=10:1) to afford the title compound. MS: 228.0 (M+1).

Intermediate 62

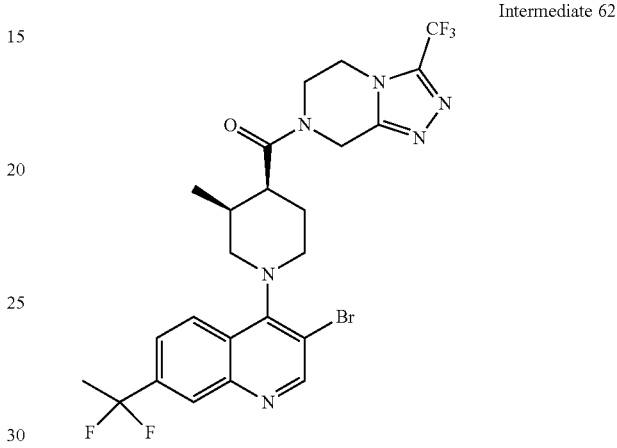

{(3S,4S)-1-[3-bromo-7-(1,1-difluoroethyl)quinolin-4-yl]-3-methylpiperidin-4-yl}[3-(trifluoromethyl)-5,6-dihydro[1,2,4]triazolo[4,3-a]pyrazin-7(8H)-yl]methanone A mixture of {(3S,4S)-1-[7-(1,1-difluoroethyl)quinolin-4-yl]-3-methylpiperidin-4-yl}[3-(trifluoromethyl)-5,6-dihydro[1,2,4]triazolo[4,3-a]pyrazin-7(8H)-yl]methanone (250 mg, 0.246 mmol) and 1-bromopyrrolidine-2,5-dione (43.8 mg, 0.246 mmol) in DCM (3 mL) was stirred at −10° C. for 1 h. The reaction was concentrated and the mixture was purified by p-TLC (DCM:MeOH=20:1) to afford the title compound. $^1$H NMR (400 MHz, CDCl$_3$) α=8.86 (s, 1H), 8.19 (s, 1H), 7.67 (d, J=8.4 Hz, 1H), 5.22-4.96 (m, 2H), 4.36-4.18 (m, 3H), 4.17-3.96 (m, 2H), 3.46-2.98 (m, 4H), 2.58-2.47 (m, 1H), 2.25-2.19 (m, 1H), 2.02 (t, J=18.2 Hz, 3H), 1.80-1.70 (m, 1H), 1.22-1.04 (m, 3H)

Intermediate 63

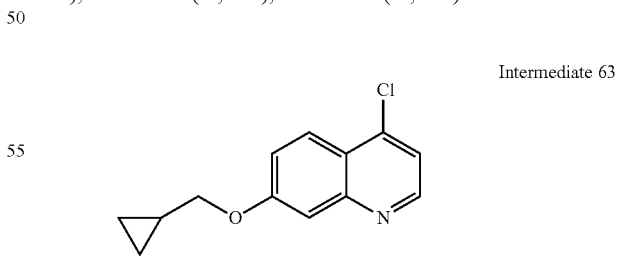

4-chloro-7-(cyclopropylmethoxy)quinoline

NaH (44.1 mg, 1.102 mmol, 40% in oil) was added to a stirred solution of 4-chloroquinolin-7-ol (100 mg, 0.367 mmol) in DMF (1837 μL) at 0° C. then warmed to 25° C., after 30 min, (bromomethyl)cyclopropane (99 mg, 0.735 mmol) was added to the mixture and stirred for 16 h. Water (20 mL) was added to the reaction mixture then extracted with EtOAc (10 mL×3). The combined organic layers was washed with saturated aqueous solution of NaCl (15 mL) then dried over $Na_2SO_4$, filtered and concentrated. The residue was purified by p-TLC ($SiO_2$, DCM:MeOH=50:1) to give the title compound. MS: 234 (M+1).

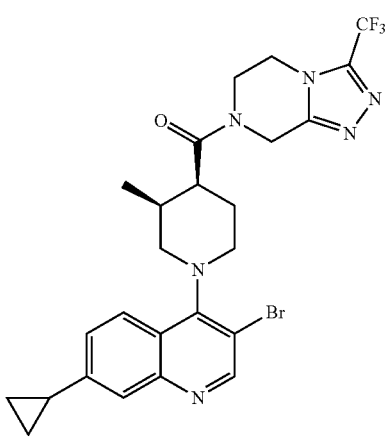

Intermediate 64

[(3S,4S)-1-(3-bromo-7-cyclopropylquinolin-4-yl)-3-methylpiperidin-4-yl][3-(trifluoromethyl)-5,6-dihydro[1,2,4]triazolo[4,3-a]pyrazin-7(8H)-yl]methanone NBS (177 mg, 0.997 mmol) was added to a stirred solution of ((3S,4S)-1-(7-cyclopropylquinolin-4-yl)-3-methylpiperidin-4-yl)(3-(trifluoromethyl)-5,6-dihydro-[1,2,4]triazolo[4,3-a]pyrazin-7(8H)-yl)methanone (483 mg, 0.997 mmol) in DCM (4985 µL at 0° C. and the mixture was stirred at this temperature for 15 min. Water (30 mL) was added to the reaction mixture then extracted with DCM (20 mL×3). The combined organic layers was washed with a saturated aqueous solution of NaCl (30 mL) then dried over $Na_2SO_4$, filtered and concentrated to give crude title compound. MS: 563 (M+1).

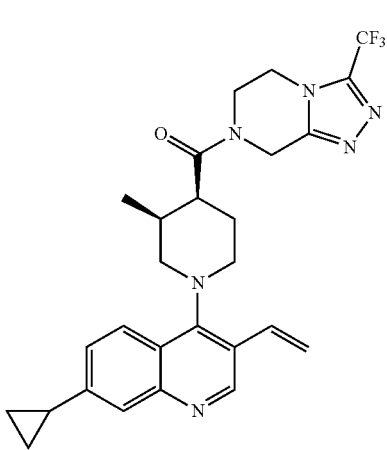

Intermediate 65

[(3S,4S)-1-(7-cyclopropyl-3-ethenylquinolin-4-yl)-3-methylpiperidin-4-yl][3-(trifluoromethyl)-5,6-dihydro[1,2,4]triazolo[4,3-a]pyrazin-7(81H)-yl]methanone A mixture of [(3S,4S)-1-(3-bromo-7-cyclopropylquinolin-4-yl)-3-methylpiperidin-4-yl][3-(trifluoromethyl)-5,6-dihydro[1,2,4]triazolo[4,3-a]pyrazin-7(81)-yl]methanone (300 mg, 0.532 mmol), 4,4,5,5-tetramethyl-2-vinyl-1,3,2-dioxaborolane (98 mg, 0.639 mmol), $Cs_2CO_3$ (347 mg, 1.065 mmol), [1,1'-bis(diphenylphosphino)ferrocene]dichloropalladium (II) (39.0 mg, 0.053 mmol), 1,4-dioxane (2.219 mL) and water (0.444 mL) was bubbled with $N_2$, then heated to 90° C. under $N_2$ atmosphere for 8 h. The reaction was cooled to room temperature, water (30 mL) was added then the mixture was extracted with EtOAc (20 mL*3). The combined organic layers were washed with a saturated aqueous solution of NaCl (20 mL) then dried over $Na_2SO_4$, filtered and concentrated. The residue was chromatographed on silica gel (MeOH/DCM=1:30) to give the title compound. MS: 511 (M+1).

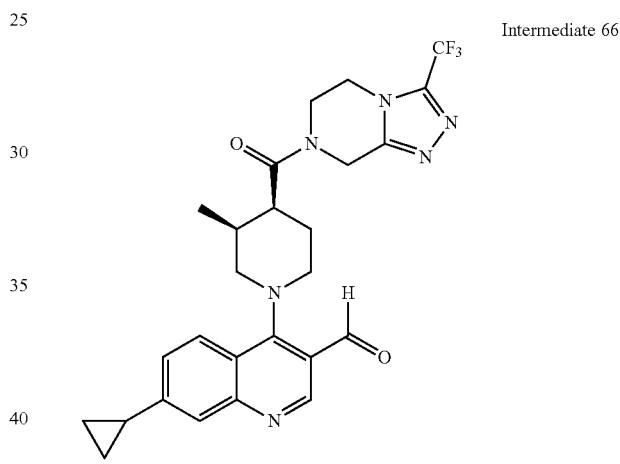

Intermediate 66

7-cyclopropyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbaldehyde Sodium periodate (318 mg, 1.489 mmol) was added to the solution of [(3S,4S)-1-(7-cyclopropyl-3-ethenylquinolin-4-yl)-3-methylpiperidin-4-yl][3-(trifluoromethyl)-5,6-dihydro[1,2,4]triazolo[4,3-a]pyrazin-7(8H)-yl]methanone (190 mg, 0.372 mmol) and potassium osmate (VI) dihydrate (13.71 mg, 0.037 mmol) in dioxane/water=3:1 (4 mL). The reaction was kept stirring for 2 h at 25° C. Quenched with saturated aqueous $Na_2S_2O_3$ (10 mL) and extracted with ethyl acetate (3×15 mL). The combined organic layers were dried with $Na_2SO_4$, filtered and concentrated. The residue was chromatographed on silica gel (EtOAc) to the title compound. MS: 513 (M+1).

EXAMPLES

Example 1

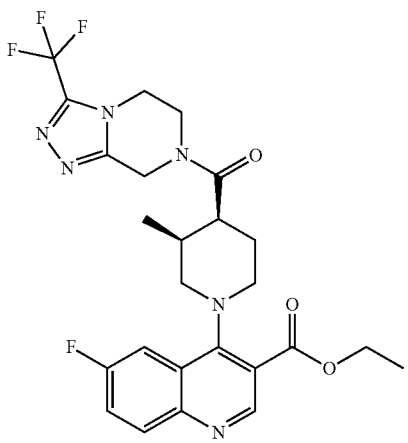 [SMILES: CCOC(=O)c1cnc2ccc(F)cc2c1N1CC[C@H](C(=O)N2CCn3c(nnc3C(F)(F)F)C2)[C@H](C)C1]

ethyl 6-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carboxylate Ethyl 4-chloro-6-fluoroquinoline-3-carboxylate (0.015 g, 0.059 mmol), ((3S,4S)-3-methylpiperidin-4-yl)(3-(trifluoromethyl)-5,6-dihydro-[1,2,4]triazolo[4,3-a]pyrazin-7(8H)-yl)methanone hydrochloride (0372268-0168) (0.021 g, 0.059 mmol), DIPEA (0.031 ml, 0.177 mmol), and DMF (0.591 ml) were combined in a sealed tube. The reaction was heated to 70° C. for 15 h. The reaction mixture was diluted with EtOAc and washed with water 3×. The organic layers were dried with magnesium sulfate, filtered, concentrated and purified by silica gel chromatography (0-100% 3:1 EtOAc:EtOH in Hexane). The combined fractions were concentrated to give the title compound. MS: 535 (M+1). Human CYP8B1 IC50 (nM) 3675.

Examples 2-9 were made using a similar synthesis to Example 1 substituting the appropriate reactants and reagents.

| Example | Structure | Chemical Name | Exact Mass [M + H]+ | Human CYP8B1 IC50 (nM) |
|---|---|---|---|---|
| Example 2 | 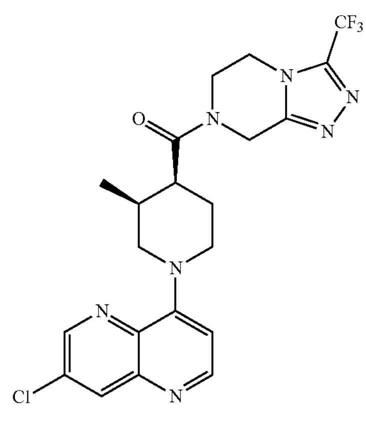 [SMILES: C[C@@H]1CN(c2ccnc3cc(Cl)cnc23)CC[C@@H]1C(=O)N1CCn2c(nnc2C(F)(F)F)C1] | ((3S,4S)-1-(7-chloro-1,5-naphthyridin-4-yl)-3-methylpiperidin-4-yl)(3-(trifluoromethyl)-5,6-dihydro-[1,2,4]triazolo[4,3-a]pyrazin-7(8H)-yl)methanone | 480 | 18 |
| Example 3 | 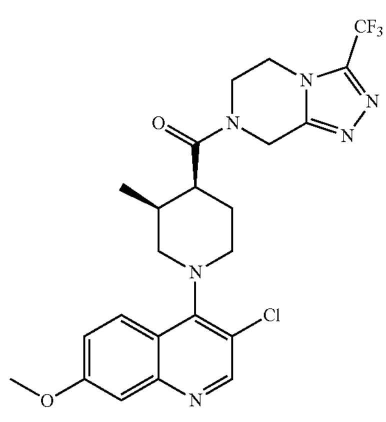 | ((3S,4S)-1-(3-chloro-7-methoxyquinolin-4-yl)-3-methylpiperidin-4-yl)(3-(trifluoromethyl)-5,6-dihydro-[1,2,4]triazolo[4,3-a]pyrazin-7(8H)-yl)methanone | 509 | 0.2 |

-continued

| Example | Structure | Chemical Name | Exact Mass [M + H]+ | Human CYP8B1 IC50 (nM) |
|---------|-----------|---------------|---------------------|------------------------|
| Example 4 | 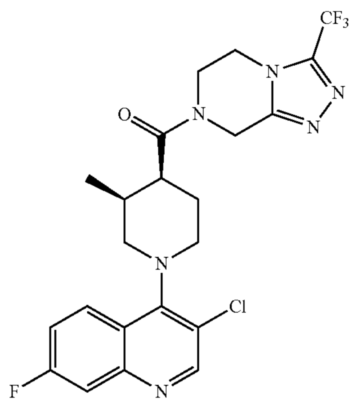 [SMILES: C[C@@H]1CN(c2c(Cl)cnc3cc(F)ccc23)CC[C@@H]1C(=O)N1CCn2c(nnc2C(F)(F)F)C1] | ((3S,4S)-1-(3-chloro-7-fluoroquinolin-4-yl)-3-methylpiperidin-4-yl)(3-(trifluoromethyl)-5,6-dihydro-[1,2,4]triazolo[4,3-a]pyrazin-7(8H)-yl)methanone | 497 | 0.6 |
| Example 5 | 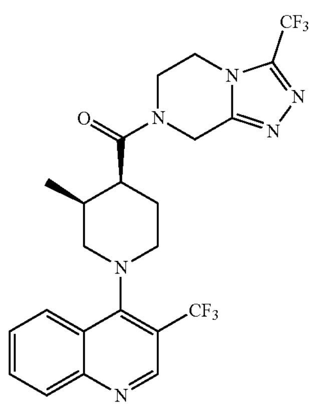 [SMILES: C[C@@H]1CN(c2c(C(F)(F)F)cnc3ccccc23)CC[C@@H]1C(=O)N1CCn2c(nnc2C(F)(F)F)C1] | ((3S,4S)-3-methyl-1-(3-(trifluoromethyl)quinolin-4-yl)piperidin-4-yl)(3-(trifluoromethyl)-5,6-dihydro-[1,2,4]triazolo[4,3-a]pyrazin-7(8H)-yl)methanone | 513 | 1.0 |
| Example 6 | 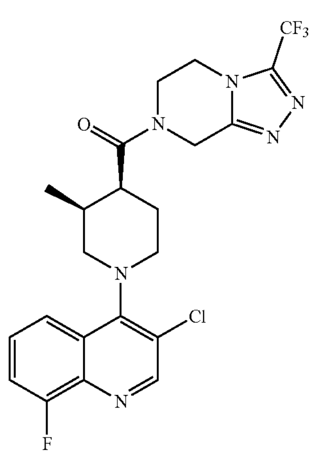 [SMILES: C[C@@H]1CN(c2c(Cl)cnc3c(F)cccc23)CC[C@@H]1C(=O)N1CCn2c(nnc2C(F)(F)F)C1] | ((3S,4S)-1-(3-chloro-8-fluoroquinolin-4-yl)-3-methylpiperidin-4-yl)(3-(trifluoromethyl)-5,6-dihydro-[1,2,4]triazolo[4,3-a]pyrazin-7(8H)-yl)methanone | 497 | 0.9 |

-continued

| Example | Structure | Chemical Name | Exact Mass [M + H]+ | Human CYP8B1 IC50 (nM) |
|---|---|---|---|---|
| Example 7 | 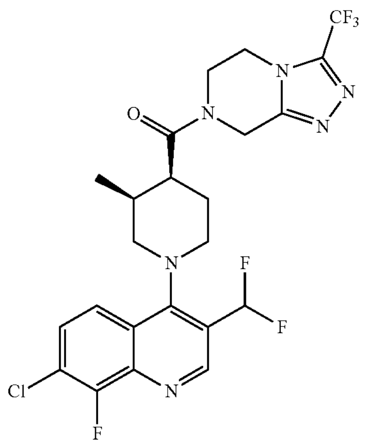 [SMILES: C[C@@H]1CN(c2c(C(F)F)cnc3c(F)c(Cl)ccc23)CC[C@@H]1C(=O)N1CCn2c(nnc2C(F)(F)F)C1] | ((3S,4S)-1-(7-chloro-3-(difluoromethyl)-8-fluoroquinolin-4-yl)-3-methylpiperidin-4-yl)(3-(trifluoromethyl)-5,6-dihydro-[1,2,4]triazolo[4,3-a]pyrazin-7(8H)-yl)methanone | 547 | 0.7 |
| Example 8 | 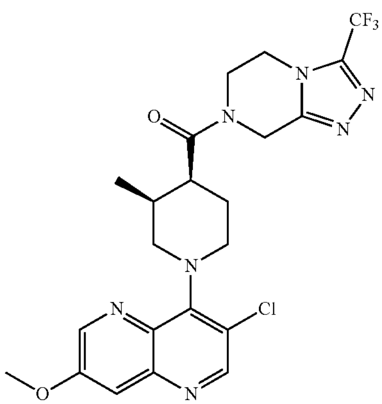 [SMILES: COc1cnc2c(N3CC[C@H](C(=O)N4CCn5c(nnc5C(F)(F)F)C4)[C@H](C)C3)c(Cl)cnc2c1] | ((3S,4S)-1-(3-chloro-7-methoxy-1,5-naphthyridin-4-yl)-3-methylpiperidin-4-yl)(3-(trifluoromethyl)-5,6-dihydro-[1,2,4]triazolo[4,3-a]pyrazin-7(8H)-yl)methanone | 510 | 1.2 |
| Example 9 | 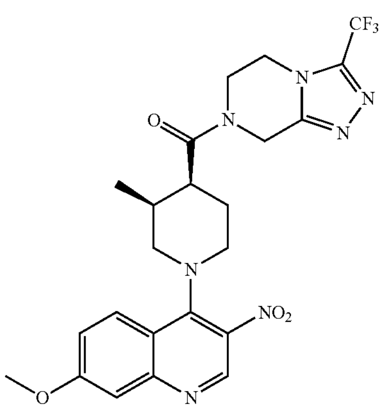 [SMILES: COc1ccc2c(N3CC[C@H](C(=O)N4CCn5c(nnc5C(F)(F)F)C4)[C@H](C)C3)c([N+](=O)[O-])cnc2c1] | ((3S,4S)-1-(7-methoxy-3-nitroquinolin-4-yl)-3-methylpiperidin-4-yl)(3-(trifluoromethyl)-5,6-dihydro-[1,2,4]triazolo[4,3-a]pyrazin-7(8H)-yl)methanone | 520 | 0.2 |

Example 10

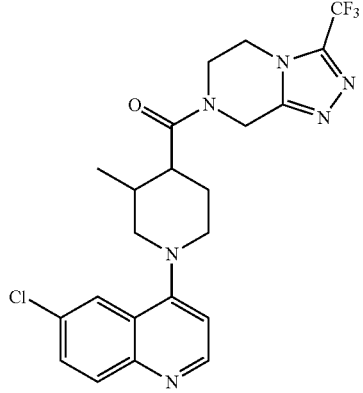 [SMILES: CC1CN(c2ccnc3ccc(Cl)cc23)CCC1C(=O)N1CCn2c(nnc2C(F)(F)F)C1]

[1-(6-chloroquinolin-4-yl)-3-methylpiperidin-4-yl][3-(trifluoromethyl)-5,6-dihydro[1,2,4]triazolo[4,3-a]pyrazin-7(8H)-yl]methanone DIPEA (0.710 ml, 4.07 mmol) in DMF (13.55 ml) was added to a stirred solution of 1-(6-chloroquinolin-4-yl)-3-methylpiperidine-4-carboxylic acid (0.413 g, 1.355 mmol), 3-(trifluoromethyl)-5,6,7,8-tetrahydro-[1,2,4]triazolo[4,3-a]pyrazine hydrochloride (0.310 g, 1.355 mmol) and HATU (0.773 g, 2.033 mmol). The reaction was stirred at room temperature for 15 h. The reaction mixture was diluted with EtOAc and washed with water 3×. The organic layers were dried with magnesium sulfate, filtered, concentrated and purified by silica gel chromatography (0-70% 3:1 EtOAc: EtOH in Hexane). The combined fractions were concentrated to give the title compound. MS: 479 (M+1). Human CYP8B1 IC50 (nM) 8.5.

Example 11a and 11b

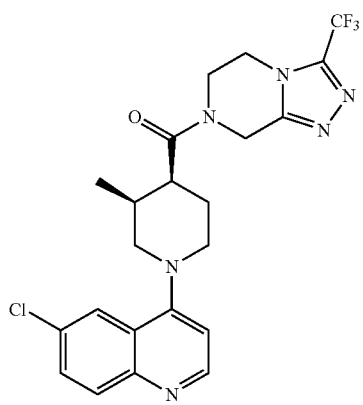

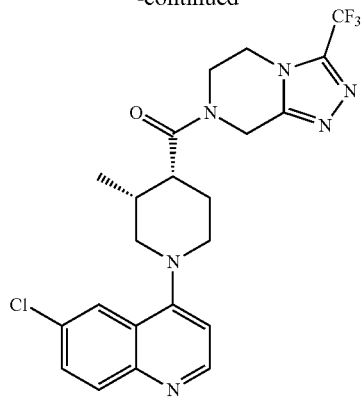

[(3S,4S)-1-(6-chloroquinolin-4-yl)-3-methylpiperidin-4-yl][3-(trifluoromethyl)-5,6-dihydro[1,2,4]triazolo[4,3-a]pyrazin-7(8H)-yl]methanone

[(3R,4R)-1-(6-chloroquinolin-4-yl)-3-methylpiperidin-4-yl][3-(trifluoromethyl)-5,6-dihydro[1,2,4]triazolo[4,3-a]pyrazin-7(8H)-yl]methanone

[1-(6-chloroquinolin-4-yl)-3-methylpiperidin-4-yl][3-(trifluoromethyl)-5,6-dihydro[1,2,4]triazolo[4,3-a]pyrazin-7(8H)-yl]methanone (264 mg, 0.55 mmol) was sent for SFC diastereomer separation. SFC separation (Column OD-H 25×0.46 cm, 35% ethanol (NH$_4$OH)/CO$_2$, 100 bar, 3 mL/min) afforded [(3S,4S)-1-(6-chloroquinolin-4-yl)-3-methylpiperidin-4-yl][3-(trifluoromethyl)-5,6-dihydro[1,2,4]triazolo[4,3-a]pyrazin-7(8H)-yl]methanone (MS: 479 (M+1) (peak 2, SFC t$_R$=5.15 min) Human CYP8B1 IC50 (nM) 3.5) and [(3R,4R)-1-(6-chloroquinolin-4-yl)-3-methylpiperidin-4-yl][3-(trifluoromethyl)-5,6-dihydro[1,2,4]triazolo[4,3-a]pyrazin-7(8H)-yl]methanone (MS: 479 (M+1) (peak 1, SFC t$_R$=4.03 min) Human CYP8B1 IC50 (nM) 1183).

Example 12

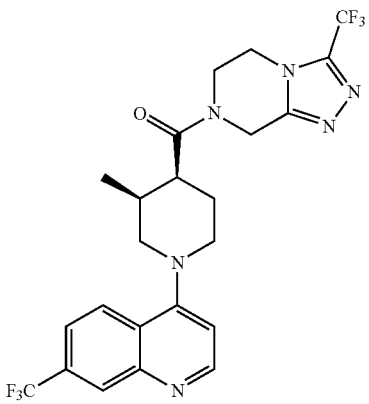 [SMILES: C[C@@H]1CN(c2ccnc3cc(C(F)(F)F)ccc23)CC[C@@H]1C(=O)N1CCn2c(nnc2C(F)(F)F)C1]

{(3S,4S)-3-methyl-1-[7-(trifluoromethyl)quinolin-4-yl]piperidin-4-yl}[3-(trifluoromethyl)-5,6-dihydro[1,2,4]triazolo[4,3-a]pyrazin-7(8H)-yl]methanone 4-chloro-7-(trifluoromethyl)quinoline (300 mg, 1.30 mmol), ((3S,4S)-3-methylpiperidin-4-yl)(3-(trifluoromethyl)-5,6-dihydro-[1,2,4]triazolo[4,3-a]pyrazin-7(8H)-yl) methanone hydrochloride (46 mg, 0.13 mmol), RuPhos Pd G2 (47 mg, 0.065 mmol) and cesium carbonate (1.27 g, 3.89 mmol) were combined in a sealed tube. 1,4-dioxane (12.95 ml) was added and purged with $N_2$ via subsurface bubbling for 5 min. The reaction was heated to 80° C. for 4 h. The reaction was concentrated and directly purified by silica gel chromatography (0-100% 3:1EtOAc:EtOH in hexanes). The combined fractions were concentrated and dried to give the title compound. MS: 513 (M+1). Human CYP8B1 IC50 (nM) 5.2.

Examples 13-32 were made using a similar synthesis to Example 12 substituting the appropriate reactants and reagents

| Example | Structure | Chemical Name | Exact Mass [M + H]+ | Human CYP8B1 IC50 (nM) |
|---|---|---|---|---|
| Example 13 | 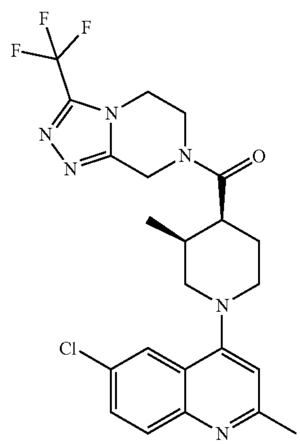 [SMILES: Cc1cc(N2CC[C@H](C(=O)N3CCn4c(nnc4C(F)(F)F)C3)[C@H](C)C2)c2cc(Cl)ccc2n1] | [(3S,4S)-1-(6-chloro-2-methylquinolin-4-yl)-3-methylpiperidin-4-yl][3-(trifluoromethyl)-5,6-dihydro[1,2,4]triazolo[4,3-a]pyrazin-7(8H)-yl]methanone | 493 | 3041 |
| Example 14 | 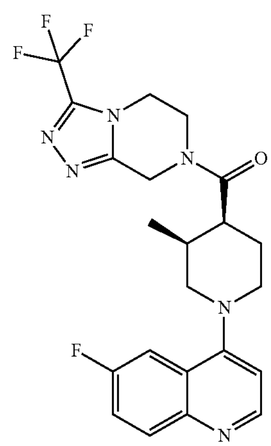 | [(3S,4S)-1-(6-fluoroquinolin-4-yl)-3-methylpiperidin-4-yl][3-(trifluoromethyl)-5,6-dihydro[1,2,4]triazolo[4,3-a]pyrazin-7(8H)-yl]methanone | 463 | 52 |
| Example 15 | 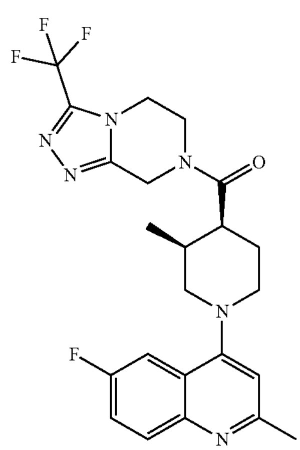 [SMILES: Cc1cc(N2CC[C@H](C(=O)N3CCn4c(nnc4C(F)(F)F)C3)[C@H](C)C2)c2cc(F)ccc2n1] | [(3S,4S)-1-(6-fluoro-2-methylquinolin-4-yl)-3-methylpiperidin-4-yl][3-(trifluoromethyl)-5,6-dihydro[1,2,4]triazolo[4,3-a]pyrazin-7(8H)-yl]methanone | 477 | 245 |

-continued

| Example | Structure | Chemical Name | Exact Mass [M + H]+ | Human CYP8B1 IC50 (nM) |
|---|---|---|---|---|
| Example 16 | 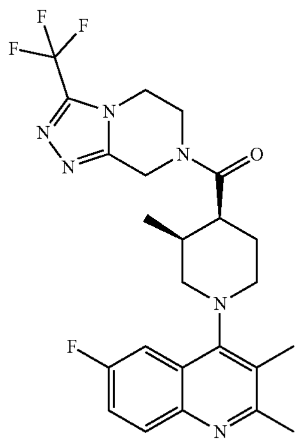 [SMILES: Cc1nc2ccc(F)cc2c(N2CC[C@H](C(=O)N3CCn4c(nnc4C(F)(F)F)C3)[C@H](C)C2)c1C] | [(3S,4S)-1-(6-fluoro-2,3-dimethylquinolin-4-yl)-3-methylpiperidin-4-yl][3-(trifluoromethyl)-5,6-dihydro[1,2,4]triazolo[4,3-a]pyrazin-7(8H)-yl]methanone | 491 | 37 |
| Example 17 | 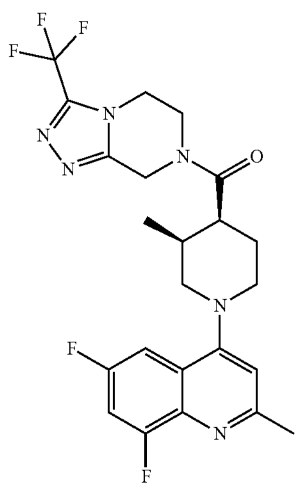 [SMILES: Cc1cc(N2CC[C@H](C(=O)N3CCn4c(nnc4C(F)(F)F)C3)[C@H](C)C2)c2cc(F)cc(F)c2n1] | [(3S,4S)-1-(6,8-difluoro-2-methylquinolin-4-yl)-3-methylpiperidin-4-yl][3-(trifluoromethyl)-5,6-dihydro[1,2,4]triazolo[4,3-a]pyrazin-7(8H)-yl]methanone | 495 | 145 |
| Example 18 | 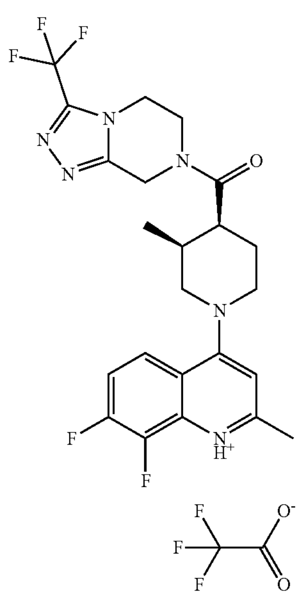 [SMILES: Cc1cc(N2CC[C@H](C(=O)N3CCn4c(nnc4C(F)(F)F)C3)[C@H](C)C2)c2ccc(F)c(F)c2[nH+]1 ; O=C([O-])C(F)(F)F] | 7,8-difluoro-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinolinium trifluoroacetate | 495 | 385 |

-continued
| Example | Structure | Chemical Name | Exact Mass [M + H]+ | Human CYP8B1 IC50 (nM) |
|---|---|---|---|---|
| Example 19 | 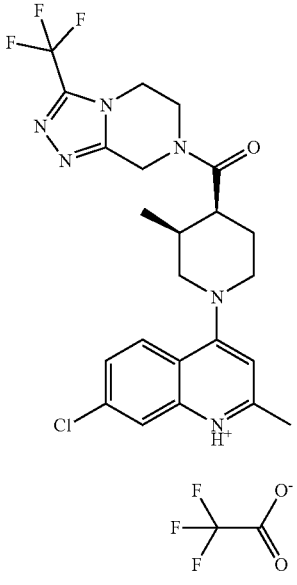 [SMILES: Cc1cc(N2CC[C@H](C(=O)N3CCn4c(nnc4C(F)(F)F)C3)[C@H](C)C2)c2ccc(Cl)cc2[nH+]1 ; O=C([O-])C(F)(F)F] | 7-chloro-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinolinium trifluoroacetate | 493 | 107 |
| Example 20 | 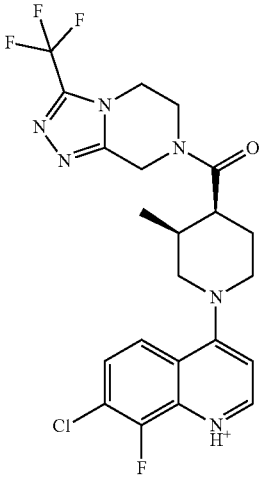 | 7-chloro-8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinolinium trifluoroacetate | 497 | 14 |

-continued

| Example | Structure | Chemical Name | Exact Mass [M + H]+ | Human CYP8B1 IC50 (nM) |
|---|---|---|---|---|
| Example 21 | 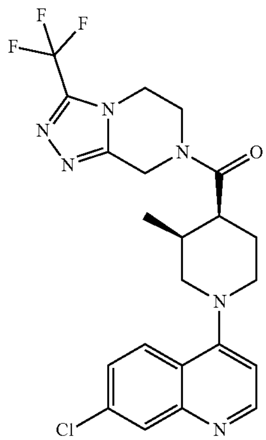 | [(3S,4S)-1-(7-chloroquinolin-4-yl)-3-methylpiperidin-4-yl][3-(trifluoromethyl)-5,6-dihydro[1,2,4]triazolo[4,3-a]pyrazin-7(8H)-yl]methanone | 479 | 6.3 |
| Example 22 | 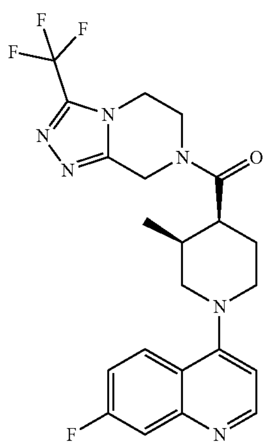 | [(3S,4S)-1-(7-fluoroquinolin-4-yl)-3-methylpiperidin-4-yl][3-(trifluoromethyl)-5,6-dihydro[1,2,4]triazolo[4,3-a]pyrazin-7(8H)-yl]methanone | 463 | 19 |
| Example 23 | 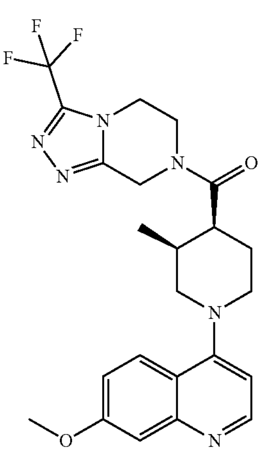 | [(3S,4S)-1-(7-methoxyquinolin-4-yl)-3-methylpiperidin-4-yl][3-(trifluoromethyl)-5,6-dihydro[1,2,4]triazolo[4,3-a]pyrazin-7(8H)-yl]methanone | 475 | 237 |

-continued

| Example | Structure | Chemical Name | Exact Mass [M + H]+ | Human CYP8B1 IC50 (nM) |
|---|---|---|---|---|
| Example 24 | 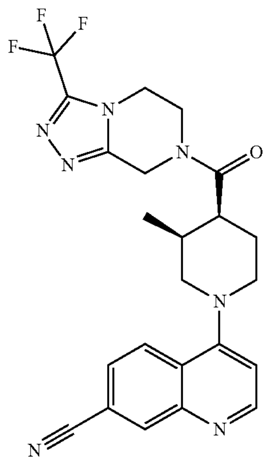 [SMILES: C[C@@H]1CN(c2ccnc3cc(C#N)ccc23)CC[C@@H]1C(=O)N1CCn2c(nnc2C(F)(F)F)C1] | 4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-7-carbonitrile | 470 | 8.4 |
| Example 25 | 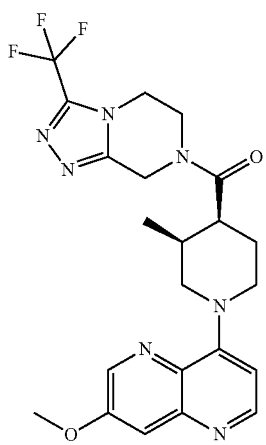 | [(3S,4S)-1-(7-methoxy-1,5-naphthyridin-4-yl)-3-methylpiperidin-4-yl][3-(trifluoromethyl)-5,6-dihydro[1,2,4]triazolo[4,3-a]pyrazin-7(8H)-yl]methanone | 476 | 307 |
| Example 26 | 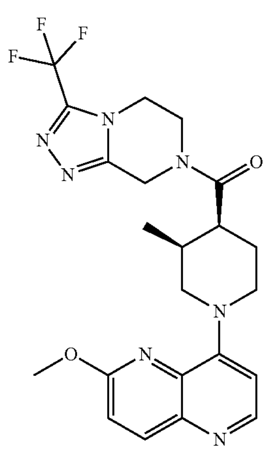 | [(3S,4S)-1-(6-methoxy-1,5-naphthyridin-4-yl)-3-methylpiperidin-4-yl][3-(trifluoromethyl)-5,6-dihydro[1,2,4]triazolo[4,3-a]pyrazin-7(8H)-yl]methanone | 476 | 18 |

-continued

| Example | Structure | Chemical Name | Exact Mass [M + H]+ | Human CYP8B1 IC50 (nM) |
|---|---|---|---|---|
| Example 27 | 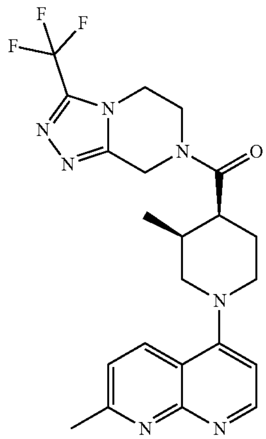 | [(3S,4S)-3-methyl-1-(7-methyl-1,8-naphthyridin-4-yl)piperidin-4-yl][3-(trifluoromethyl)-5,6-dihydro[1,2,4]triazolo[4,3-a]pyrazin-7(8H)-yl]methanone | 460 | 6697 |
| Example 28 | 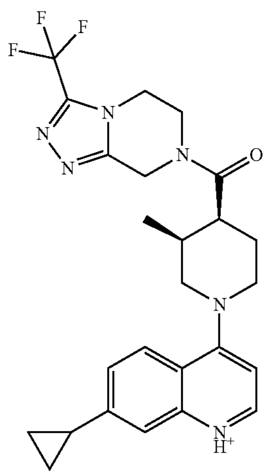 | 7-cyclopropyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinolinium chloride | 485 | 0.66 |
| Example 29 | 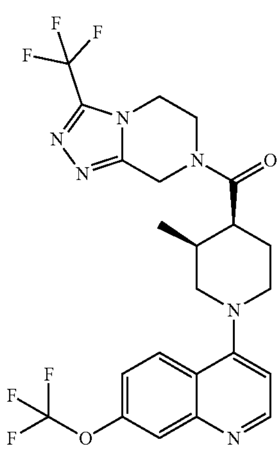 [SMILES: C[C@@H]1CN(c2ccnc3cc(OC(F)(F)F)ccc23)CC[C@@H]1C(=O)N1CCn2c(nnc2C(F)(F)F)C1] | {(3S,4S)-3-methyl-1-(7-(trifluoromethoxy)quinolin-4-yl]piperidin-4-yl}[3-(trifluoromethyl)-5,6-dihydro[1,2,4]triazolo[4,3-a]pyrazin-7(8H)-yl]methanone | 529 | 0.34 |

| Example | Chemical Name | Exact Mass [M + H]+ | Human CYP8B1 IC50 (nM) |
|---|---|---|---|
| Example 30 | {(3S,4S)-1-[7-(benzyloxy)quinolin-4-yl]-3-methyl]piperidin-4-yl}[3-(trifluoromethyl)-5,6-dihydro[1,2,4]triazolo[4,3-a]pyrazin-7(8H)-yl]methanone | 551 | 3.91 |
| Example 31 | {(3S,4S)-3-methyl-1-[7-(trifluoromethyl)-1,8-naphthyridin-4-yl]piperidin-4-yl}[3-(trifluoromethyl)-5,6-dihydro[1,2,4]triazolo[4,3-a]pyrazin-7(8H)-yl]methanone | 514 | 2695 |
| Example 32 | ((3S,4S)-1-(7,8-dichloroquinolin-4-yl)-3-methylpiperidin-4-yl)(3-(trifluoromethyl)-5,6-dihydro-[1,2,4]triazolo[4,3-a]pyrazin-7(8H)-yl)methanone | 513 | 111 |

Example 33

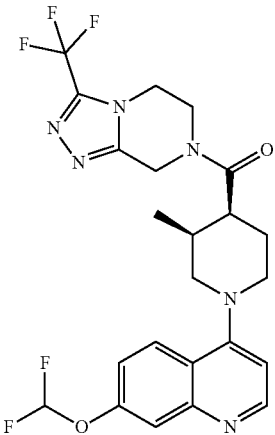 [SMILES: C[C@@H]1CN(c2ccnc3cc(OC(F)F)ccc23)CC[C@@H]1C(=O)N1CCn2c(nnc2C(F)(F)F)C1]

{(3S,4S)-1-[7-(difluoromethoxy)quinolin-4-yl]-3-methylpiperidin-4-yl}[3-(trifluoromethyl)-5,6-dihydro[1,2,4]triazolo[4,3-a]pyrazin-7(8H)-yl]methanone ((3S,4S)-1-(7-hydroxyquinolin-4-yl)-3-methylpiperidin-4-yl)(3-(trifluoromethyl)-5,6-dihydro-[1,2,4]triazolo[4,3-a]pyrazin-7(8H)-yl)methanone (0.220 g, 0.478 mmol), cesium carbonate (0.234 g, 0.717 mmol), sodium 2-chloro-2,2-difluoroacetate (0.109 g, 0.717 mmol), and DMF (4.78 ml) were combined in a sealed tube. The reaction was heated to 80° C. for 4 h. The reaction mixture was diluted with EtOAc and washed with water 3×. The organic layers were dried with magnesium sulfate, filtered, concentrated and purified by silica gel chromatography (0-100% 3:1 EtOAc:EtOH in Hexane). The combined fractions were concentrated to give the title compound. MS: 511 (M+1). Human CYP8B1 IC50 (nM) 8.30.

Example 34

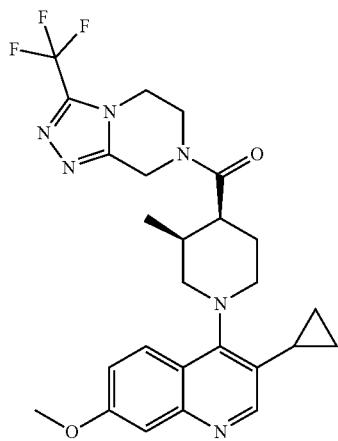 [SMILES: COc1ccc2c(N3CC[C@H](C(=O)N4CCn5c(nnc5C(F)(F)F)C4)[C@H](C)C3)c(C3CC3)cnc2c1]

[(3S,4S)-1-(3-cyclopropyl-7-methoxyquinolin-4-yl)-3-methylpiperidin-4-yl][3-(trifluoromethyl)-5,6-dihydro[1,2,4]triazolo[4,3-a]pyrazin-7(8H)-yl]methanone

[(3S,4S)-1-(3-bromo-7-methoxyquinolin-4-yl)-3-methylpiperidin-4-yl][3-(trifluoromethyl)-5,6-dihydro[1,2,4]triazolo[4,3-a]pyrazin-7(8H)-yl]methanone (33 mg, 0.06 mmol), cyclopropylboronic acid (7.68 mg, 0.089 mmol), Pd(OAc)$_2$ (1.34 mg, 5.96 μmol), tricyclohexylphosphine (1.67 mg, 5.96 μmol), potassium phosphate tribasic (1M in water, 0.12 mL, 0.12 mmol) and toluene (0.60 mL) were combined in a sealed tube. The reaction was purged with nitrogen gas for 5 minutes. The reaction was heated to 100° C. for 15 h. The reaction was cooled to room temperature, concentrated and directly purified by silica gel chromatography (0-100% 3:1 EtOAc:EtOH in Hexane). The combined fractions were concentrated to give the title compound. MS: 515 (M+1). Human CYP8B1 IC50 (nM) 0.67.

Example 35

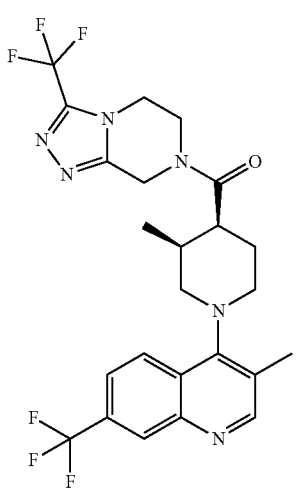 [SMILES: Cc1cnc2cc(C(F)(F)F)ccc2c1N1CC[C@H](C(=O)N2CCn3c(nnc3C(F)(F)F)C2)[C@H](C)C1]

{(3S,4S)-3-methyl-1-[3-methyl-7-(trifluoromethyl)quinolin-4-yl]piperidin-4-yl}[3-(trifluoromethyl)-5,6-dihydro[1,2,4]triazolo[4,3-a]pyrazin-7(8H)-yl]methanone {(3S,4S)-1-[3-iodo-7-(trifluoromethyl)quinolin-4-yl]-3-methylpiperidin-4-yl}[3-(trifluoromethyl)-5,6-dihydro[1,2,4]triazolo[4,3-a]pyrazin-7(81)-yl]methanone (50 mg, 0.078 mmol), 2,4,6-trimethyl-1,3,5,2,4,6-trioxatriborinane (0.016 mL, 0.117 mmol), Pd(Ph$_3$P)$_4$ (9.05 mg, 7.83 μmol), cesium cabonate (77 mg, 0.24 mmol) and DMF (0.78 mL) were combined in a sealed tube. The reaction was purged with nitrogen gas for 5 min and heated to 90° C. for 15 h. The reaction was cooled to room temperature and water was added. The aqueous layer was extracted with EtOAc (2×). The combined organic layers were dried with magnesium sulfate, filtered, concentrated and purified by silica gel chromatography. Fractions were combined and concentrated, then redissolved in 1 mL of DMF and purified by reverse phase HPLC (10-100% MeCN/Water, with 0.05% TFA). The fractions were combined and neutralized with saturated sodium bicarbonate. The aqueous layer was extracted with EtOAc (2×). The combined organic layers washed with water (1×). The organic layer was dried with magnesium sulfate, filtered and concentrated to give the title compound. MS: 527 (M+1). Human CYP8B1 IC50 (nM) 0.17.

Example 36

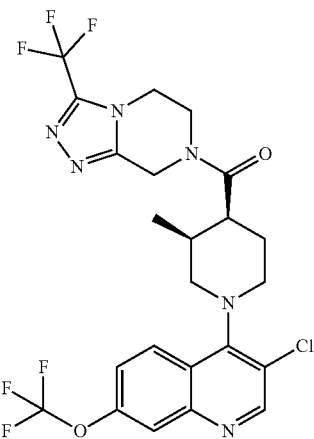 [SMILES: C[C@@H]1CN(c2c(Cl)cnc3cc(OC(F)(F)F)ccc23)CC[C@@H]1C(=O)N1CCn2c(nnc2C(F)(F)F)C1]

{(3S,4S)-1-[3-chloro-7-(trifluoromethoxy)quinolin-4-yl]-3-methylpiperidin-4-yl}[3-(trifluoromethyl)-5,6-dihydro[1,2,4]triazolo[4,3-a]pyrazin-7(8H)-yl]methanone {(3S,4S)-3-methyl-1-[7-(trifluoromethoxy)quinolin-4-yl]piperidin-4-yl}[3-(trifluoromethyl)-5,6-dihydro[1,2,4]triazolo[4,3-a]pyrazin-7(81)-yl]methanone (50 mg, 0.095 mmol) and N-chlorosuccinimide (15 mg, 0.11 mmol) were combined in a sealed tube. Acetonitrile (0.473 mL) was added and the mixture was stirred at 40° C. for 15 h. Water is added and the mixture was extracted with EtOAc (3×). The combined organics were dried with magnesium sulfate, filtered, concentrated and purified by silica gel chromatography (0-100% 3:1 EtOAc:EtOH in Hexane). The combined fractions were concentrated to afford the title compound. MS: 563 (M+1). Human CYP8B1 IC50 (nM) 0.35.

Example 37

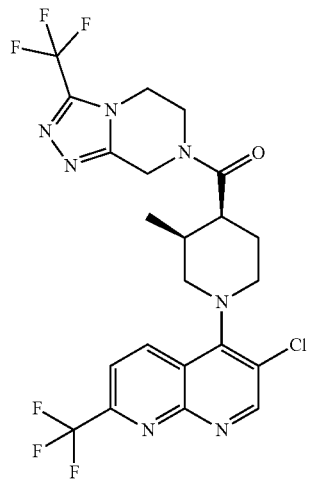 [SMILES: C[C@@H]1CN(c2c(Cl)cnc3nc(C(F)(F)F)ccc23)CC[C@@H]1C(=O)N1CCn2c(nnc2C(F)(F)F)C1]

{(3S,4S)-1-[3-chloro-7-(trifluoromethyl)-1,8-naphthyridin-4-yl]-3-methylpiperidin-4-yl}[3-(trifluoromethyl)-5,6-dihydro[1,2,4]triazolo[4,3-a]pyrazin-7(8H)-yl]methanone {(3S,4S)-1-[3-chloro-7-(trifluoromethyl)-1,8-naphthyridin-4-yl]-3-methylpiperidin-4-yl}[3-(trifluoromethyl)-5,6-dihydro[1,2,4]triazolo[4,3-a]pyrazin-7(8H)-yl]methanone was made using a similar synthesis as Example 36. MS: 548 (M+1). Human CYP8B1 IC50 (nM) 1.30.

Example 38

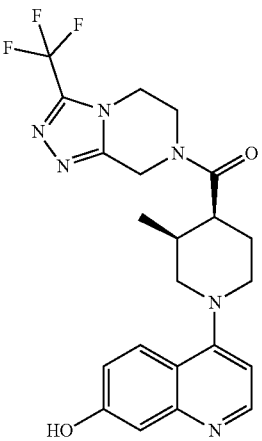

[(3S,4S)-1-(7-hydroxyquinolin-4-yl)-3-methylpiperidin-4-yl][3-(trifluoromethyl)-5,6-dihydro[1,2,4]triazolo[4,3-a]pyrazin-7(8H)-yl]methanone {(3S,4S)-1-[7-(benzyloxy)quinolin-4-yl]-3-methylpiperidin-4-yl}[3-(trifluoromethyl)-5,6-dihydro[1,2,4]triazolo[4,3-a]pyrazin-7(8H)-yl]methanone (299 mg, 0.54 mmol) was dissolved in MeOH (10.9 mL). 10% Pd—C (116 mg, 0.11 mmol) was added and the reaction was placed on a shaker under an atmosphere of hydrogen gas at room temperature and 50 psi for 15 h. The reaction was filtered through CELITE. The filter cake was washed with MeOH and concentrated to afford the title compound. MS: 461 (M+1). Human CYP8B1 IC50 (nM) 2888.

Example 39

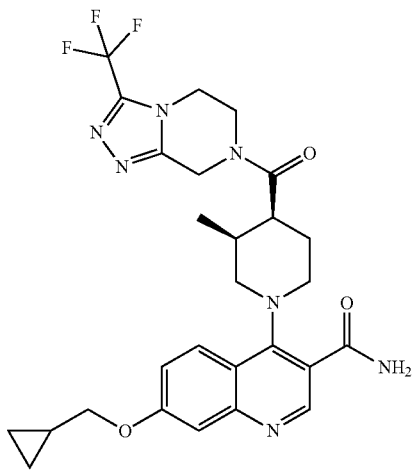 [SMILES: C[C@@H]1CN(c2c(C(N)=O)cnc3cc(OCC4CC4)ccc23)CC[C@@H]1C(=O)N1CCn2c(nnc2C(F)(F)F)C1]

7-(cyclopropylmethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carboxamide 7-(cyclopropylmethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile (188 mg, 0.33 mmol) and potassium carbonate (135 mg, 0.98 mmol) were combined with DMSO (6.53 mL). Hydrogen peroxide (143 mL, 1.63 mmol) was added and the mixture was stirred at room temperature for 5 h. Additional hydrogen peroxide (143 mL, 1.63 mmol) was added and the mixture continued to be stirred at room temperature for 15 h. The mixture was filtered and purified by reverse phase HPLC (10-100% MeCN/Water, with 0.05% TFA). The fractions were combined and neutralized with saturated sodium bicarbonate and then extracted 3× with EtOAc. The organic layers were washed with water (1×), dried with magnesium sulfate, filtered, and concentrated to afford the title compound. MS: 558 (M+1). Human CYP8B1 IC50 (nM) 5.29.

Examples 40

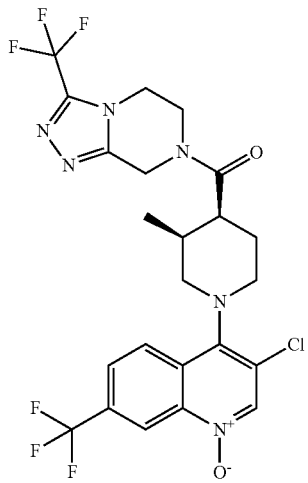 [SMILES: C[C@@H]1CN(c2c(Cl)c[n+]([O-])c3cc(C(F)(F)F)ccc23)CC[C@@H]1C(=O)N1CCn2c(nnc2C(F)(F)F)C1]

{(3S,4S)-1-[3-chloro-1-oxido-7-(trifluoromethyl) quinolin-4-yl]-3-methylpiperidin-4-yl}[3-(trifluoromethyl)-5,6-dihydro[1,2,4]triazolo[4,3-a]pyrazin-7 (8H)-yl]methanone ((3S,4S)-1-(3-chloro-7-(trifluoromethyl)quinolin-4-yl)-3-methylpiperidin-4-yl)(3-(trifluoromethyl)-5,6-dihydro-[1,2,4]triazolo[4,3-a]pyrazin-7(8H)-yl)methanone hydrochloride (0.050 g, 0.086 mmol) was free based by dissolving in DCM and neutralizing with saturated sodium bicarbonate. The organic layer was dried with magnesium sulfate, filtered, and concentrated. To the residue was added DCM (1.714 ml) followed by mCPBA (0.022 g, 0.129 mmol). The reaction was stirred at room temperature for 15 h. Added another 1.5 eq. of mCPBA and stirred at room temperature for 15 h. Saturated sodium thiosulfate was added and the reaction stirred for 30 min. The aqueous layer was extracted 3× with EtOAc. The combined organic layers were dried with magnesium sulfate, filtered and concentrated. The residue was taken up in DMF and purified by reverse phase chromatography (10-100% MeCN/Water, with 0.05% TFA). The combined fractions were neutralized with saturated sodium bicarbonate and extracted 3× with EtOAc. The organic layers were washed with water, dried with magnesium sulfate, filtered, and concentrated to give the title compound. MS: 563 (M+1). Human CYP8B1 IC50 (nM) 0.80.

Example 41

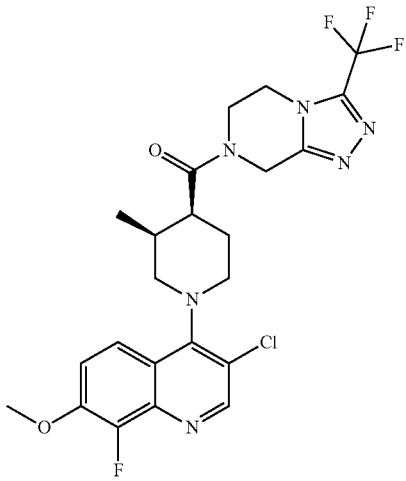 [SMILES: COc1ccc2c(N3CC[C@H](C(=O)N4CCn5c(nnc5C(F)(F)F)C4)[C@H](C)C3)c(Cl)cnc2c1F]

[(3S,4S)-1-(3-chloro-8-fluoro-7-methoxyquinolin-4-yl)-3-methylpiperidin-4-yl][3-(trifluoromethyl)-5,6-dihydro[1,2,4]triazolo[4,3-a]pyrazin-7(8H)-yl] methanone

[(3S,4S)-3-methylpiperidin-4-yl][3-(trifluoromethyl)-5,6-dihydro[1,2,4]triazolo[4,3-a]pyrazin-7(8H)-yl]methanone (38.7 mg, 0.122 mmol) was added to a stirred mixture of 3,4-dichloro-8-fluoro-7-methoxyquinoline (20 mg, 0.081 mmol) and DIEA (0.043 mL, 0.244 mmol) in NMP (0.3 mL). The mixture was stirred at 130° C. for 16 h. The reaction mixture was purified by prep-HPLC (Water/MeCN) then dried by lyophilization to give the title compound. MS: 527 (M+1). Human CYP8B1 IC50 (nM) 0.38.

Example 42

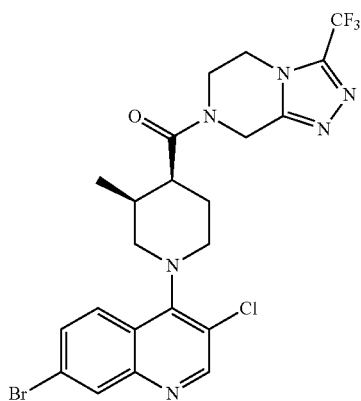

[(3S,4S)-1-(7-bromo-3-chloroquinolin-4-yl)-3-methylpiperidin-4-yl][3-(trifluoromethyl)-5,6-dihydro[1,2,4]triazolo[4,3-a]pyrazin-7(81)-yl]methanone

[(3S,4S)-3-methylpiperidin-4-yl][3-(trifluoromethyl)-5,6-dihydro[1,2,4]triazolo[4,3-a]pyrazin-7(8H)-yl]methanone (70 mg, 0.221 mmol) was added to a stirred mixture of 7-bromo-3,4-dichloroquinoline (61.1 mg, 0.221 mmol) and DIEA (0.116 mL, 0.662 mmol) in NMP (0.5 mL). The mixture was stirred at 200° C. for 2 h. Water (20 mL) was added to the reaction mixture then extracted with EtOAc (10 mL*2). The combined organic layers was washed with saturated aqueous solution of NaCl and then dried over $Na_2SO_4$, filtered and concentrated. The residue was purified by prep-TLC (EtOAc:PE=1:1) to give the title compound. MS: 559 (M+1). Human CYP8B1 IC50 (nM) 0.44.

Example 43

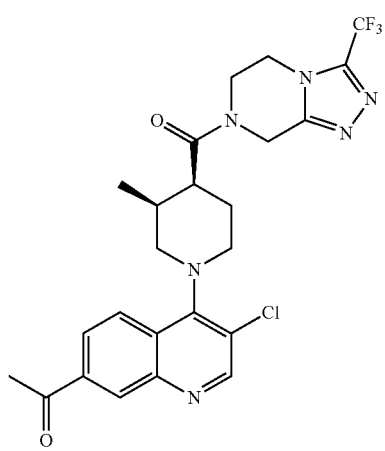 [SMILES: CC(=O)c1ccc2c(N3CC[C@H](C(=O)N4CCn5c(nnc5C(F)(F)F)C4)[C@H](C)C3)c(Cl)cnc2c1]

1-{3-chloro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinolin-7-yl}ethanone A mixture of tributyl (1-ethoxyvinyl) tin (42.1 µL, 0.125 mmol), [(3S,4S)-1-(7-bromo-3-chloroquinolin-4-yl)-3-methylpiperidin-4-yl][3-(trifluoromethyl)-5,6-dihydro[1,2,4]triazolo[4,3-a]pyrazin-7(8H)-yl]methanone (63.2 mg, 0.113 mmol), [1,1'-bis(diphenylphosphino)ferrocene]dichloropalladium (II) (8.29 mg, 0.011 mmol) and toluene (378 µL) was purged with $N_2$, then heated to 110° C. under $N_2$ atmosphere for 2 h. The mixture was cooled to room temperature then a solution of HCl:THF (1:1; 3 mL) was added to the reaction mixture and stirred vigorously at room temperature. The reaction mixture was extracted with EtOAc (10 mL×3). The combined organic layers was washed with saturated aqueous solution of NaCl (20 mL) then dried over $Na_2SO_4$, filtered and concentrated. The residue was purified by prep-HPLC (Phenomenex Gemini C18 250*21.2 mm*5 um, Mobile phase A: water (10 mM $NH_4HCO_3$); Mobile phase B: acetonitrile) then dried by lyophilization to the title compound. MS: 521 (M+1). Human CYP8B1 IC50 (nM) 0.28.

Example 44a and 44b

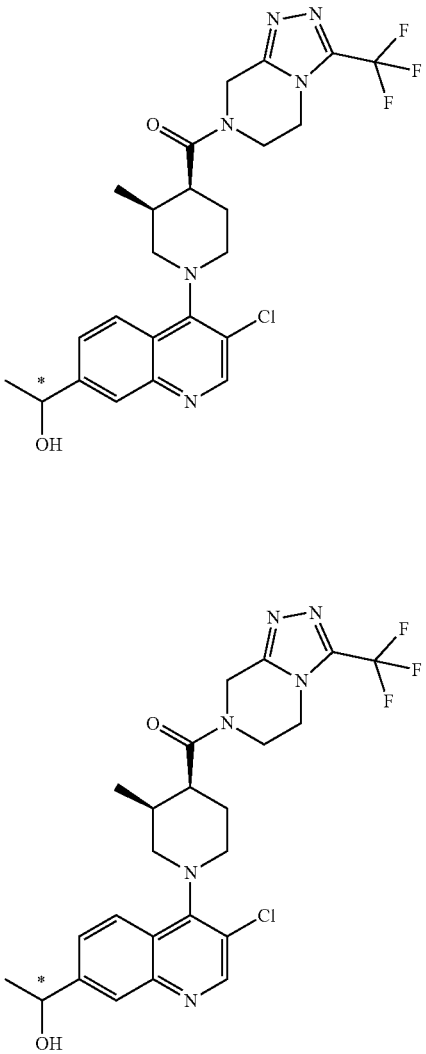

[(3S,4S)-1-{3-chloro-7-[(1S)-1-hydroxyethyl]quinolin-4-yl}-3-methylpiperidin-4-yl][3-(trifluoromethyl)-5,6-dihydro[1,2,4]triazolo[4,3-a]pyrazin-7(8H)-yl]methanone

[(3S,4S)-1-{3-chloro-7-[(1R)-1-hydroxyethyl]quinolin-4-yl}-3-methylpiperidin-4-yl][3-(trifluoromethyl)-5,6-dihydro[1,2,4]triazolo[4,3-a]pyrazin-7(8H)-yl]methanone NaBH₄ (2.90 mg, 0.077 mmol) was added to a solution of 1-{3-chloro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinolin-7-yl}ethanone (20 mg, 0.038 mmol) in MeOH (0.2 mL) at 25° C. The mixture was stirred at 25° C. for 2 h. The mixture was diluted with water (20 mL) and extracted with EtOAc (10 mL×3). The organic layer was washed with brine (20 mL), dried over Na₂SO₄, filtered and concentrated. The residue was purified by prep-TLC (DCM:MeOH=20:1) to afford racemic {(3S,4S)-1-[3-chloro-7-(1-hydroxyethyl)quinolin-4-yl]-3-methylpiperidin-4-yl}[3-(trifluoromethyl)-5,6-dihydro[1,2,4]triazolo[4,3-a]pyrazin-7(8H)-yl]methanone. The racemic mixture was separated by SFC was separated by SFC (Method; Column AD (250 mm*30 mm, 10 um); Condition Base-ETOH; Begin B 45%; End B 45%; Gradient Time (min); 100% B; FlowRate(mL/min) 80 mL/min; Injections 60) to afford Peak 1 (MS: 523 (M+1). Human CYP8B1 IC50 (nM) 0.34) and Peak 2 (MS: 523 (M+1). Human CYP8B1 IC50 (nM) 1.2).

Example 45

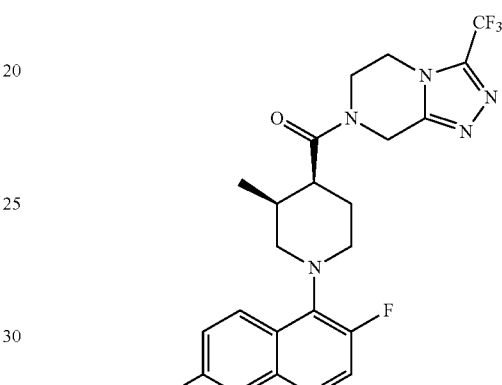

{(3S,4S)-1-[3-fluoro-7-(trifluoromethyl)quinolin-4-yl]-3-methylpiperidin-4-yl}[3-(trifluoromethyl)-5,6-dihydro[1,2,4]triazolo[4,3-a]pyrazin-7(8H)-yl]methanone 3-fluoro-4-iodo-7-(trifluoromethyl)quinoline (339 mg, 0.994 mmol), ((3S,4S)-3-methylpiperidin-4-yl)(3-(trifluoromethyl)-5,6-dihydro-[1,2,4]triazolo[4,3-a]pyrazin-7(8H)-yl) methanone hydrochloride (369 mg, 1.044 mmol), RuPhos Pd G2 (36 mg, 0.050 mmol) and cesium carbonate (972 mg, 2.98 mmol) were combined in a sealed tube. 1,4-Dioxane (9.94 ml) was added and the mixture was purged with N₂ for 5 min. The reaction was heated to 80° C. for 15 h. Additional ((3S,4S)-3-methylpiperidin-4-yl)(3-(trifluoromethyl)-5,6-dihydro-[1,2,4]triazolo[4,3-a]pyrazin-7(8H)-yl) methanone hydrochloride (105 mg, 0.31 mmol) was added. The reaction was diluted with water and extracted with EtOAc (3×). The combined organic layers were dried with magnesium sulfate, filtered and concentrated. The residue was purified by silica gel chromatography (0-100% 3:1EtOAc:EtOH in Hexane). The combined fractions were concentrated under reduced pressure and dried to afford the title compound. MS: 531 (M+1). Human CYP8B1 IC50 (nM) 0.25.

Example 46

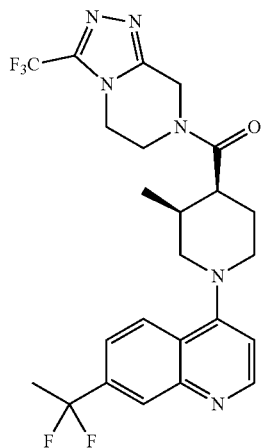 [SMILES: C[C@@H]1CN(c2ccnc3cc(C(C)(F)F)ccc23)CC[C@@H]1C(=O)N1CCn2c(nnc2C(F)(F)F)C1]

{(3S,4S)-1-[7-(1,1-difluoroethyl)quinolin-4-yl]-3-methylpiperidin-4-yl}[3-(trifluoromethyl)-5,6-dihydro[1,2,4]triazolo[4,3-a]pyrazin-7(8H)-yl]methanone ((3S,4S)-3-methylpiperidin-4-yl)(3-(trifluoromethyl)-5,6-dihydro-[1,2,4]triazolo[4,3-a]pyrazin-7(8H)-yl)methanone (181 mg, 0.571 mmol) was added to a stirred mixture of 4-chloro-7-(1,1-difluoroethyl)quinoline (100 mg, 0.439 mmol), 1,4-diazabicyclo[2.2.2]octane (49.3 mg, 0.439 mmol) and DIEA (0.230 mL, 1.318 mmol) in NMP (1 mL). The mixture was stirred at 180° C. for 70 min. The mixture was diluted with water (50 mL) and extracted with EtOAc (30 mL×3). The organic layer was washed with brine (30 mL), dried over $Na_2SO_4$, filtered and concentrated. The residue was purified by p-TLC (DCM:MeOH=15:1) to afford the title compound. MS: 509 (M+1). Human CYP8B1 IC50 (nM) 1.1

Example 47

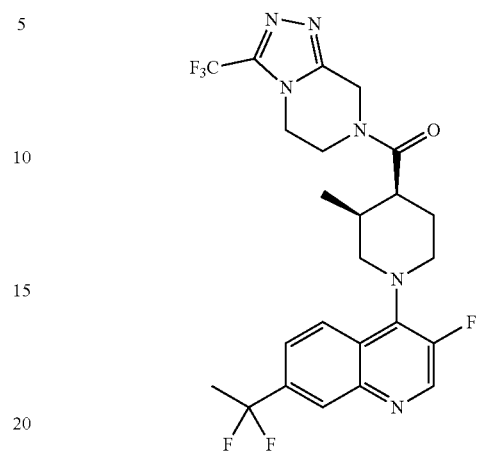

{(3S,4S)-1-[7-(1,1-difluoroethyl)-3-fluoroquinolin-4-yl]-3-methylpiperidin-4-yl}[3-(trifluoromethyl)-5,6-dihydro[1,2,4]triazolo[4,3-a]pyrazin-7(8H)-yl]methanone A mixture of Selectfluor (69.7 mg, 0.197 mmol) and {(3S,4S)-1-[7-(1,1-difluoroethyl)quinolin-4-yl]-3-methylpiperidin-4-yl}[3-(trifluoromethyl)-5,6-dihydro[1,2,4]triazolo[4,3-a]pyrazin-7(8H)-yl]methanone (100 mg, 0.197 mmol) in acetonitrile (1 mL) was stirred at 25° C. for 2 h. The mixture was purified by p-TLC (DCM:MeOH=20:1) to afford a crude product. The crude product was purified by p-HPLC (water (10 mM $NH_4HCO_3$)-MeCN) to afford the title compound. MS: 527 (M+1). Human CYP8B1 IC50 (nM) 0.57.

Example 48 was made using a similar synthesis to Example 47 substituting the appropriate reactants and reagents.

| Example | Structure | Chemical Name | Exact Mass [M + H]+ | Human CYP8B1 IC50 (nM) |
|---|---|---|---|---|
| 48 | ![structure] | [(3S,4S)-1-(7-chloro-3-fluoroquinolin-4-yl)-3-methylpiperidin-4-yl][3-(trifluoromethyl)-5,6-dihydro[1,2,4]triazolo[4,3-a]pyrazin-7(8H)-yl]methanone | 497 | 1.7 |

Example 49

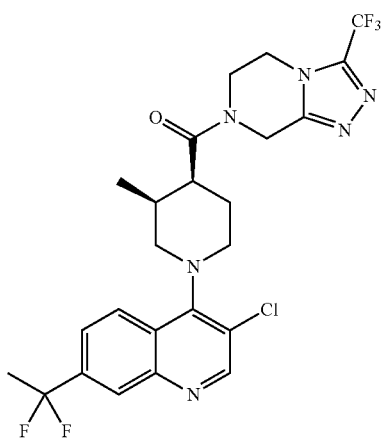 [SMILES: C[C@@H]1CN(c2c(Cl)cnc3cc(C(C)(F)F)ccc23)CC[C@@H]1C(=O)N1CCn2c(nnc2C(F)(F)F)C1]

{(3S,4S)-1-[3-chloro-7-(1,1-difluoroethyl)quinolin-4-yl]-3-methylpiperidin-4-yl}[3-(trifluoromethyl)-5,6-dihydro[1,2,4]triazolo[4,3-a]pyrazin-7(8H)-yl]methanone A mixture of {(3S,4S)-1-[7-(1,1-difluoroethyl)quinolin-4-yl]-3-methylpiperidin-4-yl}[3-(trifluoromethyl)-5,6-dihydro[1,2,4]triazolo[4,3-a]pyrazin-7(8H)-yl]methanone (20 mg, 0.039 mmol) and NCS (15.76 mg, 0.118 mmol) in acetonitrile (0.05 mL) and i-PrOH (0.15 mL) was stirred at 25° C. for 16 h. The mixture was filtered and purified by p-HPLC (water (10 mM $NH_4HCO_3$)-MeCN) to give the title compound. MS: 543 (M+1). Human CYP8B1 IC50 (nM) 0.46.

Examples 50-51 were made using a similar synthesis to Example 49 substituting the appropriate reactants and reagents.

| Example | Structure | Chemical Name | Exact Mass [M + H]+ | Human CYP8B1 IC50 (nM) |
|---|---|---|---|---|
| 50 | 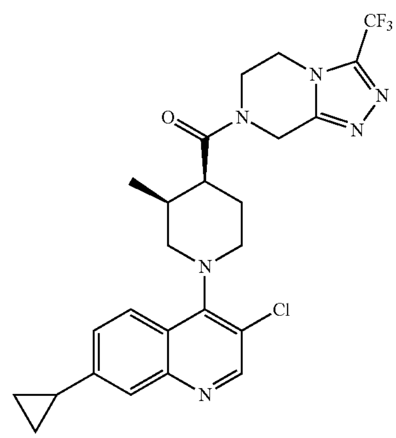 [SMILES: C[C@@H]1CN(c2c(Cl)cnc3cc(C4CC4)ccc23)CC[C@@H]1C(=O)N1CCn2c(nnc2C(F)(F)F)C1] | [(3S,4S)-1-(3-chloro-7-cyclopropyl-quinolin-4-yl)-3-methylpiperidin-4-yl][3-(trifluoromethyl)-5,6-dihydro[1,2,4]triazolo[4,3-a]pyrazin-7(8H)-yl]methanone | 519 | 0.25 |
| 51 | 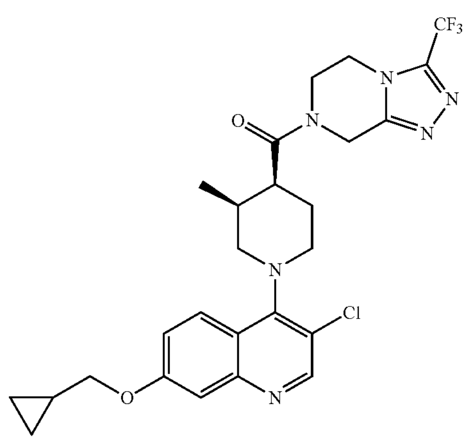 [SMILES: C[C@@H]1CN(c2c(Cl)cnc3cc(OCC4CC4)ccc23)CC[C@@H]1C(=O)N1CCn2c(nnc2C(F)(F)F)C1] | [(3S,4S)-1-(3-chloro-7-cyclopropyl-quinolin-4-yl)-3-methylpiperidin-4-yl][3-(trifluoromethyl)-5,6-dihydro[1,2,4]triazolo[4,3-a]pyrazin-7(8H)-yl]methanone | 549 | 0.22 |

Example 52

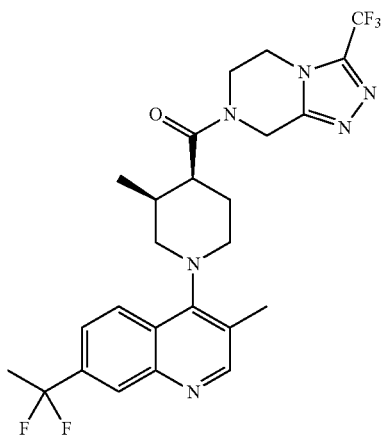 [SMILES: Cc1cnc2cc(C(C)(F)F)ccc2c1N1CC[C@H](C(=O)N2CCn3c(nnc3C(F)(F)F)C2)[C@H](C)C1]

{(3S,4S)-1-[7-(1,1-difluoroethyl)-3-methylquinolin-4-yl]-3-methylpiperidin-4-yl}[3-(trifluoromethyl)-5,6-dihydro[1,2,4]triazolo[4,3-a]pyrazin-7(8H)-yl]methanone A mixture of {(3S,4S)-1-[3-bromo-7-(1,1-difluoroethyl)quinolin-4-yl]-3-methylpiperidin-4-yl}[3-(trifluoromethyl)-5,6-dihydro[1,2,4]triazolo[4,3-a]pyrazin-7(8H)-yl]methanone (20 mg, 0.034 mmol), $Cs_2CO_3$ (33.3 mg, 0.102 mmol), 2,4,6-trimethyl-1,3,5,2,4,6-trioxatriborinane (8.55 mg, 0.068 mmol) and palladium tetrakis (3.93 mg, 3.40 μmol) in DMF (0.34 mL) was stirred at 90° C. for 16 h under $N_2$. The mixture was diluted with brine (2 drops), filtered and purified by p-HPLC (water(10 mM $NH_4HCO_3$)-MeCN) to afford the title compound. MS: 523 (M+1). Human CYP8B1 IC50 (nM) 0.31.

Example 53

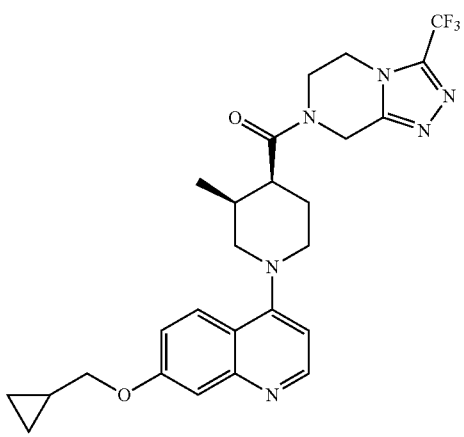 [SMILES: C[C@@H]1CN(c2ccnc3cc(OCC4CC4)ccc23)CC[C@@H]1C(=O)N1CCn2c(nnc2C(F)(F)F)C1]

{(3S,4S)-1-[7-(cyclopropylmethoxy)quinolin-4-yl]-3-methylpiperidin-4-yl}[3-(trifluoromethyl)-5,6-dihydro[1,2,4]triazolo[4,3-a]pyrazin-7(8H)-yl]methanone ((3S,4S)-3-methylpiperidin-4-yl)(3-(trifluoromethyl)-5,6-dihydro-[1,2,4]triazolo[4,3-a]pyrazin-7(8H)-yl)methanone hydrochloride (128 mg, 0.362 mmol) was added to a stirred mixture of 4-chloro-7-(cyclopropylmethoxy)quinoline (77 mg, 0.329 mmol) and DIEA (0.115 mL, 0.659 mmol) in NMP (1 mL), the mixture was stirred at 170° C. for 30 min. The mixture was cooled to room temperature. Water (30 mL) was added to the reaction mixture then extracted with EtOAc (10 mL×3). The combined organic layers was washed with saturated aqueous solution of NaCl (30 mL) then dried over $Na_2SO_4$, filtered and concentrated. The residue was purified by p-TLC ($SiO_2$, DCM:MeOH=40:1) to give product. The product was purified by prep-HPLC (Neutral condition) then dried by lyophilization to give the title compound. MS: 515 (M+1). Human CYP8B1 IC50 (nM) 3.6.

Example 54

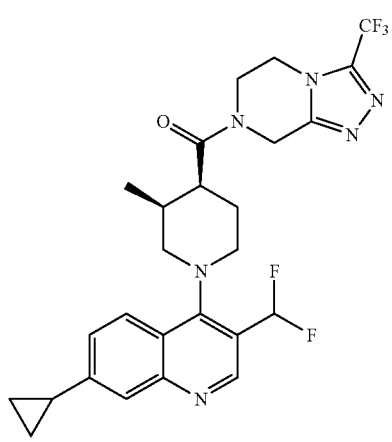 [SMILES: C[C@@H]1CN(c2c(C(F)F)cnc3cc(C4CC4)ccc23)CC[C@@H]1C(=O)N1CCn2c(nnc2C(F)(F)F)C1]

{(3S,4S)-1-[7-cyclopropyl-3-(difluoromethyl)quinolin-4-yl]-3-methylpiperidin-4-yl}[3-(trifluoromethyl)-5,6-dihydro[1,2,4]triazolo[4,3-a]pyrazin-7(81H)-yl]methanone BAST (0.075 mL, 0.406 mmol), followed by EtOH (2.370 μL, 0.041 mmol) was added to a stirred solution of 7-cyclopropyl-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbaldehyde (104 mg, 0.203 mmol) in DCM (3 mL) at 0° C., under a nitrogen atmosphere. The reaction mixture was allowed to warm to 25° C. and stirred for 3 h. Additional BAST (0.075 mL, 0.406 mmol) was added to the mixture at 25° C. and stirred for 16 h. The reaction mixture was diluted with DCM (15 mL) and then quenched with saturated $NaHCO_3$ solution (20 mL). The separated aqueous layer was extracted with DCM (3×8 mL). The combined organic layers were dried with $Na_2SO_4$, filtered and concentrated. The residue was purified by prep-HPLC (water (10 mM $NH_4HCO_3$) and acetonitrile) then dried by lyophilization to give the title compound. MS: 535 (M+1). Human CYP8B1 IC50 (nM) 0.61.

Example 55

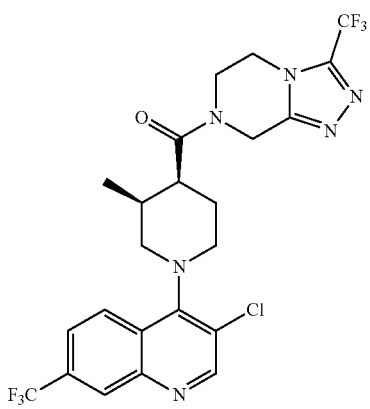

((3S,4S)-1-(3-chloro-7-(trifluoromethyl)quinolin-4-yl)-3-methylpiperidin-4-yl)(3-(trifluoromethyl)-5,6-dihydro-[1,2,4]triazolo[4,3-a]pyrazin-7(8H)-yl)methanone ((3S,4S)-3-methyl-1-(7-(trifluoromethyl)quinolin-4-yl)piperidin-4-yl)(3-(trifluoromethyl)-5,6-dihydro-[1,2,4]triazolo[4,3-a]pyrazin-7(8H)-yl)methanone (11.5 g, 22 mmol) in acetonitrile (100 ml) was treated with NCS (4.2 g, 31 mmol) and the mixture was stirred at 40° C. for 12 h. The reaction was cooled and the solvent was removed under reduced pressure. The residue was purified by MPLC (SiO$_2$; 0->100% (3:1 EtOAc:EtOH):hexanes) to provide ((3S,4S)-1-(3-chloro-7-(trifluoromethyl)quinolin-4-yl)-3-methylpiperidin-4-yl)(3-(trifluoromethyl)-5,6-dihydro-[1,2,4]triazolo[4,3-a]pyrazin-7(8H)-yl)methanone. MS: 547 (M+1). Human CYP8B1 IC50 (nM) 0.2.

Example 56

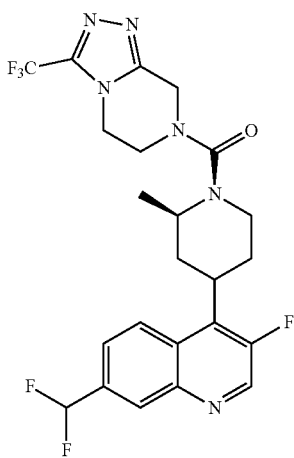

((3S,4S)-1-(7-(difluoromethyl)-3-fluoroquinolin-4-yl)-3-methylpiperidin-4-yl)(3-(trifluoromethyl)-5,6-dihydro-[1,2,4]triazolo[4,3-a]pyrazin-7(8H)-yl)methanone Tributyl(vinyl)tin (4.46 ml, 12.72 mmol) and Pd(Ph3P)4 (1278 mg, 1.106 mmol) was added to a solution of 7-bromo-3-fluoroquinoline (2500 mg, 11.06 mmol) in 1,4-Dioxane (15 ml). The mixture was heated to 105° C. and stirred overnight. The mixture was filtered through a CELITE pad to remove the solids. The filtrate was washed with ethyl acetate and the combined filtrate was concentrated in vacuo. The residue was purified by column chromatography on silica gel, eluted with 0-2% MeOH/DCM to give 3-fluoro-7-vinylquinoline. MS: 174 (M+1).

BuLi (2.5M in hexane) (4.43 ml, 11.09 mmol) was added to a solution of diisopropylamine (1.554 ml, 11.09 mmol) in THF (20 ml) at −78° C. The mixture was stirred at −78° C. for 30 min then was slowly added to a solution of 3-fluoro-7-vinylquinoline (1600 mg, 9.24 mmol) in THF (20 ml) (precooled to −78° C.). The resulting mixture was stirred at −78° C. for 90 min, followed by addition of a solution of I$_2$ (2814 mg, 11.09 mmol) in THF (20 ml). The stirring continued at −78° C. for 2 h, then warmed to 0° C. The resulting mixture was worked up with saturated NH$_4$Cl, extracted with ethyl acetate, dried over Na$_2$SO$_4$, filtered and concentrated in vacuo. The residue was purified by column chromatography on silica gel, eluted with 0-2% MeOH/DCM to give 3-fluoro-4-iodo-7-vinylquinoline. MS: 300 (M+1).

Water (1.5 ml), osmium(VIII) oxide(2.5% in t-BuOH) (1.190 ml, 0.117 mmol), 2,6-dimethylpyridine (1.090 ml, 9.36 mmol) and sodium periodate (4005 mg, 18.72 mmol) were sequentially added to a solution of 3-fluoro-4-iodo-7-vinylquinoline (1400 mg, 4.68 mmol) in 1,4-dioxane (6 ml). The reaction mixture was stirred for 2 h at room temperature, quenched by adding H$_2$O (20 mL), and extracted two times with DCM (2×20 mL). The combined organic layers were dried over MgSO$_4$, concentrated, and purified by silica gel chromatography (hexanes/EtOAc 100:0 to 50:50 gradient) to afford 3-fluoro-4-iodoquinoline-7-carbaldehyde.

DAST (0.625 ml, 4.73 mmol) was added to a solution of 3-fluoro-4-iodoquinoline-7-carbaldehyde (950 mg, 3.16 mmol) in CH$_2$Cl$_2$ (8 ml) at 0° C. The mixture was stirred at 0° C. for 1 h, then at room temperature overnight. The resulting mixture was concentrated in vacuo.

The residue was purified by column chromatography on silica gel, eluted with 0-20% ethyl acetate/hexane to give 7-(difluoromethyl)-3-fluoro-4-iodoquinoline. MS: 324 (M+1). 2$^{nd}$ generation RuPhos precatalyst (183 mg, 0.235 mmol) was added to a solution of ((3S,4S)-3-methylpiperidin-4-yl)(3-(trifluoromethyl)-5,6-dihydro-[1,2,4]triazolo[4,3-a]pyrazin-7(8H)-yl)methanone, HCl (1196 mg, 3.38 mmol), 7-(difluoromethyl)-3-fluoro-4-iodoquinoline (950 mg, 2.94 mmol) and Cs$_2$CO$_3$ (2874 mg, 8.82 mmol) in 1,4-Dioxane (2 ml). The mixture was heated to 90° C. and stirred overnight. The mixture was then concentrated in vacuo. The residue was purified by column chromatography on silica gel, eluted with 0-5% MeOH/DCM to give as a solid which was dissolved in MeOH (2 ml). 1 ml 1N HCl in diethyl ether was added to the mixture and stirred for 20 min. The mixture was further concentrated in vacuo to give ((3S,4S)-1-(7-(difluoromethyl)-3-fluoroquinolin-4-yl)-3-methylpiperidin-4-yl)(3-(trifluoromethyl)-5,6-dihydro-[1,2,4]triazolo[4,3-a]pyrazin-7(8H)-yl)methanone, HCl. MS: 513 (M+1). Human CYP8B1 IC50 (nM) 0.46.

Example 57 was made using a similar synthesis to Example 56 substituting the appropriate reactants and reagents.

| Example | Structure | Chemical Name | Exact Mass [M + H]+ | Human CYP8B1 IC50 (nM) |
|---|---|---|---|---|
| 57 | 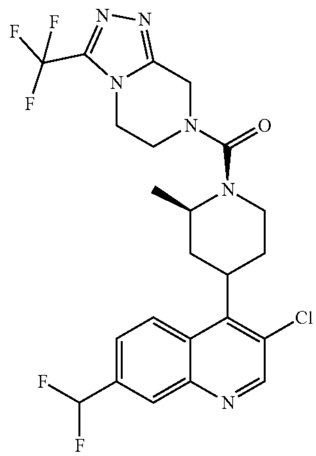 | ((2R)-4-(3-chloro-7-(difluoromethyl)quinolin-4-yl)-2-methylpiperidin-1-yl)(3-(trifluoromethyl)-5,6-dihydro-[1,2,4]triazolo[4,3-a]pyrazin-7(8H)-yl)methanone | 529 | 0.32 |

Example 58

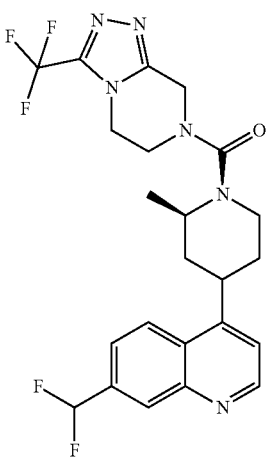

((3S,4S)-1-(7-(difluoromethyl)quinolin-4-yl)-3-methylpiperidin-4-yl)(3-(trifluoromethyl)-5,6-dihydro-[1,2,4]triazolo[4,3-a]pyrazin-7(8H)-yl)methanone Tributyl(vinyl)tin (0.905 ml, 3.10 mmol) was added to a solution of 7-bromo-4-fluoroquinoline (700 mg, 3.10 mmol) and Pd(Ph3P)4 (179 mg, 0.155 mmol) in 1,4-Dioxane (10 ml). The reaction mixture was heated for 20 min at 150° C. in a Biotage microwave reactor. The resulting mixture was concentrated and purified by silica gel chromatography (hexanes/EtOAc 100:0 to 70:30 gradient) to afford 4-fluoro-7-vinylquinoline. MS: 174 (M+1).

Water (0.50 ml), osmium tetroxide (2.5% in t-BuOH) (0.763 ml, 0.075 mmol), 2,6-dimethylpyridine (0.699 ml, 6.01 mmol), and sodium periodate (2569 mg, 12.01 mmol) was added sequentially to a solution of 4-fluoro-7-vinylquinoline (520 mg, 3.00 mmol) in 1,4-dioxane (2.5 ml) was sequentially added. The reaction mixture was stirred for 2 h at room temperature, quenched by adding H2O (20 mL), and extracted two times with DCM (2×20 mL). The combined organic layers were dried over MgSO4, concentrated, and purified by silica gel chromatography (hexanes/EtOAc 100:0 to 50:50 gradient) to afford 4-fluoroquinoline-7-carbaldehyde. MS: 176 (M+11).

DAST (0.302 ml, 2.284 mmol) was added to a solution of 4-fluoroquinoline-7-carbaldehyde (400 mg, 2.284 mmol) in CH2Cl2 (8 ml) at 0° C. The mixture was stirred at 0° C. for 20 min, then warmed to room temperature and stirred for 4 h and concentrated in vacuo. The residue was purified by column chromatography on silica gel, eluted with 0-30% ethyl acetate/hexane to give 7-(difluoromethyl)-4-fluoroquinoline. MS: 198 (M+11).

DIPEA (0.064 ml, 0.365 mmol) was added to a solution of 7-(difluoromethyl)-4-fluoroquinoline (18 mg, 0.091 mmol) and (3S,4S)-3-methyl-4-(3-(trifluoromethyl)-5,6,7,8-tetrahydro-[1,2,4]triazolo[4,3-a]pyrazine-7-carbonyl)piperidin-1-ium 2,2,2-trifluoroacetate (39.4 mg, 0.091 mmol) in DMF (2 ml). The reaction mixture was heated for 60 min at 140° C. in a Biotage microwave reactor. The resulting mixture was concentrated and purified by silica gel chromatography (hexanes/EtOAc 100:0 to 70:30 gradient) to afford ((3S,4S)-1-(7-(difluoromethyl)quinolin-4-yl)-3-methylpiperidin-4-yl)(3-(trifluoromethyl)-5,6-dihydro-[1,2,4]triazolo[4,3-a]pyrazin-7(8H)-yl)methanone. MS: 495 (M+1). Human CYP8B1 IC50 (nM) 5.97.

Example 59

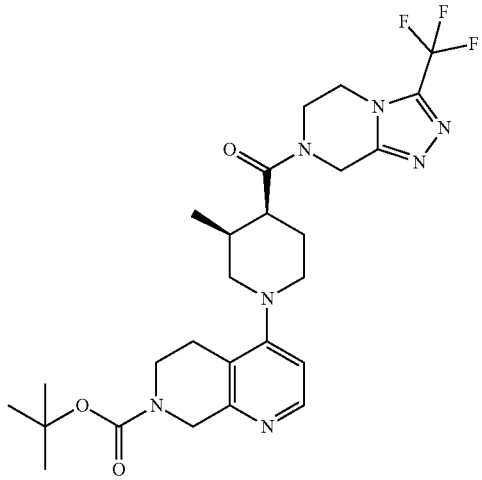 [SMILES: C[C@@H]1CN(c2ccnc3c2CCN(C(=O)OC(C)(C)C)C3)CC[C@@H]1C(=O)N1CCn2c(nnc2C(F)(F)F)C1]

tert-butyl 4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-5,6-dihydro-1,7-naphthyridine-7(8H)-carboxylate (BOC)₂O (0.948 ml, 4.08 mmol) was added to a solution of 4-bromo-5,6,7,8-tetrahydro-1,7-naphthyridine, HBr (1.0 g, 3.40 mmol) and Et₃N (1.185 ml, 8.50 mmol) in DCM (15 ml). The mixture was stirred at room temperature overnight and concentrated in vacuo. The residue was purified by column chromatography on silica gel, eluted with 0-3% MeOH/DCM to give as tert-butyl 4-bromo-5,6-dihydro-1,7-naphthyridine-7(8H)-carboxylate. MS: 313 and 315 (M+1).

2$^{nd}$ generation RuPhos precatalyst (16.93 mg, 0.022 mmol) was added to a solution of (3S,4S)-3-methyl-4-(3-(trifluoromethyl)-5,6,7,8-tetrahydro-[1,2,4]triazolo[4,3-a]pyrazine-7-carbonyl)piperidin-1-ium 2,2,2-trifluoroacetate (94 mg, 0.218 mmol), tert-butyl 4-bromo-5,6-dihydro-1,7-naphthyridine-7(8H)-carboxylate (68.3 mg, 0.218 mmol), DIPEA (0.038 ml, 0.218 mmol) and Cs₂Co₃ (284 mg, 0.872 mmol) in 1,4-Dioxane (2 ml). The mixture was heated to 80° C., stirred overnight and then concentrated in vacuo. The residue was purified by column chromatography on silica gel, eluted with 0-5% MeOH/DCM to give tert-butyl 4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-5,6-dihydro-1,7-naphthyridine-7(8H)-carboxylate. MS: 550 (M+11). Human CYP8B1 IC50 (nM) 8.20.

Example 60

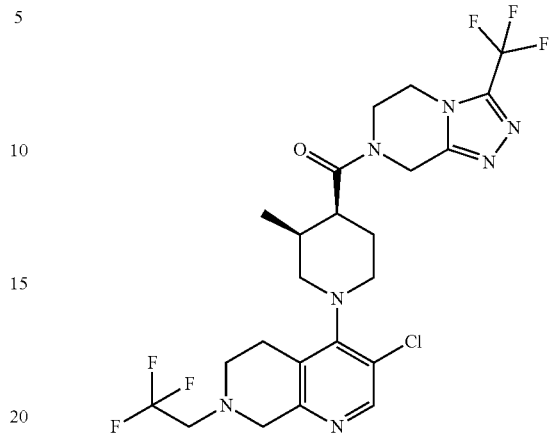

((3S,4S)-1-(3-chloro-7-(2,2,2-trifluoroethyl)-5,6,7,8-tetrahydro-1,7-naphthyridin-4-yl)-3-methylpiperidin-4-yl)(3-(trifluoromethyl)-5,6-dihydro-[1,2,4]triazolo[4,3-a]pyrazin-7(8H)-yl)methanone NCS (176 mg, 1.314 mmol) was added to a solution of tert-butyl 4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-5,6-dihydro-1,7-naphthyridine-7(8H)-carboxylate (516 mg, 0.939 mmol) in acetonitrile (3 ml) and DMF (5 ml). The mixture heated to 38° C., stirred for 20 h and cooled to room temperature. The mixture was then partitioned between ethyl acetate and H₂O, dried over Na2SO4, filtered and concentrated in vacuo. The residue was purified by column chromatography on silica gel, eluted with 0-4% MeOH/DCM to give tert-butyl 3-chloro-4-((3 S,4S)-3-methyl-4-(3-(trifluoromethyl)-5,6,7,8-tetrahydro-[1,2,4]triazolo[4,3-a]pyrazine-7-carbonyl)piperidin-1-yl)-5,6-dihydro-1,7-naphthyridine-7(8H)-carboxylate. MS: 584 (M+1).

TFA (1 ml, 12.98 mmol) was added to a solution of tert-butyl 3-chloro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-5,6-dihydro-1,7-naphthyridine-7(8H)-carboxylate (200 mg, 0.342 mmol) in CH₂Cl₂ (2 ml). The mixture was stirred at room temperature for 2 h and concentrated in vacuo to give ((3 S,4S)-1-(3-chloro-5,6,7,8-tetrahydro-1,7-naphthyridin-4-yl)-3-methylpiperidin-4-yl)(3-(trifluoromethyl)-5,6-dihydro-[1,2,4]triazolo[4,3-a]pyrazin-7(8H)-yl)methanone, TFA. MS: 484 (M+1).

2,2,2-trifluoroethyl trifluoromethanesulfonate (17.86 mg, 0.077 mmol) was added to a solution of ((3S,4S)-1-(3-chloro-5,6,7,8-tetrahydro-1,7-naphthyridin-4-yl)-3-methylpiperidin-4-yl)(3-(trifluoromethyl)-5,6-dihydro-[1,2,4]triazolo[4,3-a]pyrazin-7(8H)-yl)methanone, TFA (23 mg, 0.038 mmol) and Et₃N (0.021 ml, 0.154 mmol) in DCM (1.5 ml). The mixture was stirred at room temperature overnight and concentrated in vacuo. The residue was purified by preparative TLC, eluted with 4% MeOH/DCM, to give ((3S,4S)-1-(3-chloro-7-(2,2,2-trifluoroethyl)-5,6,7,8-tetrahydro-1,7-naphthyridin-4-yl)-3-methylpiperidin-4-yl)(3-(trifluoromethyl)-5,6-dihydro-[1,2,4]triazolo[4,3-a]pyrazin-7(8H)-yl)methanone. MS: 566 (M+1). Human CYP8B1 IC50 (nM) 0.8.

Example 61

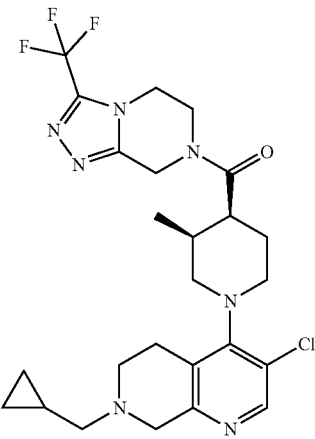 [SMILES: C[C@@H]1CN(c2c(Cl)cnc3c2CCN(CC2CC2)C3)CC[C@@H]1C(=O)N1CCn2c(nnc2C(F)(F)F)C1]

((3S,4S)-1-(3-chloro-7-(cyclopropylmethyl)-5,6,7,8-tetrahydro-1,7-naphthyridin-4-yl)-3-methylpiperidin-4-yl)(3-(trifluoromethyl)-5,6-dihydro-[1,2,4]triazolo[4,3-a]pyrazin-7(8H)-yl)methanone A microwave tube was charged with (bromomethyl)cyclopropane (13.95 mg, 0.103 mmol), ((3S,4S)-1-(3-chloro-5,6,7,8-tetrahydro-1,7-naphthyridin-4-yl)-3-methylpiperidin-4-yl)(3-(trifluoromethyl)-5,6-dihydro-[1,2,4]triazolo[4,3-a]pyrazin-7(8H)-yl)methanone (25 mg, 0.052 mmol), DIPEA (0.036 ml, 0.207 mmol) and DCM (1.5 ml). The mixture was heated to 50° C. and stirred overnight and concentrated in vacuo. The residue was purified by preparative TLC, eluted with 4% MeOH/DCM, to give ((3S,4S)-1-(3-chloro-7-(cyclopropylmethyl)-5,6,7,8-tetrahydro-1,7-naphthyridin-4-yl)-3-methylpiperidin-4-yl)(3-(trifluoromethyl)-5,6-dihydro-[1,2,4]triazolo[4,3-a]pyrazin-7(8H)-yl)methanone. MS: 539 (M+1). Human CYP8B1 IC50 (nM) 1.0.

Example 62

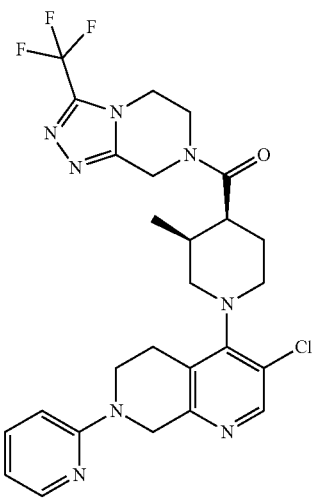 [SMILES: C[C@@H]1CN(c2c(Cl)cnc3c2CCN(c2ccccn2)C3)CC[C@@H]1C(=O)N1CCn2c(nnc2C(F)(F)F)C1]

((3S,4S)-1-(3-chloro-7-(pyridin-2-yl)-5,6,7,8-tetrahydro-1,7-naphthyridin-4-yl)-3-methylpiperidin-4-yl)(3-(trifluoromethyl)-5,6-dihydro-[1,2,4]triazolo[4,3-a]pyrazin-7(8H)-yl)methanone $Cs_2CO_3$ (65.4 mg, 0.201 mmol) and $2^{nd}$ generation RuPhos precatalyst (5.85 mg, 7.53 mol) was added to a solution of ((3S,4S)-1-(3-chloro-5,6,7,8-tetrahydro-1,7-naphthyridin-4-yl)-3-methylpiperidin-4-yl)(3-(trifluoromethyl)-5,6-dihydro-[1,2,4]triazolo[4,3-a]pyrazin-7(8H)-yl)methanone, TFA (30 mg, 0.050 mmol) and 2-bromopyridine (15.85 mg, 0.100 mmol) in 1,4-dioxane (1.5 ml). The mixture was heated to 85° C., stirred for 4 h and concentrated in vacuo. The residue was purified by column chromatography on silica gel, eluted with 0-4% MeOH/DCM to give ((3S,4S)-1-(3-chloro-7-(pyridin-2-yl)-5,6,7,8-tetrahydro-1,7-naphthyridin-4-yl)-3-methylpiperidin-4-yl)(3-(trifluoromethyl)-5,6-dihydro-[1,2,4]triazolo[4,3-a]pyrazin-7(8H)-yl)methanone. MS: 562 (M+1). Human CYP8B1 IC50 (nM) 0.4.

Example 63

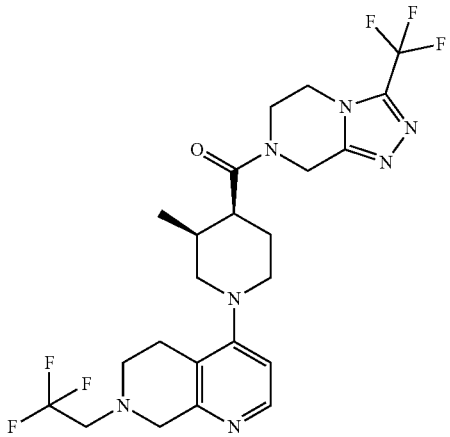 [SMILES: C[C@@H]1CN(c2ccnc3c2CCN(CC(F)(F)F)C3)CC[C@@H]1C(=O)N1CCn2c(nnc2C(F)(F)F)C1]

((3S,4S)-3-methyl-1-(7-(2,2,2-trifluoroethyl)-5,6,7,8-tetrahydro-1,7-naphthyridin-4-yl)piperidin-4-yl)(3-(trifluoromethyl)-5,6-dihydro-[1,2,4]triazolo[4,3-a]pyrazin-7(8H)-yl)methanone TFA (1.0 ml, 12.98 mmol) was added to a solution of tert-butyl 4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-5,6-dihydro-1,7-naphthyridine-7(8H)-carboxylate (30 mg, 0.055 mmol) in $CH_2Cl_2$ (1 ml). The mixture was stirred at room temperature for 5 h and concentrated in vacuo. The residue was redissolved in $CH_2Cl_2$ (1 ml), followed by addition of DIPEA (0.048 ml, 0.273 mmol) and 2,2,2-trifluoroethyl trifluoromethanesulfonate (25.3 mg, 0.109 mmol). The mixture was stirred at room temperature overnight and concentrated in vacuo. The residue was purified by column chromatography on silica gel, eluted with 0-5% MeOH/DCM to give ((3S,4S)-3-methyl-1-(7-(2,2,2-trifluoroethyl)-5,6,7,8-tetrahydro-1,7-naphthyridin-4-yl)piperidin-4-yl)(3-(trifluoromethyl)-5,6-dihydro-[1,2,4]triazolo[4,3-a]pyrazin-7(8H)-yl)methanone. MS: 532 (M+1). Human CYP8B1 IC50 (nM) 120.

Example 64

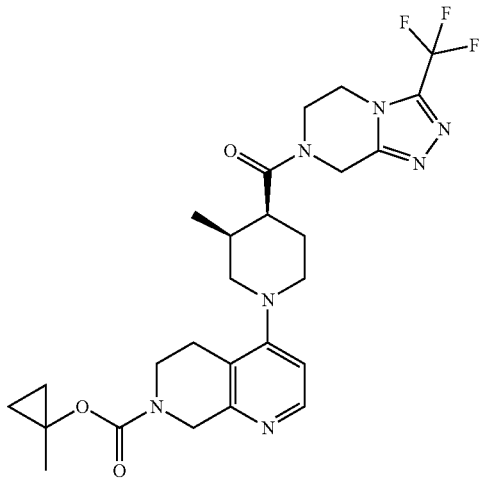 [SMILES: C[C@@H]1CN(c2ccnc3c2CCN(C(=O)OC2(C)CC2)C3)CC[C@@H]1C(=O)N1CCn2c(nnc2C(F)(F)F)C1]

1-methylcyclopropyl 4-((3 S,4S)-3-methyl-4-(3-(trifluoromethyl)-5,6,7,8-tetrahydro-[1,2,4]triazolo[4,3-a]pyrazine-7-carbonyl)piperidin-1-yl)-5,6-dihydro-1,7-naphthyridine-7(8H)-carboxylate HCl (4.0M in dioxane) (1.5 ml, 6.00 mmol) was added to a solution of tert-butyl 4-((3 S,4S)-3-methyl-4-(3-(trifluoromethyl)-5,6,7,8-tetrahydro-[1,2,4]triazolo[4,3-a]pyrazine-7-carbonyl)piperidin-1-yl)-5,6-dihydro-1,7-naphthyridine-7(8H)-carboxylate (90 mg, 0.164 mmol) in DCM (2 ml) and MeOH (1 ml). The mixture was stirred at room temperature for 4 h and concentrated in vacuo. The residue was redissolved in THF (2.000 ml) and DIPEA (0.114 ml, 0.655 mmol), followed by addition of 2,5-dioxopyrrolidin-1-yl (1-methylcyclopropyl) carbonate (52.4 mg, 0.246 mmol). The mixture was stirred at room temperature for 1 h and concentrated in vacuo. The residue was purified by preparative TLC, eluting with 5% MeOH/DCM, to give 1-methylcyclopropyl 4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-5,6-dihydro-1,7-naphthyridine-7(8H)-carboxylate. MS: 548 (M+1). Human CYP8B1 IC50 (nM) 49.

Example 65

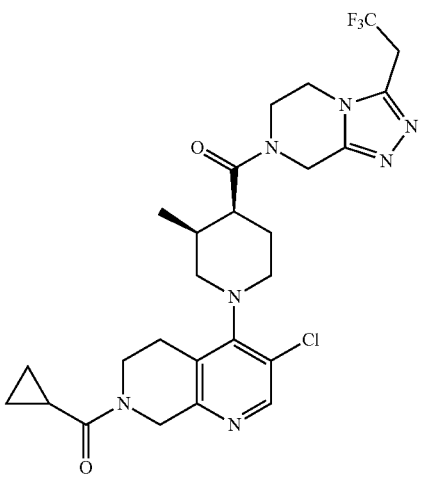 [SMILES: C[C@@H]1CN(c2c(Cl)cnc3c2CCN(C(=O)C2CC2)C3)CC[C@@H]1C(=O)N1CCn2c(nnc2CC(F)(F)F)C1]

(3-chloro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-5,6-dihydro-1,7-naphthyridin-7(8H)-yl)(cyclopropyl)methanone Cyclopropanecarbonyl chloride (43.0 mg, 0.412 mmol) was added to a solution of 4-bromo-5,6,7,8-tetrahydro-1,7-naphthyridine, HBr (110 mg, 0.374 mmol) and Et$_3$N (0.209 ml, 1.497 mmol) in THF (3 ml). The mixture was stirred at room temperature for 3 h and concentrated in vacuo. The residue was purified by column chromatography on silica gel, eluting with 0-2% MeOH/DCM to give (4-bromo-5,6-dihydro-1,7-naphthyridin-7(8H)-yl)(cyclopropyl)methanone. MS: 282 (M+1).

(3S,4S)-tert-butyl 3-methylpiperidine-4-carboxylate (77 mg, 0.384 mmol), Cs$_2$CO$_3$ (313 mg, 0.960 mmol) and 2$^{nd}$ generation RuPhos Precatalyst (24.86 mg, 0.032 mmol) were added to a solution of (4-bromo-5,6-dihydro-1,7-naphthyridin-7(8H)-yl)(cyclopropyl) methanone (90 mg, 0.320 mmol) in 1,4-Dioxane (2 ml). The mixture was heated to 95° C. and stirred overnight. Filtration removed the solid. After washing with ethyl acetate, the combined filtrate was concentrated in vacuo. The residue was purified by preparative TLC, eluting with 4% MeOH/DCM, to give (3S,4S)-tert-butyl 1-(7-(cyclopropanecarbonyl)-5,6,7,8-tetrahydro-1,7-naphthyridin-4-yl)-3-methylpiperidine-4-carboxylate. MS: 400 (M+11).

NCS (37.6 mg, 0.282 mmol) was added to a solution of (3S,4S)-tert-butyl 1-(7-(cyclopropanecarbonyl)-5,6,7,8-tetrahydro-1,7-naphthyridin-4-yl)-3-methylpiperidine-4-carboxylate (75 mg, 0.188 mmol) in acetonitrile (2 ml). The mixture was heated to 35° C., stirred overnight and then concentrated in vacuo. The residue was purified by column chromatography on silica gel, eluting with 0-2% MeOH/DCM to give (3S,4S)-tert-butyl 1-(3-chloro-7-(cyclopropanecarbonyl)-5,6,7,8-tetrahydro-1,7-naphthyridin-4-yl)-3-methylpiperidine-4-carboxylate. MS: 434 (M+11).

TFA (1.0 ml, 12.98 mmol) was added to a solution of (3S,4S)-tert-butyl 1-(3-chloro-7-(cyclopropanecarbonyl)-5,6,7,8-tetrahydro-1,7-naphthyridin-4-yl)-3-methylpiperidine-4-carboxylate (82 mg, 0.189 mmol) in CH$_2$Cl$_2$ (1 ml). The mixture was stirred at room temperature for 3 h and concentrated in vacuo to give (3S,4S)-1-(3-chloro-7-(cyclopropanecarbonyl)-5,6,7,8-tetrahydro-1,7-naphthyridin-4-yl)-3-methylpiperidine-4-carboxylic acid, TFA. MS: 378 (M+11).

3-(trifluoromethyl)-5,6,7,8-tetrahydro-[1,2,4]triazolo[4,3-a]pyrazine, HCl (17.43 mg, 0.076 mmol) and HATU (29.0 mg, 0.076 mmol) was added to a solution of (3S,4S)-1-(3-chloro-7-(cyclopropanecarbonyl)-5,6,7,8-tetrahydro-1,7-naphthyridin-4-yl)-3-methylpiperidine-4-carboxylic acid, TFA (25 mg, 0.051 mmol) and DIPEA (0.027 ml, 0.152 mmol) in THF (1 ml) was added. The mixture was heated to 50° C. and stirred for 2 h. The reaction was concentrated in vacuo. The residue was purified by column chromatography on silica gel, eluting with 0-3% MeOH/DCM to give (3-chloro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-5,6-dihydro-1,7-naphthyridin-7(8H)-yl)(cyclopropyl)methanone (12 mg, 0.022 mmol, 42.8% yield) MS: 552 (M+11). Human CYP8B1 IC50 (nM) 1.75.

Example 66

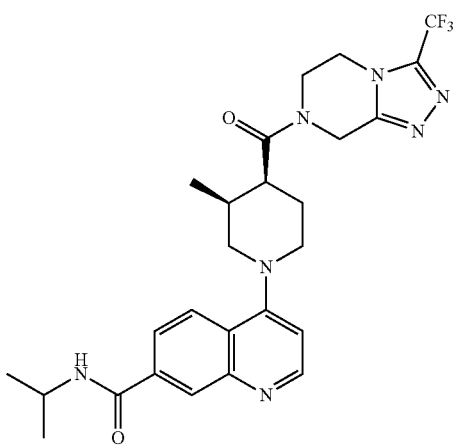 [SMILES: CC(C)NC(=O)c1ccc2c(N3CC[C@H](C(=O)N4CCn5c(nnc5C(F)(F)F)C4)[C@H](C)C3)ccnc2c1]

N-isopropyl-4-((3 S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-7-carboxamide Propan-2-amine (128 mg, 2.167 mmol), HATU (824 mg, 2.167 mmol) and DIPEA (0.505 ml, 2.89 mmol) were added to a solution of 4-chloroquinoline-7-carboxylic acid (300 mg, 1.445 mmol) in THF (10 ml). The mixture was heated to 50° C., stirred for 2 h and concentrated in vacuo. The residue was purified by column chromatography on silica gel, eluting with 0-5% MeOH/DCM to give 4-chloro-N-isopropylquinoline-7-carboxamide. MS: 249 (M+1).

DIPEA (0.112 ml, 0.643 mmol) was added to a solution of 4-chloro-N-isopropylquinoline-7-carboxamide (40 mg, 0.161 mmol) and ((3S,4S)-3-methylpiperidin-4-yl)(3-(trifluoromethyl)-5,6-dihydro-[1,2,4]triazolo[4,3-a]pyrazin-7(8H)-yl)methanone, HCl (56.9 mg, 0.161 mmol) in DMF (2 ml). The reaction mixture was heated for 60 min at 140° C. in a Biotage microwave reactor. The resulting mixture was concentrated and purified by silica gel chromatography (hexanes/EtOAc 100:0 to 70:30 gradient) to afford Example 66, which was dissolved in MeOH (2 ml). 1 ml 1N HCl in diethyl ether was added to the solution. The mixture was stirred for 20 min, concentrated in vacuo to give the HCl salt N-isopropyl-4-((3 S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-7-carboxamide, HCl. MS: 530 (M+1). Human CYP8B1 IC50 (nM) 4.5.

Example 67

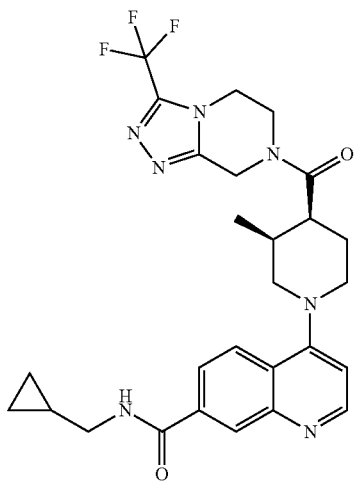 [SMILES: C[C@@H]1CN(c2ccnc3cc(C(=O)NCC4CC4)ccc23)CC[C@@H]1C(=O)N1CCn2c(nnc2C(F)(F)F)C1]

N-(cyclopropylmethyl)-4-((3 S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-7-carboxamide A microwave tube was charged with ((3S,4S)-3-methylpiperidin-4-yl)(3-(trifluoromethyl)-5,6-dihydro-[1,2,4]triazolo[4,3-a]pyrazin-7(8H)-yl)methanone, HCl (180 mg, 0.509 mmol), 4-bromoquinoline-7-carboxylic acid (154 mg, 0.611 mmol), DIPEA (0.267 ml, 1.526 mmol) and DMF (3 ml). The mixture was microwaved at 185° C. for 1 h and concentrated in vacuo to give 4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-7-carboxylic acid. MS: 489 (M+1).

Cyclopropylmethanamine, HCl (17.62 mg, 0.164 mmol) and HATU (62.3 mg, 0.164 mmol) were added to a solution of 4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-7-carboxylic acid (40 mg, 0.082 mmol)) and DIPEA (0.057 ml, 0.328 mmol) in tetrahydrofuran (2 ml). The mixture was heated to 50° C., stirred for 3 h and concentrated in vacuo. The residue was purified by column chromatography on silica gel, eluted with 0-3% MeOH/DCM to give N-(cyclopropylmethyl)-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-7-carboxamide. MS: 542 (M+1). Human CYP8B1 IC50 (nM) 23.6.

Examples 68-69 were made using a similar synthesis to Example 67 substituting the appropriate reactants and reagents.

| Example | Structure | IUPAC Name | Exact Mass [M + H]+ | Human CYP8B1 IC50 (nM) |
|---|---|---|---|---|
| 68 | 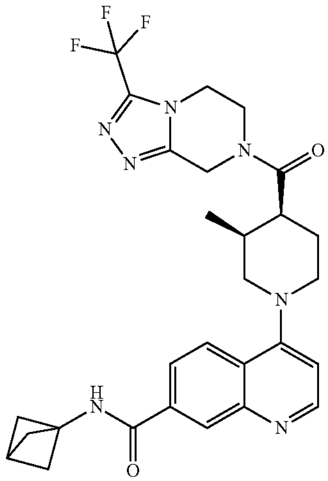 [SMILES: C[C@@H]1CN(c2ccnc3cc(C(=O)NC45CC(C4)C5)ccc23)CC[C@@H]1C(=O)N1CCn2c(nnc2C(F)(F)F)C1] | N-(bicyclo[1.1.1]pentan-1-yl)-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-7-carboxamide | 542 | 21.1 |
| 69 | 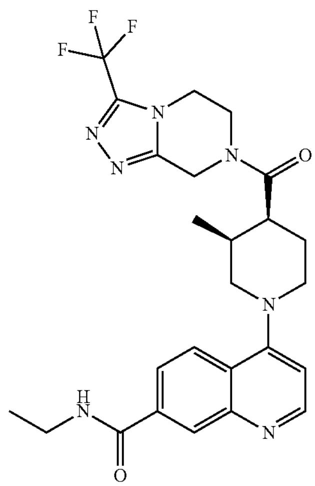 [SMILES: CCNC(=O)c1ccc2c(N3CC[C@H](C(=O)N4CCn5c(nnc5C(F)(F)F)C4)[C@H](C)C3)ccnc2c1] | N-ethyl-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-7-carboxamide | 516 | 368 |

Example 70

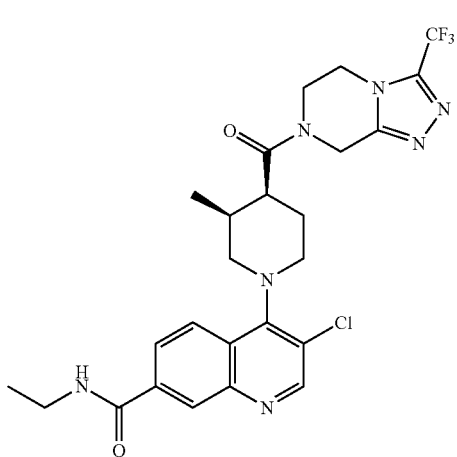 [SMILES: CCNC(=O)c1ccc2c(N3CC[C@H](C(=O)N4CCn5c(nnc5C(F)(F)F)C4)[C@H](C)C3)c(Cl)cnc2c1]

3-chloro-N-ethyl-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-7-carboxamide NCS (15.54 mg, 0.116 mmol) was added to a solution of N-ethyl-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-7-carboxamide (30 mg, 0.058 mmol) in acetonitrile (1 ml). The mixture was heated to 35° C., stirred overnight and concentrated in vacuo. The residue was purified by preparative TLC, eluted with 4% MeOH/DCM, to give 3-chloro-N-ethyl-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-7-carboxamide. MS: 550 (M+1). Human CYP8B1 IC50 (nM) 0.7.

Example 71

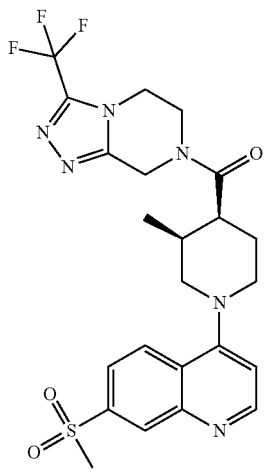 [SMILES: C[C@@H]1CN(c2ccnc3cc(S(C)(=O)=O)ccc23)CC[C@@H]1C(=O)N1CCn2c(nnc2C(F)(F)F)C1]

((3 S,4S)-3-methyl-1-(7-(methylsulfonyl)quinolin-4-yl)piperidin-4-yl)(3-(trifluoromethyl)-5,6-dihydro-[1,2,4]triazolo[4,3-a]pyrazin-7(8H)-yl)methanone A microwave tube was charged with 7-bromo-4-fluoroquinoline (330 mg, 1.460 mmol), ((3 S,4S)-3-methylpiperidin-4-yl)(3-(trifluoromethyl)-5,6-dihydro-[1,2,4]triazolo[4,3-a]pyrazin-7(8H)-yl)methanone, HCl (516 mg, 1.460 mmol), $K_2CO_3$ (605 mg, 4.38 mmol) and DMF (5 ml). The mixture was microwaved at 160° C. for 1 h, partitioned between ethyl acetate and $H_2O$, dried over $Na_2SO_4$, filtered and concentrated in vacuo. The residue was purified by column chromatography on silica gel, eluted with 0-4% MeOH/DCM to give ((3S,4S)-1-(7-bromoquinolin-4-yl)-3-methylpiperidin-4-yl)(3-(trifluoromethyl)-5,6-dihydro-[1,2,4]triazolo[4,3-a]pyrazin-7(8H)-yl)methanone. MS: 522 and 524 (M+1).

Copper(I) iodide (14.56 mg, 0.076 mmol) and sodium methanesulfinate (31.2 mg, 0.306 mmol) were added to a solution of ((3S,4S)-1-(7-bromoquinolin-4-yl)-3-methylpiperidin-4-yl)(3-(trifluoromethyl)-5,6-dihydro-[1,2,4]triazolo[4,3-a]pyrazin-7(8H)-yl)methanone (80 mg, 0.153 mmol) and L-proline (8.80 mg, 0.076 mmol) in DMSO (1.5 ml). The reaction mixture was heated at 100° C. in a Biotage microwave reactor, stirred overnight and filtered through a pad of the CELITE to remove the solid. After washing with ethyl acetate, the combined filtrate was concentrated in vacuo. The residue was purified by column chromatography on silica gel, eluting with 0-3% MeOH/DCM to give ((3S,4S)-3-methyl-1-(7-(methylsulfonyl)quinolin-4-yl)piperidin-4-yl)(3-(trifluoromethyl)-5,6-dihydro-[1,2,4]triazolo[4,3-a]pyrazin-7(8H)-yl)methanone. MS: 522 (M+11). Human CYP8B1 IC50 (nM) 305.

Example 72

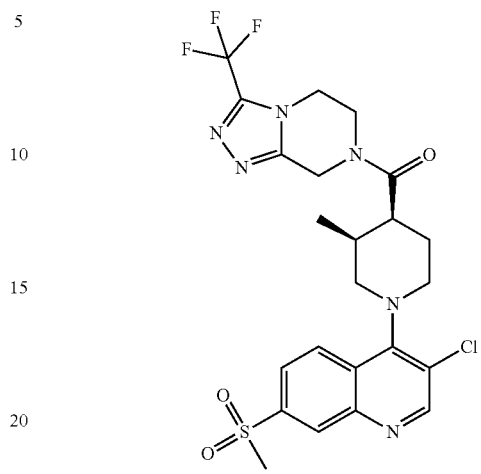

((3S,4S)-1-(3-chloro-7-(methylsulfonyl)quinolin-4-yl)-3-methylpiperidin-4-yl)(3-(trifluoromethyl)-5,6-dihydro-[1,2,4]triazolo[4,3-a]pyrazin-7(8H)-yl)methanone NCS (20.44 mg, 0.153 mmol) was added to a solution of ((3S,4S)-3-methyl-1-(7-(methylsulfonyl)quinolin-4-yl)piperidin-4-yl)(3-(trifluoromethyl)-5,6-dihydro-[1,2,4]triazolo[4,3-a]pyrazin-7(8H)-yl)methanone (40 mg, 0.077 mmol) in acetonitrile (1.5 ml). The mixture was heated to 35° C., stirred overnight and concentrated in vacuo. The residue was purified by preparative TLC, eluted with 4% MEOH/DCM, to give ((3S,4S)-1-(3-chloro-7-(methylsulfonyl)quinolin-4-yl)-3-methylpiperidin-4-yl)(3-(trifluoromethyl)-5,6-dihydro-[1,2,4]triazolo[4,3-a]pyrazin-7(8H)-yl)methanone. MS: 557 (M+1). Human CYP8B1 IC50 (nM) 1.2.

Example 73

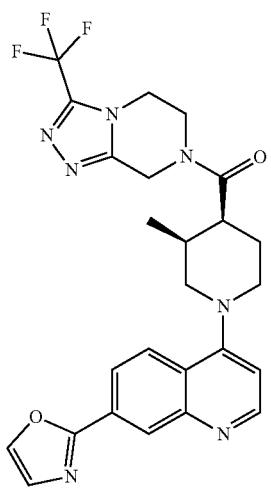 [SMILES: C[C@@H]1CN(c2ccnc3cc(-c4ncco4)ccc23)CC[C@@H]1C(=O)N1CCn2c(nnc2C(F)(F)F)C1]

((3S,4S)-3-methyl-1-(7-(oxazol-2-yl)quinolin-4-yl)
piperidin-4-yl)(3-(trifluoromethyl)-5,6-dihydro-[1,2,
4]triazolo[4,3-a]pyrazin-7(8H)-yl)methanone A microwave tube was charged with ((3S,4S)-1-(7-bromoquinolin-4-yl)-3-methylpiperidin-4-yl)(3-(trifluoromethyl)-5,6-dihydro-[1,2,4]triazolo[4,3-a]pyrazin-7(8H)-yl)methanone (30 mg, 0.057 mmol), 2-(tributylstannyl)oxazole (0.018 ml, 0.086 mmol), Pd(Ph₃P)₄ (13.25 mg, 0.011 mmol) and 1,4-dioxane (2 ml). The mixture was microwaved at 150° C. for 25 min and then filtered through a pad of CELITE to remove the solids. The solids were washed with ethyl acetate and the combined filtrate was concentrated in vacuo. The residue was purified by column chromatography on silica gel, eluted with 0-4% MeOH/DCM to give ((3S,4S)-3-methyl-1-(7-(oxazol-2-yl)quinolin-4-yl)piperidin-4-yl)(3-(trifluoromethyl)-5,6-dihydro-[1,2,4]triazolo[4,3-a]pyrazin-7(8H)-yl)methanone. MS: 512 (M+1). Human CYP8B1 IC50 (nM) 0.4.

Example 74

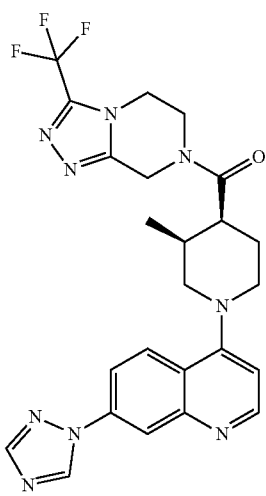 [SMILES: C[C@@H]1CN(c2ccnc3cc(-n4cncn4)ccc23)CC[C@@H]1C(=O)N1CCn2c(nnc2C(F)(F)F)C1]

((3S,4S)-1-(7-(1H-1,2,4-triazol-1-yl)quinolin-4-yl)-
3-methylpiperidin-4-yl)(3-(trifluoromethyl)-5,6-
dihydro-[1,2,4]triazolo[4,3-a]pyrazin-7(8H)-yl)
methanone Trans-N,N'dimethylcyclohexane-1,2-diamine (0.013 ml, 0.011 mmol), Cs₂CO₃ (37.4 mg, 0.115 mmol) and cuprous iodide (5.46 mg, 0.029 mmol) were added to a solution of ((3S,4S)-1-(7-bromoquinolin-4-yl)-3-methylpiperidin-4-yl)(3-(trifluoromethyl)-5,6-dihydro-[1,2,4]triazolo[4,3-a]pyrazin-7(8H)-yl)methanone (30 mg, 0.057 mmol) and 1H-1,2,4-triazole (11.88 mg, 0.172 mmol) in DMF (1 ml). The mixture was heated to 120° C., stirred overnight and filtered through a CELITE pad to remove the solids. After washing with ethyl acetate, the combined filtrate was concentrated in vacuo. The residue was purified by column chromatography on silica gel, eluted with 0-4% MeOH to give ((3S,4S)-1-(7-(1H-1,2,4-triazol-1-yl)quinolin-4-yl)-3-methylpiperidin-4-yl)(3-(trifluoromethyl)-5,6-dihydro-[1,2,4]triazolo[4,3-a]pyrazin-7(8H)-yl)methanone. MS: 512 (M+1). Human CYP8B1 IC50 (nM) 41.7.

Example 75

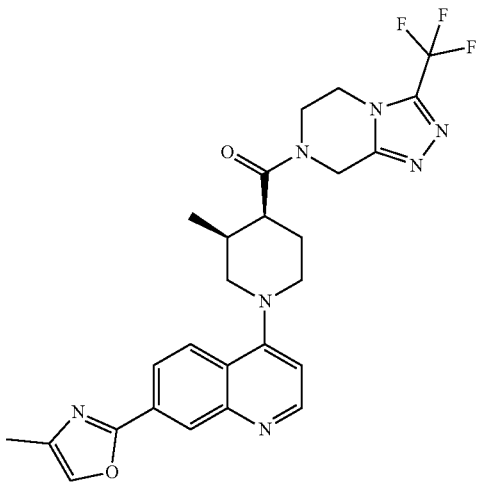 [SMILES: Cc1coc(-c2ccc3c(N4CC[C@H](C(=O)N5CCn6c(nnc6C(F)(F)F)C5)[C@H](C)C4)ccnc3c2)n1]

((3S,4S)-3-methyl-1-(7-(4-methyloxazol-2-yl)quino-
lin-4-yl)piperidin-4-yl)(3-(trifluoromethyl)-5,6-di-
hydro-[1,2,4]triazolo[4,3-a]pyrazin-7(8H)-yl)metha-
none Tetrahydroxydiboron (44.5 mg, 0.497 mmol) and PCy₃ precatalyst (14.67 mg, 0.025 mmol) were added to a solution of ((3 S,4S)-1-(7-bromoquinolin-4-yl)-3-methylpiperidin-4-yl)(3-(trifluoromethyl)-5,6-dihydro-[1,2,4]triazolo[4,3-a]pyrazin-7(8H)-yl)methanone (130 mg, 0.248 mmol) and DIPEA (0.087 ml, 0.497 mmol) in MeOH (2 ml). The mixture was stirred at 35° C. for 5 h and concentrated to give (4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinolin-7-yl)boronic acid. MS: 490 (M+1).

A microwave tube was charged with (4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinolin-7-yl)boronic acid (30 mg, 0.061 mmol)), 2-bromo-4-methyloxazole, HCl (18.29 mg, 0.092 mmol), TBPFPdCl₂ (6.01 mg, 9.22 μmol), Cs₂CO₃ (60.1 mg, 0.184 mmol) and 1,4-dioxane (1 ml) and water (100 μL). The mixture was heated to 80° C., stirred overnight and concentrated in vacuo. The residue was purified by column chromatography on silica gel, eluted with 0-3% MeOH/DCM to give ((3S,4S)-3-methyl-1-(7-(4-methyloxazol-2-yl)quinolin-4-yl)piperidin-4-yl)(3-(trifluoromethyl)-5,6-dihydro-[1,2,4]triazolo[4,3-a]pyrazin-7(8H)-yl)methanone. MS: 526 (M+1). Human CYP8B1 IC50 (nM) 1.4.

Example 76

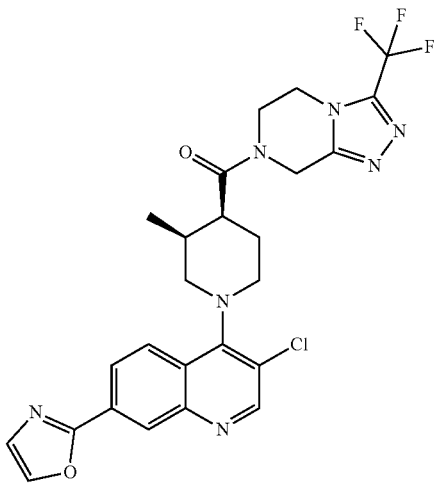 [SMILES: C[C@@H]1CN(c2c(Cl)cnc3cc(-c4ncco4)ccc23)CC[C@@H]1C(=O)N1CCn2c(nnc2C(F)(F)F)C1]

((3S,4S)-1-(3-chloro-7-(oxazol-2-yl)quinolin-4-yl)-
3-methylpiperidin-4-yl)(3-(trifluoromethyl)-5,6-
dihydro-[1,2,4]triazolo[4,3-a]pyrazin-7(8H)-yl)
methanone NCS (109 mg, 0.814 mmol) was added to a solution of (3S,4S)-tert-butyl 1-(7-bromoquinolin-4-yl)-3-methylpiperidine-4-carboxylate (220 mg, 0.543 mmol) in acetonitrile (3 ml) was added. The mixture was heated to 35° C., stirred overnight and concentrated in vacuo. The residue was purified by preparative TLC, eluted with 0-2% MeOH/DCM, to give (3S,4S)-tert-butyl 1-(7-bromo-3-chloroquinolin-4-yl)-3-methylpiperidine-4-carboxylate. MS: 440 (M+1).

A microwave tube was charged with (3S,4S)-tert-butyl 1-(7-bromo-3-chloroquinolin-4-yl)-3-methylpiperidine-4-carboxylate (180 mg, 0.409 mmol), 2-(tributylstannyl)oxazole (0.120 ml, 0.573 mmol), Pd(Ph₃P)₄ (47.3 mg, 0.041 mmol) and 1,4-Dioxane (5 ml). The mixture was microwaved at 150° C. for 25 min. and filtered through a CELITE pad to remove the solids. After washing with ethyl acetate, the combined filtrate was concentrated in vacuo. The residue was purified by column chromatography on silica gel, eluted with 0-4% MeOH/DCM to give (3S,4S)-tert-butyl 1-(3-chloro-7-(oxazol-2-yl)quinolin-4-yl)-3-methylpiperidine-4-carboxylate. MS: 428 (M+1)

TFA (1 ml, 12.98 mmol) was added to a solution of (3S,4S)-tert-butyl 1-(3-chloro-7-(oxazol-2-yl)quinolin-4-yl)-3-methylpiperidine-4-carboxylate (110 mg, 0.257 mmol) in CH₂Cl₂ (1 ml). The mixture was stirred at room temperature for 2 h and concentrated in vacuo to give (3S,4S)-1-(3-chloro-7-(oxazol-2-yl)quinolin-4-yl)-3-methylpiperidine-4-carboxylic acid, TFA. MS: 372 (M+1).

(3S,4S)-1-(3-chloro-7-(oxazol-2-yl)quinolin-4-yl)-3-methylpiperidine-4-carboxylic acid, TFA (30 mg, 0.062 mmol) and HATU (35.2 mg, 0.093 mmol) were added to a solution of 3-(trifluoromethyl)-5,6,7,8-tetrahydro-[1,2,4]triazolo[4,3-a]pyrazine, HCl (21.17 mg, 0.093 mmol) and DIPEA (0.054 ml, 0.309 mmol) in tetrahydrofuran (3 ml). The mixture was heated to 50° C., stirred for 2 h and concentrated in vacuo. The residue was purified by column chromatography on silica gel, eluted with 0-$% MeOH/DCM to give ((3S,4S)-1-(3-chloro-7-(oxazol-2-yl)quinolin-4-yl)-3-methylpiperidin-4-yl)(3-(trifluoromethyl)-5,6-dihydro-[1,2,4]triazolo[4,3-a]pyrazin-7(8H)-yl)methanone. MS: 546 (M+1). Human CYP8B1 IC50 (nM) 0.7.

Example 77-78 was made using a similar synthesis to Example 76 substituting the appropriate reactants and reagents.

| Example | Structure | IUPAC Name | Exact Mass [M + H]+ | Human CYP8B1 IC50 (nM) |
|---|---|---|---|---|
| 77 | 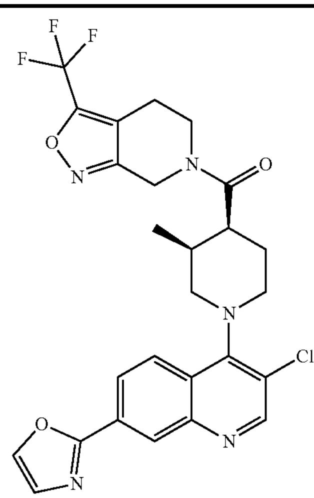 | ((3S,4S)-1-(3-chloro-7-(oxazol-2-yl)quinolin-4-yl)-3-methylpiperidin-4-yl)(3-(trifluoromethyl)-4,5-dihydroisoxazolo[3,4-c]pyridin-6(7H)-yl)methanone | 546 | 0.2 |

| Example | Structure | IUPAC Name | Exact Mass [M + H]+ | Human CYP8B1 IC50 (nM) |
|---|---|---|---|---|
| 78 | 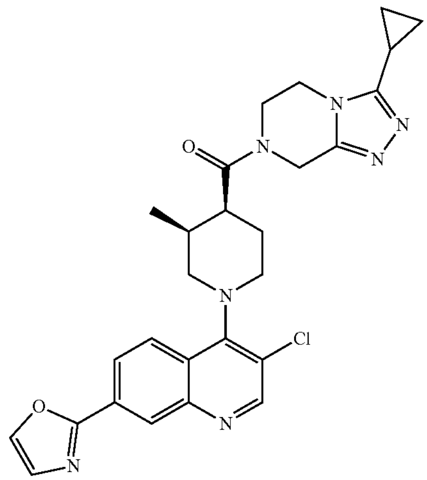 [SMILES: C[C@@H]1CN(c2c(Cl)cnc3cc(-c4ncco4)ccc23)CC[C@@H]1C(=O)N1CCn2c(nnc2C2CC2)C1] | ((3S,4S)-1-(3-chloro-7-(oxazol-2-yl)quinolin-4-yl)-3-methylpiperidin-4-yl)(3-cyclopropyl-5,6-dihydro-[1,2,4]triazolo[4,3-a]pyrazin-7(8H)-yl)methanone | 519 | 0.5 |

Example 79

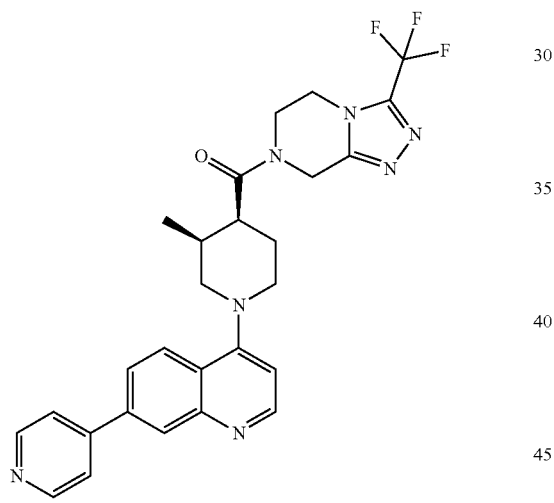

((3S,4S)-3-methyl-1-(7-(pyridin-4-yl)quinolin-4-yl)piperidin-4-yl)(3-(trifluoromethyl)-5,6-dihydro-[1,2,4]triazolo[4,3-a]pyrazin-7(8H)-yl)methanone A microwave tube was charged with ((3 S,4S)-1-(7-bromoquinolin-4-yl)-3-methylpiperidin-4-yl)(3-(trifluoromethyl)-5,6-dihydro-[1,2,4]triazolo[4,3-a]pyrazin-7(8H)-yl)methanone (30 mg, 0.057 mmol), pyridin-4-ylboronic acid (12.68 mg, 0.103 mmol), TBPFPdCl$_2$ (7.47 mg, 0.011 mmol), Cs$_2$CO$_3$ (56.0 mg, 0.172 mmol) and 1,4-dioxane (1 ml) and water (100 µL). The mixture was heated to 80° C., stirred overnight and concentrated in vacuo. The residue was purified by column chromatography on silica gel, eluted with 0-3% MeOH/DCM to give ((3S,4S)-3-methyl-1-(7-(pyridin-4-yl)quinolin-4-yl)piperidin-4-yl)(3-(trifluoromethyl)-5,6-dihydro-[1,2,4]triazolo[4,3-a]pyrazin-7(8H)-yl)methanone. MS: 522 (M+1). Human CYP8B1 IC50 (nM) 0.7.

Example 80 was made using a similar synthesis to Example 79 substituting the appropriate reactants and reagents.

| Example | Structure | IUPAC Name | Exact Mass [M + H]+ | Human CYP8B1 IC50 (nM) |
|---|---|---|---|---|
| 80 | 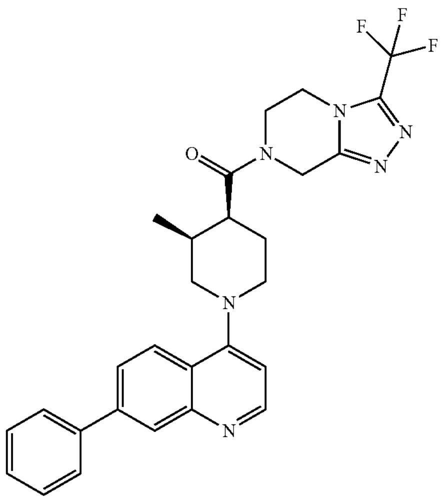 [SMILES: C[C@@H]1CN(c2ccnc3cc(-c4ccccc4)ccc23)CC[C@@H]1C(=O)N1CCn2c(nnc2C(F)(F)F)C1] | ((3S,4S)-3-methyl-1-(7-phenylquinolin-4-yl)piperidin-4-yl)(3-(trifluoromethyl)-5,6-dihydro-[1,2,4]triazolo[4,3-a]pyrazin-7(8H)-yl)methanoneyl)methanone | 521 | 0.4 |

Human Cyp8B1 Liver Microsome Assay To a 384 well polypropylene plate (Corning 3656), 250 nl of inhibitor in 100% DMSO (1.25% final DMSO concentration) was pre-plated using an Echo liquid handler (Labcyte Inc.). Human liver microsomes (Xenotech) were diluted in of 0.1 M phosphate buffer, pH 7.4, at a concentration of 65 μg/ml and 15 μL was added to the 384 well plate. The plates were incubated at ambient room temperature for 30 minutes. After pre-incubation with inhibitor, the reaction was initiated by adding 5 μl of substrate solution (4.0 μM 7α-hydroxy-4-cholesten-3-one(Toronto Research Chemicals), 2 mM of NADPH (Sigma), 0.1 M phosphate buffer (pH 7.4). The reaction was carried out for 45 minutes at ambient room temperature and was quenched by the addition of 50 μl of acetonitrile+0.1% vol/vol formic acid (FA)+300 nM 7α-hydroxy-4-cholesten-3-one-d7 (Toronto Research Chemicals). The plates were sealed and centrifuged at 3000 rpm for 5 minutes. Plates were loaded onto the Agilent RapidFire RF300 HTMS system, wherein samples were sipped for 600 ms, and the sip sensor detection signals the diversion of sample from the loop onto a C4 solid phase extraction (SPE) cartridge, where salts are washed off for 2500 ms with a mobile phase of water with 0.1% vol/vol FA at a flow rate of 1.5 ml/min. The column path is switched, and the sample is eluted off the cartridge and flowed into the mass spectrometer for 3000 ms with a mobile phase of acetonitrile and 0.1% vol/vol FA at a flow rate of 1.25 ml/min. The aspirator tip was washed separately with water and acetonitrile between sample aspirations (each for 600 ms) to minimize carryover contamination. Mass spectrometry was carried out using a Sciex API4000 triple quadrupole mass spectrometer (Applied Biosystems, Concord, ON, Canada) equipped with electrospray ionization (ESI) operated in the positive-ion mode. The product 7α, 12α-dihydroxy-4-cholesten-3-one and internal standard 7α-hydroxy-4-cholsten-3-one-d7 were detected using multiple reaction monitoring (MRM) with Q1/Q3 transitions at m/z 417.3 to 381.3 and m/z 408.3 to 390.3, respectively, with a dwell time of 100 ms and a collision energy of 24 V for each transition. The mass spectrometer used an ESI voltage of 5000 V and a source temperature of 650° C. Extracted ion chromatograms for each transition were integrated and processed using the RapidFire Integrator software. The data for each well were normalized by monitoring product conversion with the ratio of AUCproduct/(AUCinternal standard). The data was then fitted to a four parameter logistic fit using ActivityBase Software to calculate an IC50 of the inhibitor.

What is claimed is:
1. A compound of Formula I:

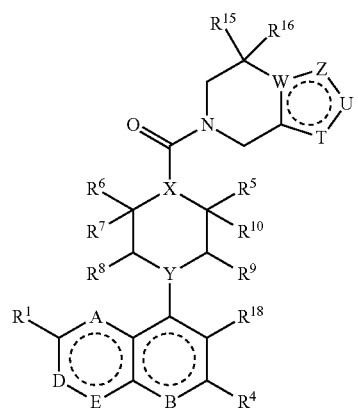

or a pharmaceutically acceptable salt thereof, wherein:
A is N or $CR^{17}$;
B is N or NO;
D is N, $NR^2$ or $CR^2$;
E is N or $CR^3$;
T is N or $CR^{12}$, wherein T is not $CR^{12}$ when W is C and Z is $CR^{14}$ and U is $CR^{13}$;
U is N, O or $CR^{13}$, wherein U is not $CR^{13}$ when W is C and T is $CR^{12}$ and Z is $CR^{14}$;
Z is N, S, O or $CR^{14}$, wherein Z is not $CR^{14}$ when W is C and T is $CR^{12}$ and U is $CR^{13}$;
W is N or C, wherein W is not C when T is $CR^{12}$ and U is $CR^{13}$ and Z is $CR^{14}$;

X is N or CR$^1$;
Y is N or CH;
R$^1$ is selected from the group consisting of hydrogen, halogen, CN, OH, C$_1$-C$_6$alkylOH, C$_1$-C$_6$alkoxy, C$_1$-C$_6$alkylC$_1$-C$_6$alkoxy, haloC$_1$-C$_6$alkoxy, C$_3$-C$_6$cycloalkylC$_1$-C$_6$alkoxy, C$_1$-C$_6$alkyl, haloC$_1$-C$_6$alkyl, C$_3$-C$_6$cycloalkyl, C$_2$-C$_6$alkenyl, COOC1-C$_6$ alkyl, COOC$_1$-C$_6$alkylC$_3$-C$_6$cycloalkyl and oxazole;
R$^2$ is selected from the group consisting of hydrogen, halogen, CN, OH, C$_1$-C$_6$alkylOH, C$_1$-C$_6$alkoxy, C$_1$-C$_6$alkylC$_1$-C$_6$alkoxy, haloC$_1$-C$_6$alkoxy, C$_1$-C$_6$alkoxyC$_3$-C$_6$cycloalkyl, C$_1$-C$_6$alkyl, haloC$_1$-C$_6$alkyl, C$_3$-C$_6$cycloalkyl, C$_2$-C$_6$alkenyl, C$_1$-C$_6$alkylC$_3$-C$_6$cycloalkyl, —OC$_1$-C$_6$alkylC$_3$-C$_6$cycloalkyl, COOC$_1$-C$_6$alkyl, COC$_1$-C$_6$alkyl, COC$_3$-C$_6$cycloalkyl, COOC$_1$-C$_6$alkylC$_3$-C$_6$cycloalkyl, CONH(C$_1$-C$_6$alkyl), CONH(C$_1$-C$_6$alkyl C$_3$-C$_6$cycloalkyl), CONH(C$_3$-C$_6$cycloalkyl), SO$_2$(C$_1$-C$_6$alkyl), pyridine, C$_1$-C$_6$alkoxypyridine, triazole, and oxazole, wherein the oxazole may be substituted with one or more C$_1$-C$_6$alkyl substituents;
R$^3$ is selected from the group consisting of hydrogen, halogen, CN, OH, C$_1$-C$_6$alkylOH, C$_1$-C$_6$alkoxy, C$_1$-C$_6$alkylC$_1$-C$_6$alkoxy, haloC$_1$-C$_6$alkoxy, C$_3$-C$_6$cycloalkylC$_1$-C$_6$alkoxy, C$_1$-C$_6$alkyl, haloC$_1$-C$_6$alkyl, C$_3$-C$_6$cycloalkyl, C$_2$-C$_6$alkenyl, COOC$_1$-C$_6$alkyl, COOC1-C$_6$ alkylC$_3$-C$_6$cycloalkyl and oxazole;
R$^4$ is selected from the group consisting of hydrogen, halogen, CN, OH, C$_1$-C$_6$alkylOH, C$_1$-C$_6$alkoxy, C$_1$-C$_6$alkylC$_1$-C$_6$alkoxy, haloC$_1$-C$_6$alkoxy, C$_3$-C$_6$cycloalkylC$_1$-C$_6$alkoxy, C$_1$-C$_6$alkyl, haloC$_1$-C$_6$alkyl, C$_3$-C$_6$cycloalkyl, C$_2$-C$_6$alkenyl, COOC$_1$-C$_6$alkyl, COOC1-C$_6$ alkylC$_3$-C$_6$cycloalkyl and oxazole;
R$^5$ is selected from the group consisting of hydrogen, halogen, C$_1$-C$_6$alkyl, C$_3$-C$_6$cycloalkyl, C$_1$-C$_6$alkoxy and haloC$_1$-C$_6$alkyl or when taken with R$^{10}$ forms a C$_3$-C$_6$cycloalkyl;
R$^6$ is selected from the group consisting of hydrogen, halogen, C$_1$-C$_6$alkyl, C$_3$-C$_6$cycloalkyl, C$_1$-C$_6$alkoxy and haloC$_1$-C$_6$alkyl or when taken with R$^7$ forms a C$_3$-C$_6$cycloalkyl, or when taken with R$^{11}$ forms a C$_3$-C$_6$cycloalkyl;
R$^7$ is selected from the group consisting of hydrogen, halogen, C$_1$-C$_6$alkyl, C$_3$-C$_6$cycloalkyl, C$_1$-C$_6$alkoxy and haloC$_1$-C$_6$alkyl or when taken with R$^6$ forms a C$_3$-C$_6$cycloalkyl;
R$^8$ is selected from the group consisting of hydrogen, halogen, C$_1$-C$_6$alkyl, C$_3$-C$_6$cycloalkyl, C$_1$-C$_6$alkoxy and haloC$_1$-C$_6$alkyl;
R$^9$ is selected from the group consisting of hydrogen, halogen, C$_1$-C$_6$alkyl, C$_3$-C$_6$cycloalkyl, C$_1$-C$_6$alkoxy and haloC$_1$-C$_6$alkyl;
R$^{10}$ is selected from the group consisting of hydrogen, halogen, C$_1$-C$_6$alkyl, C$_3$-C$_6$cycloalkyl, C$_1$-C$_6$alkoxy and haloC$_1$-C$_6$alkyl or when taken with R$^5$ forms a C$_3$-C$_6$cycloalkyl;
R$^{11}$ is selected from the group consisting of hydrogen, halogen, OH, C$_1$-C$_6$alkyl, and haloC$_1$-C$_6$alkyl or when taken with R$^6$ forms a C$_3$-C$_6$cycloalkyl;
R$^{12}$ is selected from the group consisting of hydrogen, halogen, OH, C$_1$-C$_6$alkyl, C$_3$-C$_6$cycloalkyl and haloC$_1$-C$_6$alkyl;
R$^{13}$ is selected from the group consisting of hydrogen, halogen, OH, C$_1$-C$_6$alkyl, C$_3$-C$_6$cycloalkyl and haloC$_1$-C$_6$alkyl;
R$^{14}$ is selected from the group consisting of hydrogen, halogen, OH, C$_1$-C$_6$alkyl, C$_3$-C$_6$cycloalkyl and haloC$_1$-C$_6$alkyl;
R$^{15}$ is selected from the group consisting of hydrogen, halogen, OH, C$_1$-C$_6$alkyl, and haloC$_1$-C$_6$alkyl;
R$^{16}$ is selected from the group consisting of hydrogen, halogen, OH, C$_1$-C$_6$alkyl, and haloC$_1$-C$_6$alkyl;
R$^{17}$ is selected from the group consisting of hydrogen, halogen, C$_1$-C$_6$alkyl, C$_1$-C$_6$alkoxy, and haloC$_1$-C$_6$alkyl; and
R$^{18}$ is selected from the group consisting of hydrogen, halogen, C$_1$-C$_6$alkyl, C$_3$-C$_6$cycloalkyl, C$_1$-C$_6$alkoxy, NO$^2$, CONH$_2$, haloC$_1$-C$_6$alkyl and COOC$_1$-C$_6$alkyl.

2. The compound of claim 1, or a pharmaceutically acceptable salt thereof, wherein Y is N.

3. The compound of claim 1, or a pharmaceutically acceptable salt thereof, wherein B is N.

4. The compound of claim 1, or a pharmaceutically acceptable salt thereof, wherein X is CR$^{11}$, wherein R$^{11}$ is hydrogen.

5. The compound of claim 1, or a pharmaceutically acceptable salt thereof, wherein Z is CR$^{14}$, wherein R$^{14}$ is trifluoromethyl.

6. The compound of claim 1, or a pharmaceutically acceptable salt thereof, wherein T is N.

7. The compound of claim 1, or a pharmaceutically acceptable salt thereof, wherein W is N.

8. The compound of claim 1, or a pharmaceutically acceptable salt thereof, wherein U is N.

9. The compound of claim 1, or a pharmaceutically acceptable salt thereof, wherein A is CR$^{17}$, wherein R$^{17}$ is hydrogen.

10. The compound of claim 1, or a pharmaceutically acceptable salt thereof, wherein E is CR$^3$, wherein R$^3$ is hydrogen.

11. The compound of claim 1, or a pharmaceutically acceptable salt thereof, wherein D is CR$^2$.

12. The compound of claim 11, or a pharmaceutically acceptable salt thereof, wherein R$^2$ is selected from the group consisting of halogen and haloC$_1$-C$_6$alkyl.

13. The compound of claim 11, or a pharmaceutically acceptable salt thereof, wherein R$^2$ is haloC$_1$-C$_6$alkyl.

14. The compound of claim 1, or a pharmaceutically acceptable salt thereof, wherein R$^6$ is methyl and R$^5$, R$^7$, R$^8$, R$^9$, R$^{10}$, R$^{15}$ and R$^{16}$ are hydrogen.

15. A compound which is:

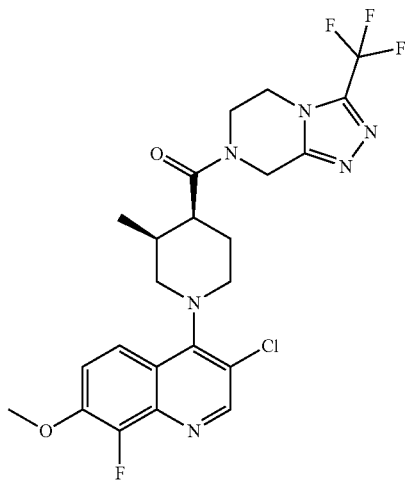 [SMILES: COc1ccc2c(N3CC[C@H](C(=O)N4CCn5c(nnc5C(F)(F)F)C4)[C@H](C)C3)c(Cl)cnc2c1F]
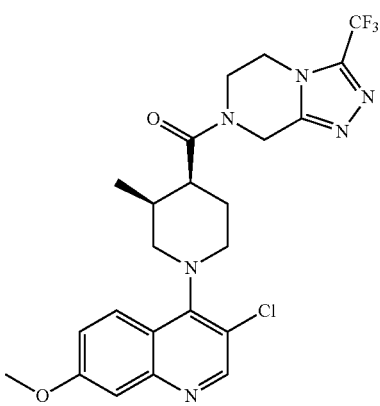
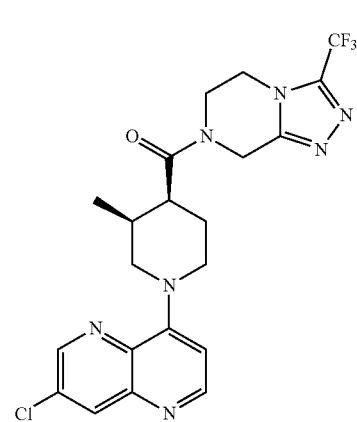 [SMILES: C[C@@H]1CN(c2ccnc3cc(Cl)cnc23)CC[C@@H]1C(=O)N1CCn2c(nnc2C(F)(F)F)C1]
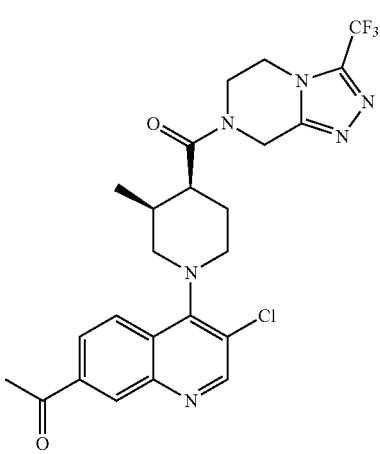 [SMILES: CC(=O)c1ccc2c(N3CC[C@H](C(=O)N4CCn5c(nnc5C(F)(F)F)C4)[C@H](C)C3)c(Cl)cnc2c1]
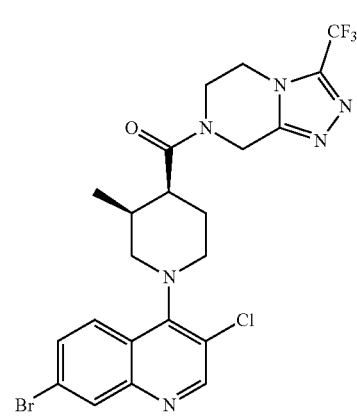 [SMILES: C[C@@H]1CN(c2c(Cl)cnc3cc(F)ccc23)CC[C@@H]1C(=O)N1CCn2c(nnc2C(F)(F)F)C1]
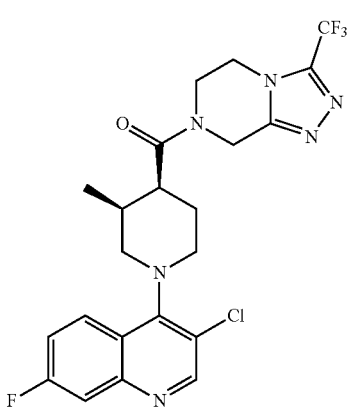

149
-continued
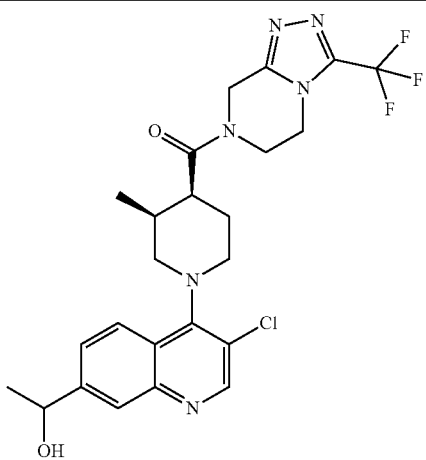
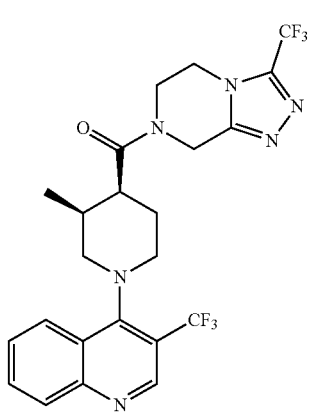 [SMILES: C[C@@H]1CN(c2c(C(F)(F)F)cnc3ccccc23)CC[C@@H]1C(=O)N1CCn2c(nnc2C(F)(F)F)C1]
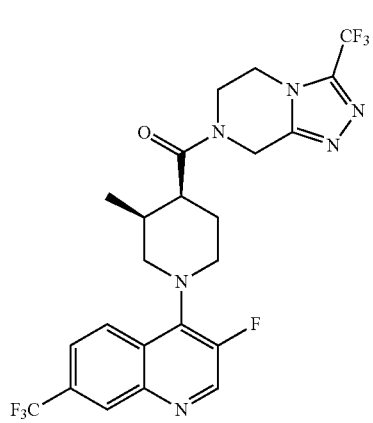
150
-continued
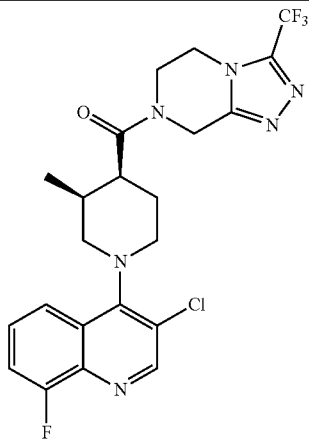
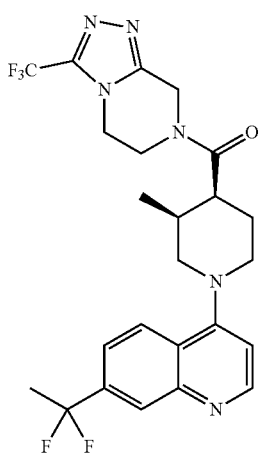 [SMILES: C[C@@H]1CN(c2ccnc3cc(C(C)(F)F)ccc23)CC[C@@H]1C(=O)N1CCn2c(nnc2C(F)(F)F)C1]
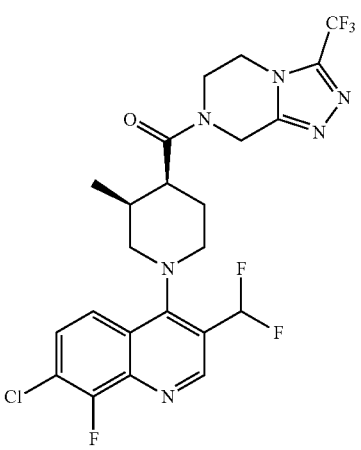 [SMILES: C[C@@H]1CN(c2c(C(F)F)cnc3c(F)c(Cl)ccc23)CC[C@@H]1C(=O)N1CCn2c(nnc2C(F)(F)F)C1]

| 151 -continued | 152 -continued |
|---|---|
| 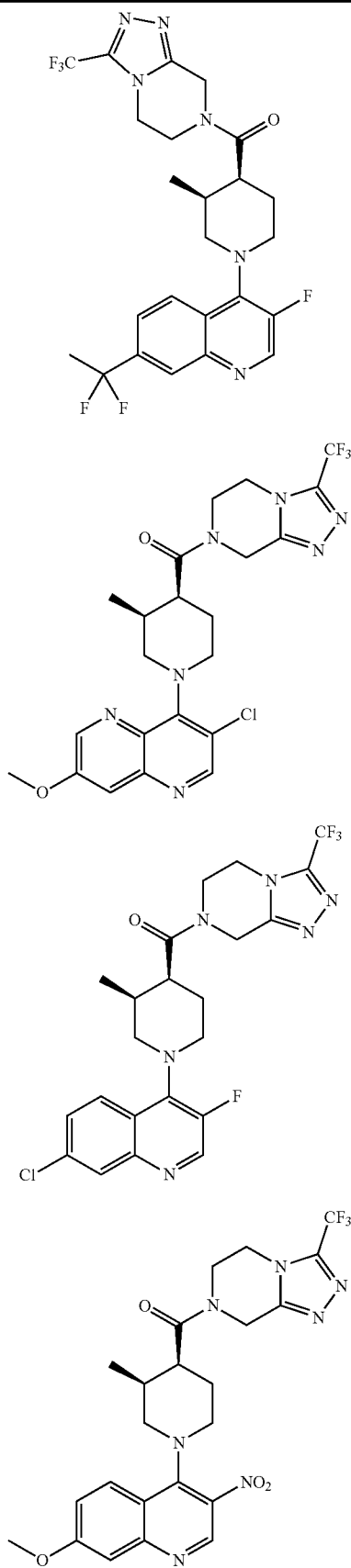 | 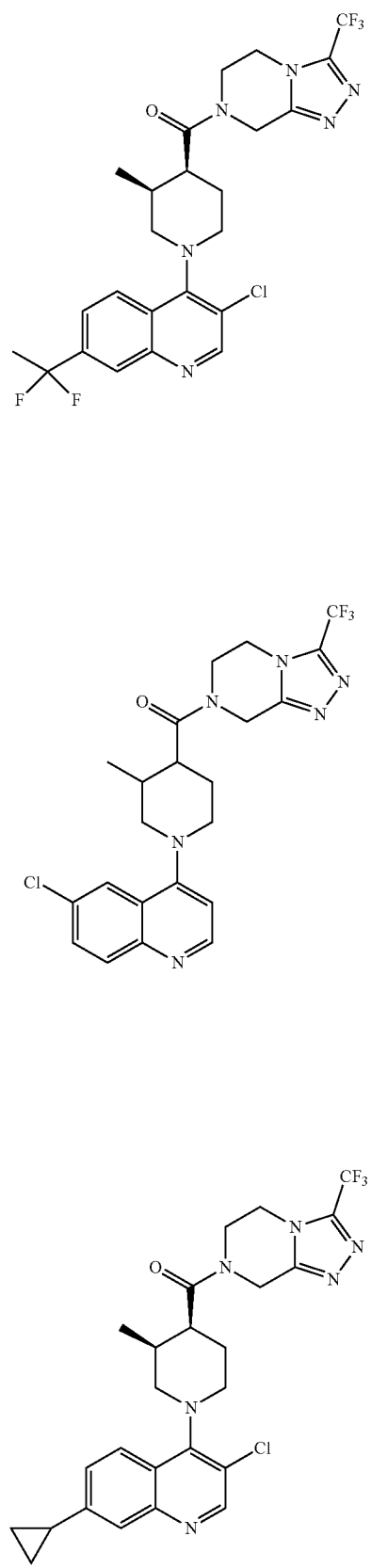 |

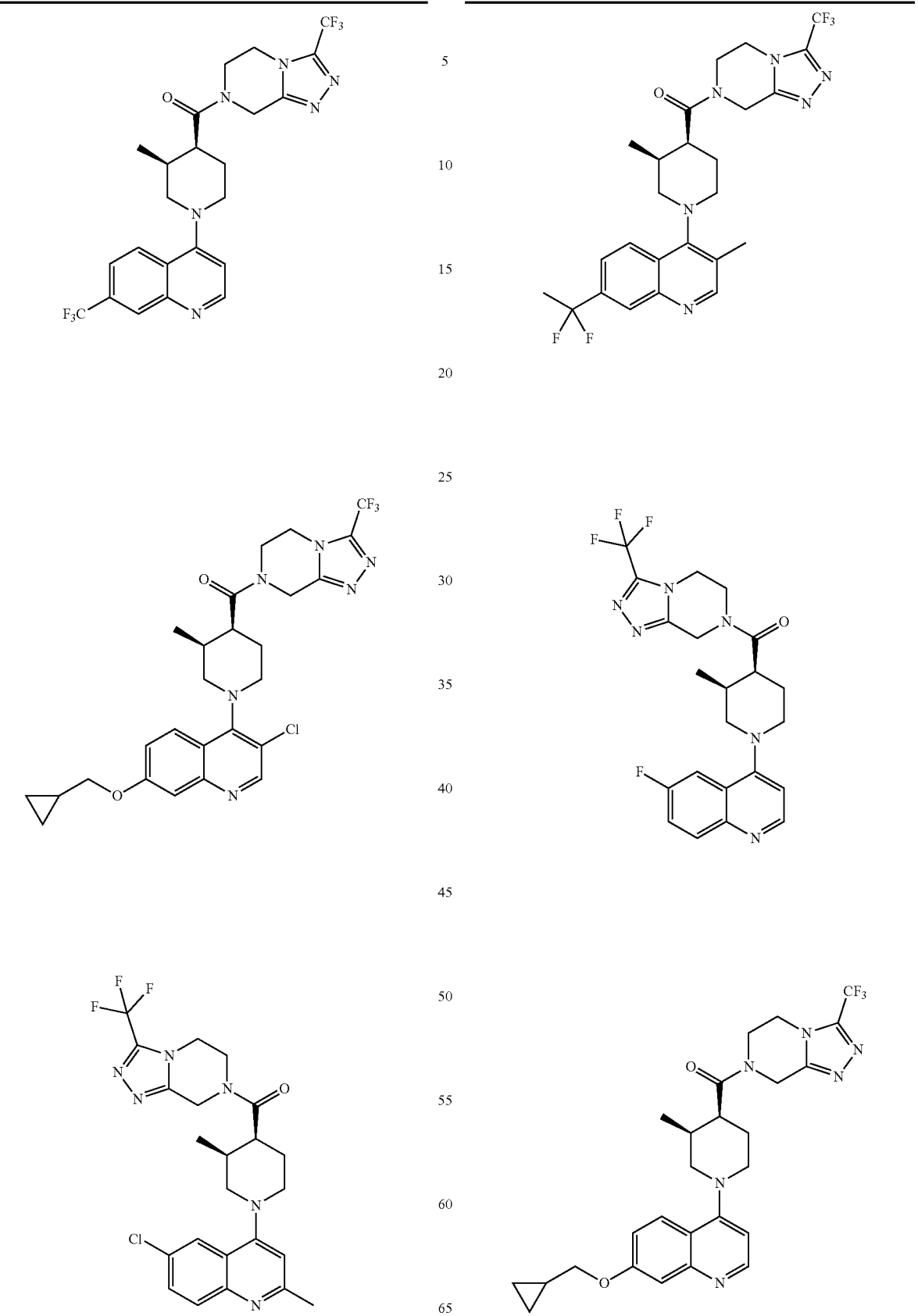

155
-continued
156
-continued
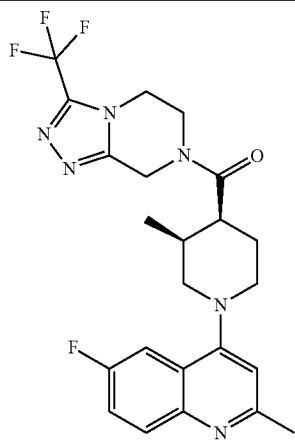
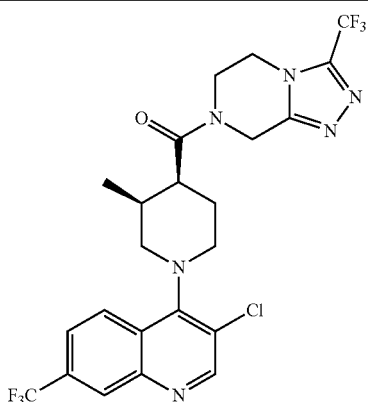
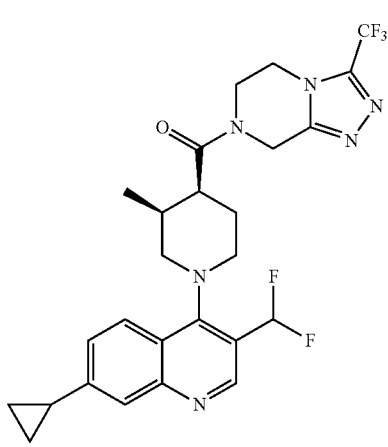 [SMILES: C[C@@H]1CN(c2c(C(F)F)cnc3cc(C4CC4)ccc23)CC[C@@H]1C(=O)N1CCn2c(nnc2C(F)(F)F)C1]
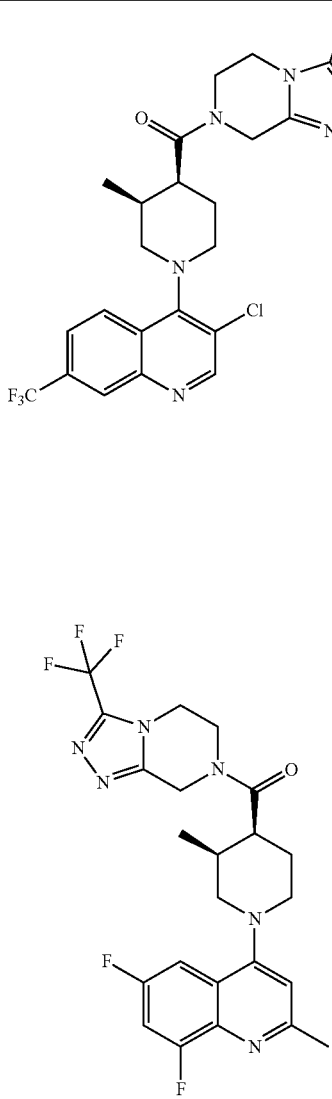
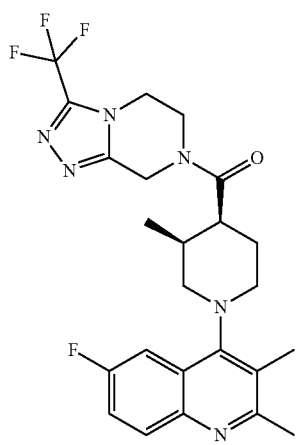 [SMILES: Cc1nc2ccc(F)cc2c(N2CC[C@H](C(=O)N3CCn4c(nnc4C(F)(F)F)C3)[C@H](C)C2)c1C]

| 157 -continued | 158 -continued |
|---|---|
| 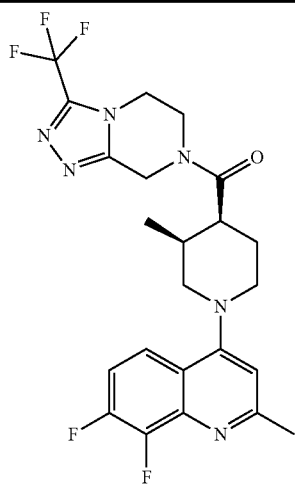 | 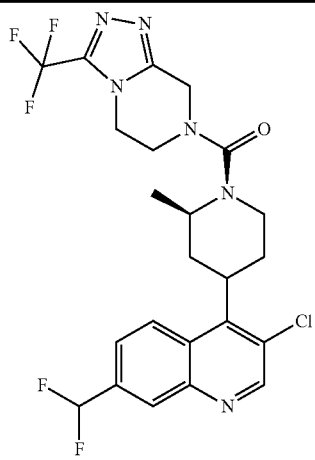 |
| 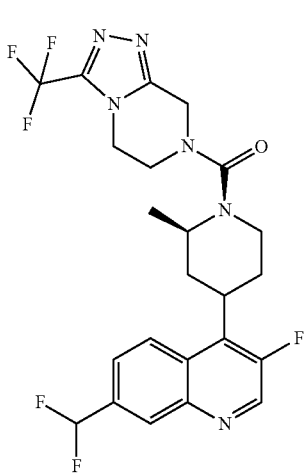 | 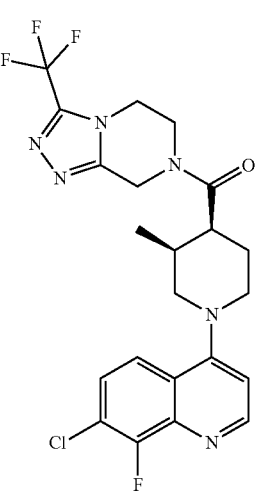 |
| 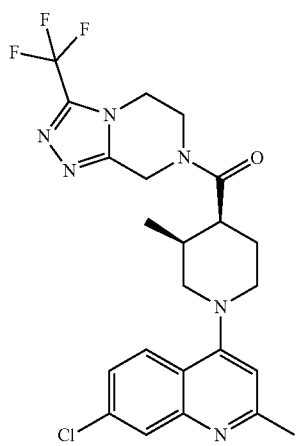 [SMILES: Cc1cc(N2CC[C@H](C(=O)N3CCn4c(nnc4C(F)(F)F)C3)[C@H](C)C2)c2ccc(Cl)cc2n1] | 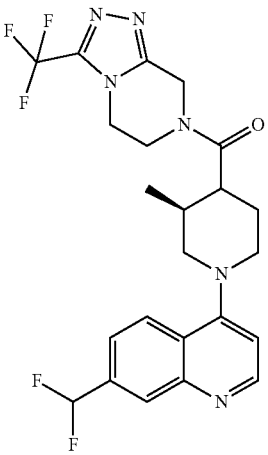 [SMILES: C[C@@H]1CN(c2ccnc3cc(C(F)F)ccc23)CCC1C(=O)N1CCn2c(nnc2C(F)(F)F)C1] |

159
-continued
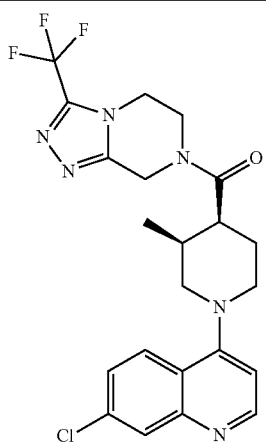
160
-continued
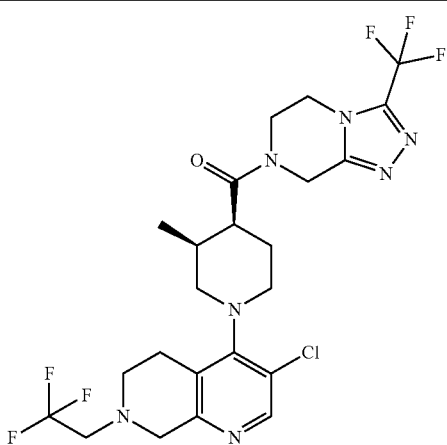
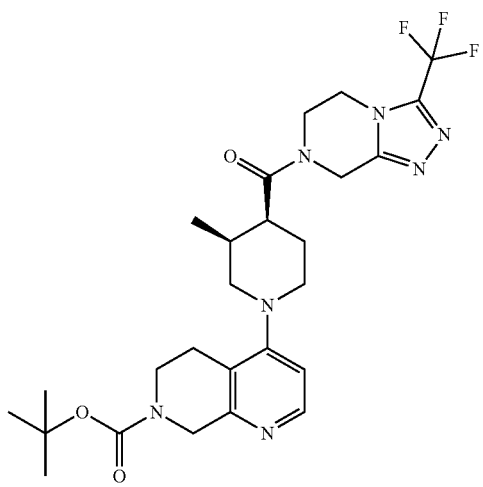 [SMILES: C[C@@H]1CN(c2ccnc3c2CCN(C(=O)OC(C)(C)C)C3)CC[C@@H]1C(=O)N1CCn2c(nnc2C(F)(F)F)C1]
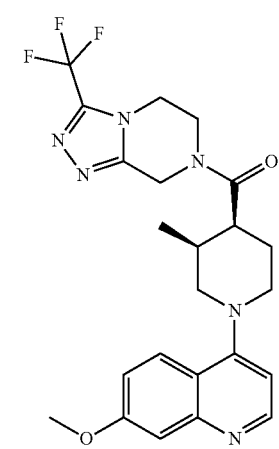
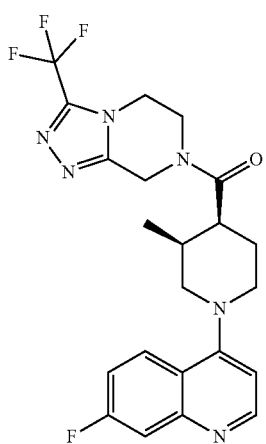 [SMILES: C[C@@H]1CN(c2ccnc3cc(F)ccc23)CC[C@@H]1C(=O)N1CCn2c(nnc2C(F)(F)F)C1]
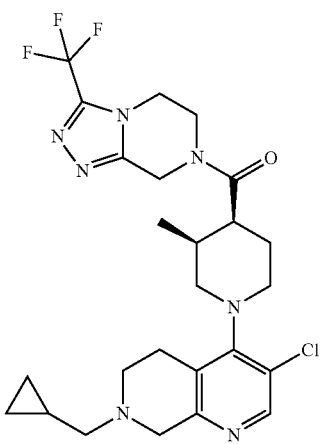 [SMILES: C[C@@H]1CN(c2c(Cl)cnc3c2CCN(CC2CC2)C3)CC[C@@H]1C(=O)N1CCn2c(nnc2C(F)(F)F)C1]

161
-continued
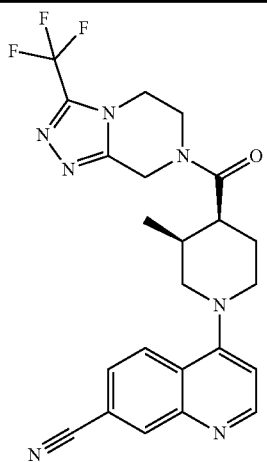
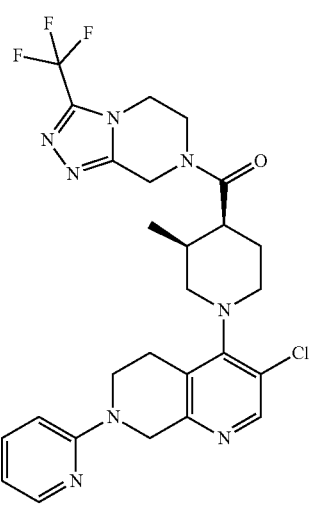 [SMILES: C[C@@H]1CN(c2c(Cl)cnc3c2CCN(c2ccccn2)C3)CC[C@@H]1C(=O)N1CCn2c(nnc2C(F)(F)F)C1]
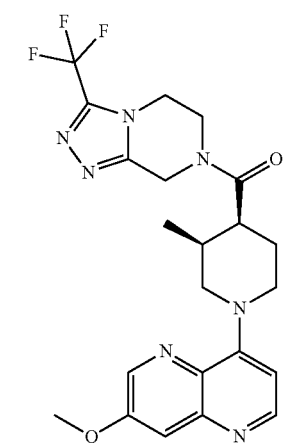
162
-continued
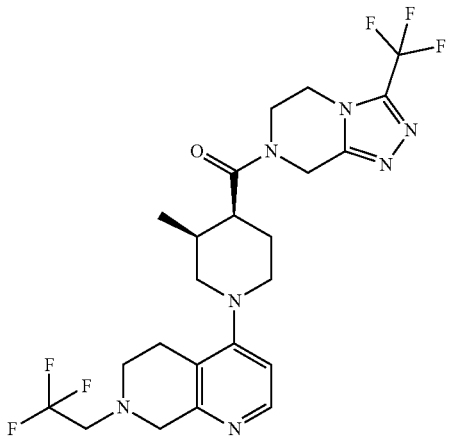 [SMILES: C[C@@H]1CN(c2ccnc3c2CCN(CC(F)(F)F)C3)CC[C@@H]1C(=O)N1CCn2c(nnc2C(F)(F)F)C1]
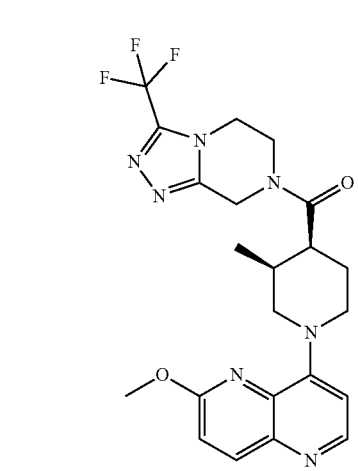 [SMILES: COc1ccc2nccc(N3CC[C@H](C(=O)N4CCn5c(nnc5C(F)(F)F)C4)[C@H](C)C3)c2n1]
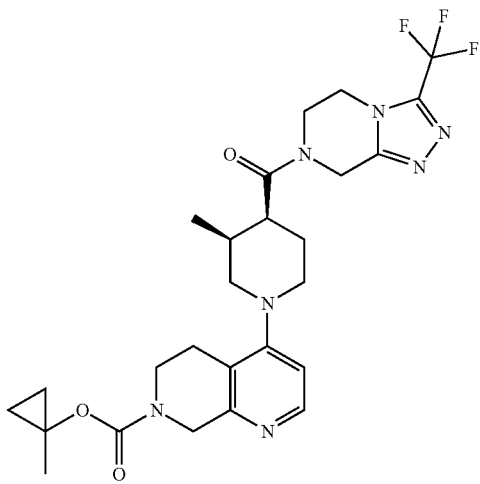 [SMILES: C[C@@H]1CN(c2ccnc3c2CCN(C(=O)OC2(C)CC2)C3)CC[C@@H]1C(=O)N1CCn2c(nnc2C(F)(F)F)C1]

163
-continued
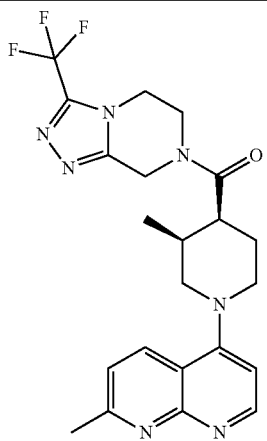
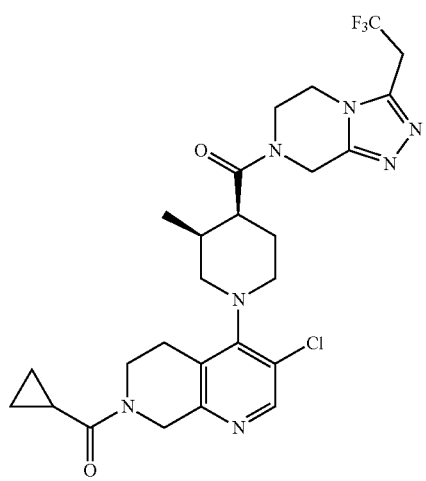 [SMILES: C[C@@H]1CN(c2c(Cl)cnc3c2CCN(C(=O)C2CC2)C3)CC[C@@H]1C(=O)N1CCn2c(nnc2CC(F)(F)F)C1]
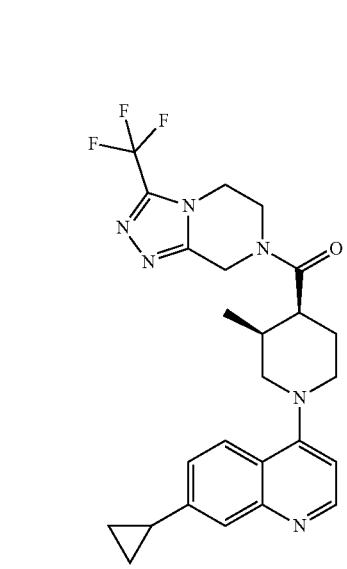 [SMILES: C[C@@H]1CN(c2ccnc3cc(C4CC4)ccc23)CC[C@@H]1C(=O)N1CCn2c(nnc2C(F)(F)F)C1]
164
-continued
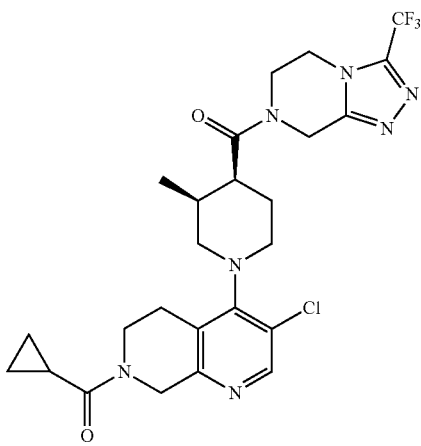 [SMILES: C[C@@H]1CN(c2c(Cl)cnc3c2CCN(C(=O)C2CC2)C3)CC[C@@H]1C(=O)N1CCn2c(nnc2C(F)(F)F)C1]
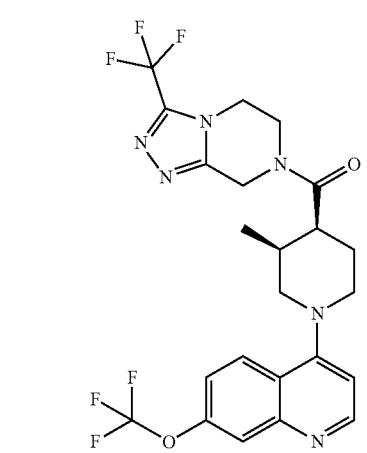 [SMILES: C[C@@H]1CN(c2ccnc3cc(OC(F)(F)F)ccc23)CC[C@@H]1C(=O)N1CCn2c(nnc2C(F)(F)F)C1]
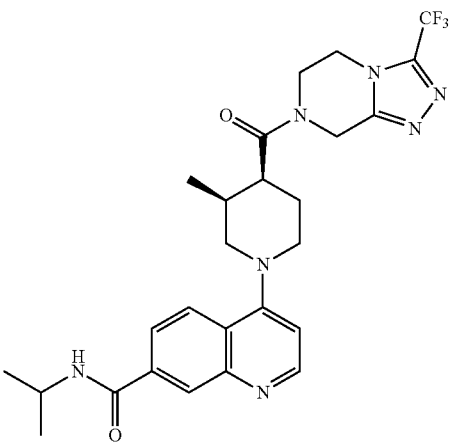 [SMILES: CC(C)NC(=O)c1ccc2c(N3CC[C@H](C(=O)N4CCn5c(nnc5C(F)(F)F)C4)[C@H](C)C3)ccnc2c1]

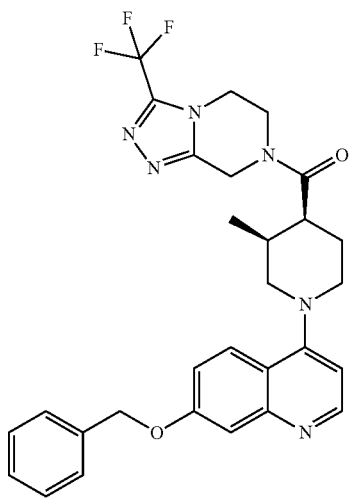 [SMILES: C[C@@H]1CN(c2ccnc3cc(OCc4ccccc4)ccc23)CC[C@@H]1C(=O)N1CCn2c(nnc2C(F)(F)F)C1]
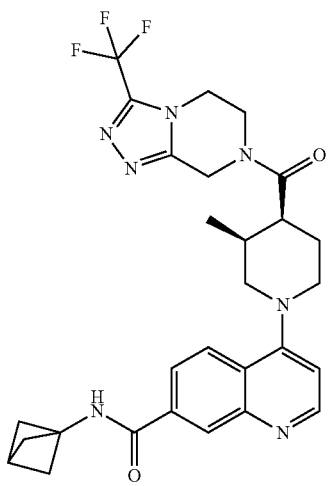
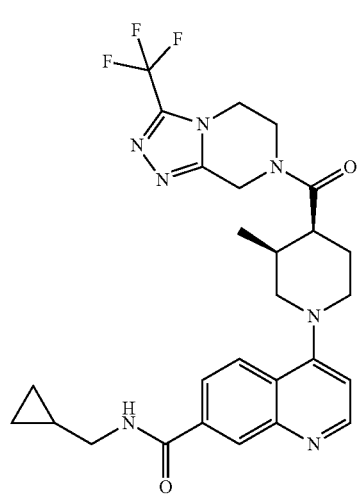 [SMILES: C[C@@H]1CN(c2ccnc3cc(C(=O)NCC4CC4)ccc23)CC[C@@H]1C(=O)N1CCn2c(nnc2C(F)(F)F)C1]
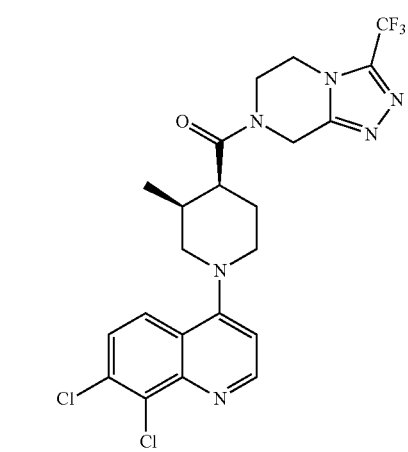
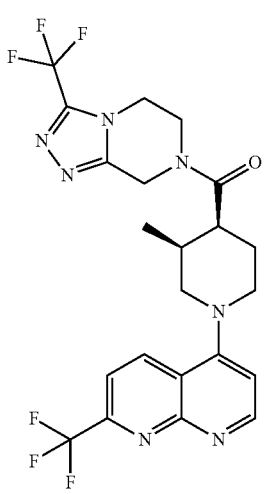 [SMILES: C[C@@H]1CN(c2ccnc3nc(C(F)(F)F)ccc23)CC[C@@H]1C(=O)N1CCn2c(nnc2C(F)(F)F)C1]
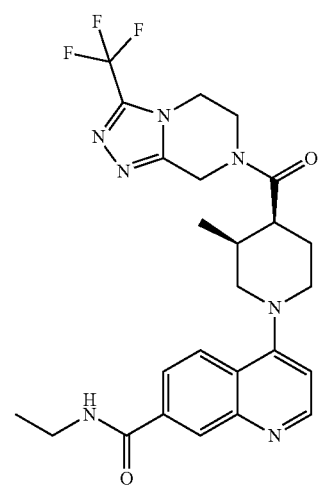 [SMILES: CCNC(=O)c1ccc2c(N3CC[C@H](C(=O)N4CCn5c(nnc5C(F)(F)F)C4)[C@H](C)C3)ccnc2c1]

167
-continued
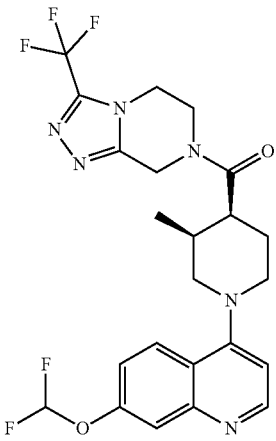 [SMILES: C[C@@H]1CN(c2ccnc3cc(OC(F)F)ccc23)CC[C@@H]1C(=O)N1CCn2c(nnc2C(F)(F)F)C1]
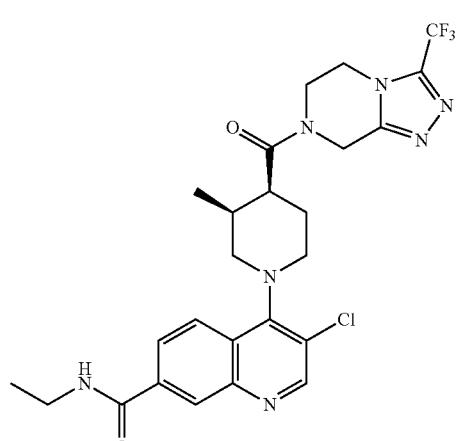
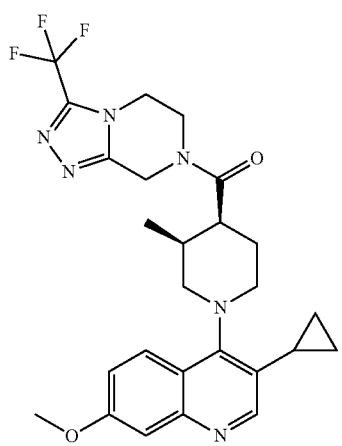 [SMILES: COc1ccc2c(N3CC[C@H](C(=O)N4CCn5c(nnc5C(F)(F)F)C4)[C@H](C)C3)c(C3CC3)cnc2c1]
168
-continued
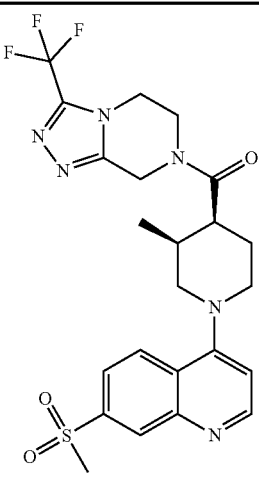
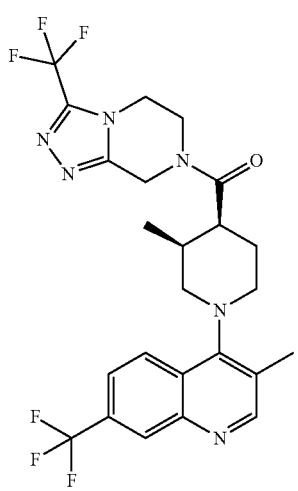 [SMILES: Cc1cnc2cc(C(F)(F)F)ccc2c1N1CC[C@H](C(=O)N2CCn3c(nnc3C(F)(F)F)C2)[C@H](C)C1]
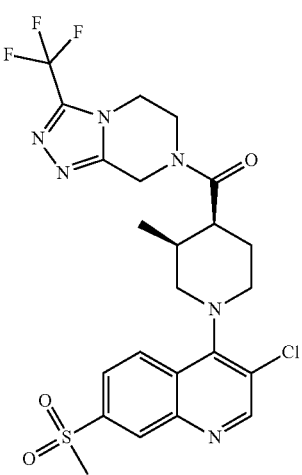 [SMILES: C[C@@H]1CN(c2c(Cl)cnc3cc(S(C)(=O)=O)ccc23)CC[C@@H]1C(=O)N1CCn2c(nnc2C(F)(F)F)C1]

| 169 -continued | 170 -continued |
|---|---|
| 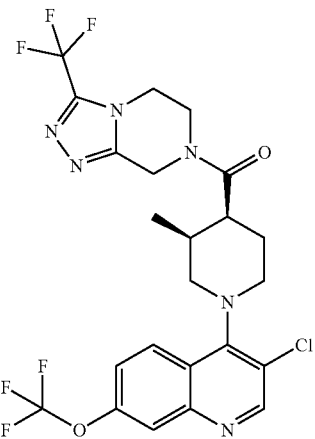 [SMILES: C[C@@H]1CN(c2c(Cl)cnc3cc(OC(F)(F)F)ccc23)CC[C@@H]1C(=O)N1CCn2c(nnc2C(F)(F)F)C1] | 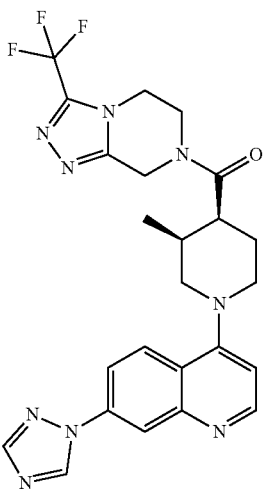 |
| 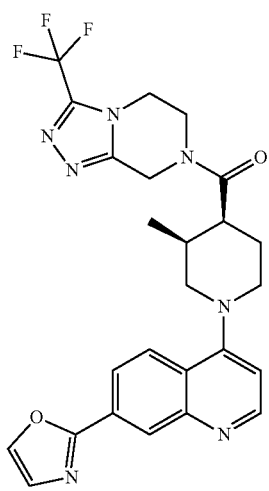 [SMILES: C[C@@H]1CN(c2ccnc3cc(-c4ncco4)ccc23)CC[C@@H]1C(=O)N1CCn2c(nnc2C(F)(F)F)C1] | 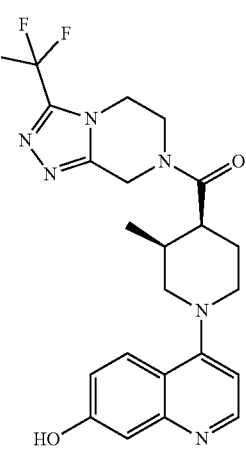 |
| 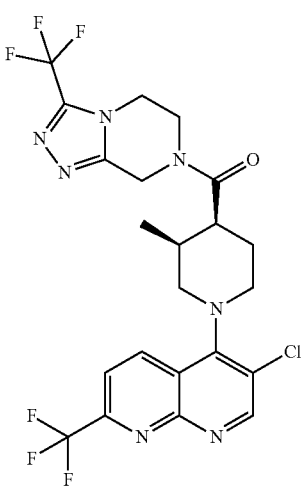 [SMILES: C[C@@H]1CN(c2c(Cl)cnc3nc(C(F)(F)F)ccc23)CC[C@@H]1C(=O)N1CCn2c(nnc2C(F)(F)F)C1] | 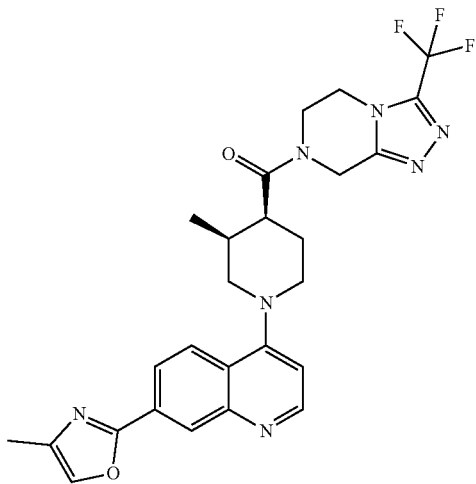 [SMILES: Cc1coc(-c2ccc3c(N4CC[C@H](C(=O)N5CCn6c(nnc6C(F)(F)F)C5)[C@H](C)C4)ccnc3c2)n1] |

| 171 -continued | 172 -continued |
|---|---|
| 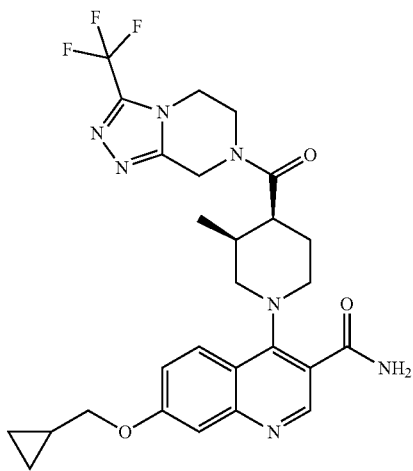 [SMILES: C[C@@H]1CN(c2c(C(N)=O)cnc3cc(OCC4CC4)ccc23)CC[C@@H]1C(=O)N1CCn2c(nnc2C(F)(F)F)C1] | 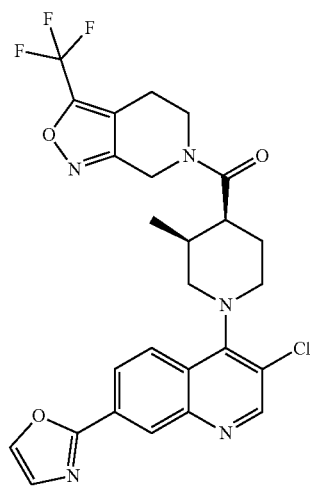 [SMILES: C[C@@H]1CN(c2c(Cl)cnc3cc(-c4ncco4)ccc23)CC[C@@H]1C(=O)N1CCc2c(noc2C(F)(F)F)C1] |
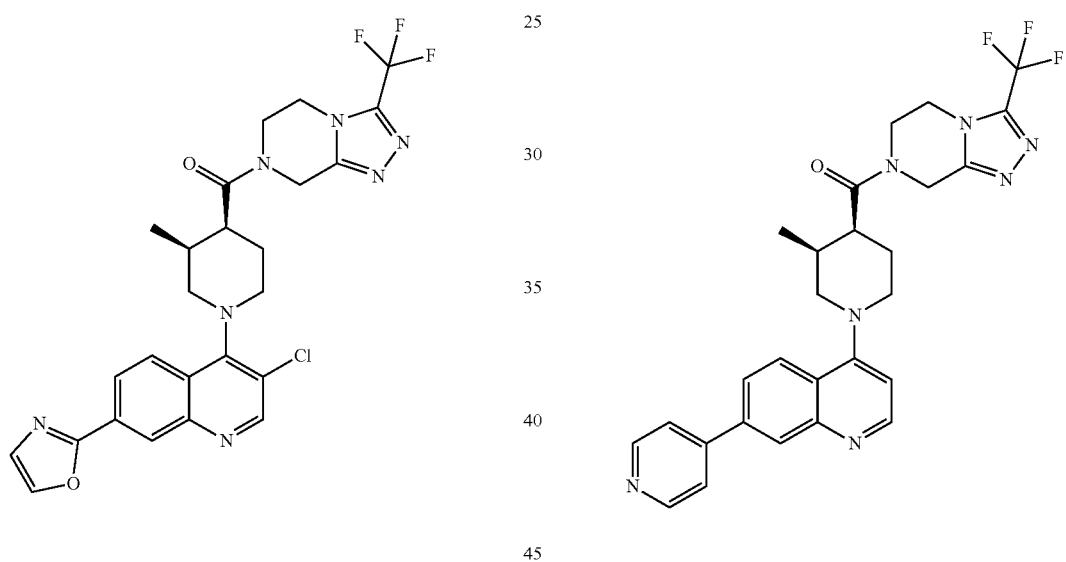
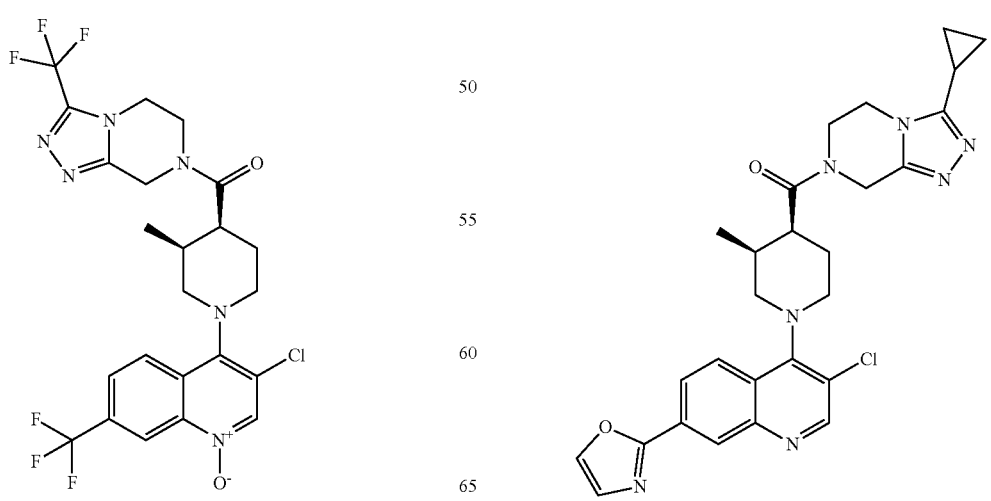

-continued

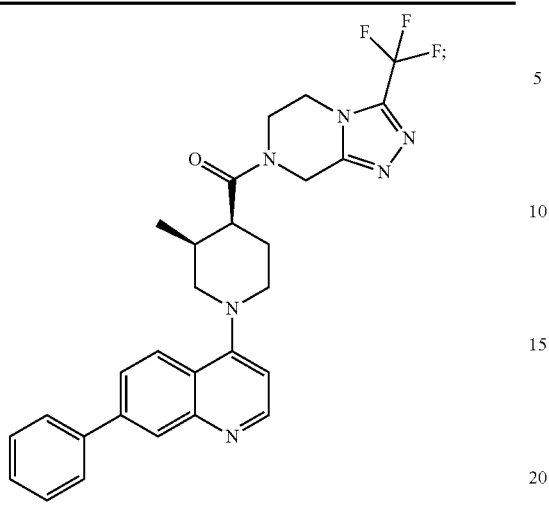

or a pharmaceutically acceptable salt thereof.

16. A method of treating diabetes comprising administering to a patient in need thereof a compound, or pharmaceutically acceptable salt thereof, of claim 1.

17. A pharmaceutical composition comprising a compound of claim 1, or a pharmaceutically acceptable salt thereof and a pharmaceutically acceptable carrier.

18. A pharmaceutical composition comprising a compound of claim 1 and a pharmaceutically acceptable carrier.

* * * * *